United States Patent
Bruton et al.

(10) Patent No.: US 7,592,347 B2
(45) Date of Patent: Sep. 22, 2009

(54) PIPERAZINE DERIVATES AND THEIR USE FOR THE TREATMENT OF NEUROLOGICAL AND PSYCHIATRIC DISEASES

(75) Inventors: Gordon Bruton, Harlow (GB); Barry Sidney Orlek, Harlow (GB); Kishore Kalidas Rana, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 564 days.

(21) Appl. No.: 10/553,803

(22) PCT Filed: Apr. 21, 2004

(86) PCT No.: PCT/EP2004/004245

§ 371 (c)(1),
(2), (4) Date: Oct. 17, 2005

(87) PCT Pub. No.: WO2004/101546

PCT Pub. Date: Nov. 25, 2004

(65) Prior Publication Data

US 2007/0054917 A1      Mar. 8, 2007

(30) Foreign Application Priority Data

Apr. 23, 2003   (GB) ................. 0309222.8
Oct. 2, 2003    (GB) ................. 0323109.9

(51) Int. Cl.
| | |
|---|---|
| A61P 25/28 | (2006.01) |
| A61K 31/496 | (2006.01) |
| A61K 31/501 | (2006.01) |
| A61K 31/506 | (2006.01) |
| C07D 211/62 | (2006.01) |
| C07D 401/00 | (2006.01) |
| C07D 405/00 | (2006.01) |
| C07D 413/00 | (2006.01) |
| C07D 417/00 | (2006.01) |

(52) U.S. Cl. .............. 514/253.09; 514/253.1; 514/253.11; 514/253.13; 544/364; 544/365

(58) Field of Classification Search .......... 514/253.1, 514/253.09, 253.11, 253.13; 544/364, 365
See application file for complete search history.

(56) References Cited

U.S. PATENT DOCUMENTS

| | | | |
|---|---|---|---|
| 5,364,791 A | 11/1994 | Vegeto et al. | |
| 5,874,534 A | 2/1999 | Vegeto et al. | |
| 5,935,934 A | 8/1999 | Vegeto et al. | |
| 6,093,718 A | 7/2000 | Waterson et al. | |
| 2002/0115854 A1 | 8/2002 | Lam et al. | |
| 2003/0073718 A1 | 4/2003 | Barta et al. | |

FOREIGN PATENT DOCUMENTS

| | | |
|---|---|---|
| WO | WO96/10022 | 4/1996 |
| WO | WO97/06802 | 2/1997 |
| WO | WO97/23462 | 7/1997 |
| WO | WO02/32893 | 4/2002 |
| WO | WO02/47679 | 6/2002 |
| WO | WO02/072570 | 9/2002 |
| WO | WO02/076925 | 10/2002 |
| WO | WO03/004480 | 1/2003 |
| WO | WO03/024928 | 3/2003 |
| WO | WO03/024929 | 3/2003 |
| WO | WO03/062234 | 7/2003 |
| WO | WO03/088967 | 10/2003 |
| WO | WO03/103669 | 12/2003 |
| WO | 2004037800 A1 | 5/2004 |

OTHER PUBLICATIONS

Cottet et al., Trifluoromethyl-Substituted Pyridines Through Displacement of Iodine by in situ Generated (Trifluoromethyl)copper, Eur. J. Org. Chem 327-330 (2002).
Cottet et al., Recommendable Routes to Trifluoromethyl-Substituted Pyridine- and Quinolinecarboxylic Acids, Eur. J. Org. Chem 1559-1568 (2003).
Giovannini et al., "Effects of histamine $H_3$ receptor agonista and antagonists on cognitive performance and scopolamine-induced amnesia," Behaviural Brain Res. 104:147-155 (1999).
Goodman et al., Desymmetrization of Dichloroazaheterocycles, Tetrahedon 55:15067-15070 (1999).
Leurs et al., "Therapeutic potential of histamine $H_3$ receptor agonists and antagonists," TiPS 19:177-183 (May 1998).
Lovenberg et al., "Cloning and Funcational Expression of the Human Histamine $H_3$ Receptor," Molecular Pharmacology 55:1101-1107 (1999).
Mickelson et al., Asymmetric Synthesis of 2,6-Methylated Piperazines, J. Org. Chem. 60:4177-4183 (1995).
Onodera and Watanabe, "Histamine $H_3$ Antagonists as Potential Therapeutics in the CNS," ed Leurs and Timmerman, pp. 255-267, Elsevier Science B.V. (1998).
Sakamoto et al., Site-Selectivity in the Cyanation of 3-Substituted Pyridine 1 Oxides with Trimethylsilanecarbonitrile, Chem. Pharm. Bull. 33(2):565-571 (1985).
Schlicker et al., "Modulation of neurotransmitter release via histamine $H_3$ heterorecptors," Fundam Clin Pharmacol 8:128-137 (1994).

*Primary Examiner*—Brenda L Coleman
(74) *Attorney, Agent, or Firm*—Bonnie L. Deppenbrock

(57) ABSTRACT

The present invention relates to novel piperidine carbonyl piperazine derivatives having pharmacological activity, processes for their preparation, to compositions containing them and to their use in the treatment of neurological and psychiatric disorders.

22 Claims, No Drawings

PIPERAZINE DERIVATES AND THEIR USE FOR THE TREATMENT OF NEUROLOGICAL AND PSYCHIATRIC DISEASES

CROSS-REFERENCE TO RELATED APPLICATIONS

This application is filed pursuant to 35 USC 371 as a United States National Phase Application of International Patent Application Serial No. PCT/EP2004/004245 filed on Apr. 21, 2004, which claims priority from 0309222.8 filed on Apr. 23, 2003 and 0323109.9 filed on Oct. 2, 2003 in the United Kingdom.

FIELD OF THE INVENTION

The present invention relates to novel piperidine carbonyl piperazine derivatives having pharmacological activity, processes for their preparation, to compositions containing them and to their use in the treatment of neurological and psychiatric disorders.

BACKGROUND OF THE INVENTION

WO 97/06802 (Zeneca Limited) describe a series of pyridyl and pyrimidyl derivatives as oxido-squalene cyclase inhibitors which are claimed to lower blood cholesterol. WO 02/76925 (Eli Lilly), WO 03/004480, WO 03/024928 and WO 03/024929 (all Novo Nordisk A/S and Boehringer Ingelheim International) describe a series of substituted piperidines or piperazines which are claimed to bind selectively to the histamine H3 receptor. WO 03/62234 (Yamanouchi Pharmaceutical Co) describe a series of quinoxaline derivatives as poly(ADP-ribose) polymerase inhibitors. US2002115854 (Bristol Myers Squibb) describe a series of heterocyclic compounds as thrombin or factor Xa inhibitors. WO 97/23462 (Pfizer Inc) describe a series of quinoline and quinoxaline derivatives for treating a range of indications including benign prostatic hyperplasia, hypertension and hyperlipidaemia. WO 96/10022 (Zeneca Ltd) describe a series of heterocyclic compounds containing amino-aza-cyclyl and aryl groups as factor Xa protease and blood coagulation inhibitors. WO 03/103669 and WO 03/088967 (both Schering Corp) describe a series of piperidinyl benzimidazolone compounds as histamine H3 antagonists. WO 02/32893 and WO 02/72570 (both Schering Corp) describe a series of non-imidazole compounds as histamine H3 antagonists.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp 255-267, Elsevier Science B. V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

SUMMARY OF THE INVENTION

The present invention provides, in a first aspect, a compound of formula (I) or a pharmaceutically acceptable salt thereof:

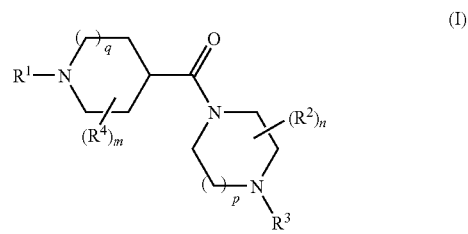

wherein:
$R^1$ represents aryl, heteroaryl, -aryl-X-$C_{3-7}$ cycloalkyl, -heteroaryl-X-$C_{3-7}$ cycloalkyl, -aryl- X-aryl, -aryl-X-heteroaryl, -aryl-X-heterocyclyl, -heteroaryl-X-heteroaryl, -heteroaryl-X-aryl or -heteroaryl-X-heterocyclyl;
wherein said aryl, heteroaryl and heterocyclyl groups of $R^1$ may be optionally substituted by one or more (eg. 1, 2 or 3) substituents which may be the same or different, and which are selected from the group consisting of halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, —CO$C_{1-6}$ alkyl, —CO$C_{1-6}$ alkyl-halogen, —CO$C_{1-6}$ alkyl-cyano, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, CI4 alkylsulfonamido$C_{1-6}$ alkyl, $C_{1-6}$ alkylamido$C_{1-6}$ alkyl, aryl, arylsulfonyl, arylsulfonyloxy, aryloxy, arylsulfonamido, arylcarboxamido, aroyl, or a group $NR^{15}R^{16}$, —CONR$^{15}R^{16}$, —NR$^{15}$COR$^{16}$, —C($R^{15}$)=NOR$^{16}$, —NR$^{15}$SO$_2$R$^{16}$ or —SO$_2$NR$^{15}R^{16}$, wherein $R^{15}$ and $R^{16}$ independently represent hydrogen or $C_{1-6}$ alkyl or together form a heterocyclic ring;
X represents a bond, O, CO, SO$_2$, OCH$_2$ or CH$_2$O;
each $R^2$ and $R^4$ independently represents $C_{1-4}$ alkyl;
$R^3$ represents $C_{3-8}$ alkyl, $C_{3-6}$ alkenyl, $C_{3-6}$ alkynyl, $C_{3-6}$ cycloalkyl, $C_{5-6}$ cycloalkenyl or —$C_{1-4}$alkyl-$C_{3-6}$ cycloalkyl;
wherein said $C_{3-6}$ cycloalkyl groups of $R^3$ may be optionally substituted by one or more (eg. 1, 2 or 3) substituents which may be the same or different, and which are selected from the group consisting of halogen, $C_{1-4}$ alkyl or trifluoromethyl groups;
m and n independently represent 0, 1 or 2;
p and q independently represent 1 or 2;
or a pharmaceutically acceptable salt thereof.

DETAILED DESCRIPTION

In one particular aspect of the present invention, there is provided a compound of formula (I) as defined above wherein:

R¹ represents aryl, heteroaryl, -aryl-X-aryl, -aryl-X-heteroaryl, -aryl-X-heterocyclyl, -heteroaryl-X-heteroaryl, -heteroaryl-X-aryl or -heteroaryl-X-heterocyclyl; and wherein said aryl, heteroaryl and heterocyclyl groups of R¹ may be optionally substituted by one or more (eg. 1, 2 or 3) substituents which may be the same or different, and which are selected from the group consisting of halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, arylsulfonyl, arylsulfonyloxy, aryloxy, arylsulfonamido, arylcarboxamido, aroyl, or a group $NR^{15}R^{16}$, —$CONR^{15}R^{16}$, —$NR^{15}COR^{16}$, —$NR^{15}SO_2R^{16}$ or —$SO_2NR^{15}R^{16}$, wherein $R^{15}$ and $R^{16}$ independently represent hydrogen or $C_{1-6}$ alkyl or together form a heterocyclic ring; and q represents 1; and m represents 0.

In one particular aspect of the present invention, there is provided a compound of formula (I) as defined above wherein said aryl, heteroaryl and heterocyclyl groups of R¹ may be optionally substituted by one or more (eg. 1, 2 or 3) substituents which may be the same or different, and which are selected from the group consisting of halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, —$COC_{1-6}$ alkyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, arylsulfonyl, arylsulfonyloxy, aryloxy, arylsulfonamido, arylcarboxamido, aroyl, or a group $NR^{15}R^{16}$, —$CONR^{15}R^{16}$, —$NR^{15}COR^{16}$, —$C(R^{15})$=$NOR^{16}$, —$NR^{15}SO_2R^{16}$ or —$SO_2NR^{15}R^{16}$, wherein $R^{15}$ and $R^{16}$ independently represent hydrogen or $C_{1-6}$ alkyl or together form a heterocyclic ring.

Specific compounds of formula (I) which may be mentioned are those wherein R¹ represents pyridyl or pyrimidyl optionally substituted by one or two hydrogen, amino, halogen, cyano, $C_{1-6}$ alkyl or $C_{1-6}$ alkoxy groups and R³ represents $C_{3-8}$ alkyl, $C_{3-6}$ alkenyl, $C_{3-6}$ alkynyl, $C_{3-6}$ cycloalkyl or $C_{5-6}$ cycloalkenyl.

Specific compounds of formula (I) which may be mentioned are those wherein R¹ represents quinoxalinyl substituted by a halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, —$COC_{1-6}$ alkyl, —$COC_{1-6}$ alkyl-halogen, —$COC_{1-6}$ alkyl-cyano, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, aryl, arylsulfonyl, arylsulfonyloxy, aryloxy, arylsulfonamido, arylcarboxamido, aroyl, or a group $NR^{15}R^{16}$, —$NR^{15}COR^{16}$, —$C(R^{15})$=$NOR^{16}$, —$NR^{15}SO_2R^{16}$ or —$SO_2NR^{15}R^{16}$, wherein $R^{15}$ and $R^{16}$ independently represent hydrogen or $C_{1-6}$ alkyl or together form a heterocyclic ring.

Specific compounds of formula (I) which may be mentioned are those wherein R³ represents $C_{3-8}$ alkyl, $C_{3-6}$ alkenyl, $C_{3-6}$ alkynyl, $C_{3-6}$ cycloalkyl or $C_{5-6}$ cycloalkenyl.

Specific compounds of formula (I) which may be mentioned are those wherein R¹ represents quinolinyl or quinoxalinyl tri-substituted by a phenyl, amino and $C_{1-4}$ alkoxy group and R³ represents $C_{5-8}$ alkyl, $C_{3-6}$ alkenyl, $C_{3-6}$ alkynyl, $C_{3-6}$ cycloalkyl, $C_{5-6}$ cycloalkenyl or —$C_{1-4}$alkyl-$C_{3-8}$ cycloalkyl.

Alkyl groups, whether alone or as part of another group, may be straight chain or branched and the groups alkoxy and alkanoyl shall be interpreted similarly. The term 'halogen' is used herein to describe, unless otherwise stated, a group selected from fluorine, chlorine, bromine or iodine and the term 'polyhalo' is used herein to refer to a moiety containing more than one (eg. 2-5) of said halogen atoms.

The term "aryl" includes single and fused rings wherein at least one ring is aromatic, for example, phenyl, naphthyl, indanone and tetrahydronaphthalenyl.

The term "heterocyclyl" is intended to mean a 4-7 membered monocyclic saturated or partially unsaturated aliphatic ring containing 1 to 3 heteroatoms selected from oxygen, nitrogen or sulphur or a 4-7 membered saturated or partially unsaturated aliphatic ring fused to a benzene ring. Suitable examples of such monocyclic rings include pyrrolidinyl, azetidinyl, piperidinyl, piperazinyl, morpholinyl, tetrahydrofuranyl, tetrahydropyranyl, diazepanyl and azepanyl. Suitable examples of benzofused heterocyclic rings include indolinyl, isoindolinyl, 2,3,4,5-tetrahydro-1H-3-benzazepine, tetrahydroisoquinolinyl, dihydrobenzofuranyl or dihydrobenzoxazinyl.

The term "heteroaryl" is intended to mean a 5-6 membered monocyclic aromatic or a fused 8-10 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include benzofused aromatic rings such as quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

Preferably, R¹ represents

-aryl (eg. phenyl, naphthyl or indanone) optionally substituted by one or more (eg. 1, 2 or 3) halogen (eg. fluorine, chlorine or bromine), $C_{1-6}$ alkyl (eg. isopropyl), polyhalo$C_{1-6}$ alkyl (eg. $CF_3$), $C_{1-6}$ alkoxy (eg. methoxy or isopropyloxy), polyhalo$C_{1-6}$ alkoxy (eg. trifluoromethoxy or difluoromethoxy), —$COC_{1-6}$ alkyl (eg. —COMe or —COEt), —$C(R^{15})$=$NOR^{16}$ (eg. —C(Me)=NOMe or —C(Me)=NOEt), —$NR^{15}COR^{16}$ (eg. —NHCOMe), —$COC_{1-6}$ alkyl-halogen (eg. —$COCH_2$—F), —$COC_{1-6}$ alkyl-cyano (eg. —$COCH_2CN$), cyano or $C_{1-6}$ alkoxycarbonyl (eg. ethoxycarbonyl) groups;

-aryl-X-$C_{3-7}$cycloalkyl (eg. -phenyl-CO-cyclopropyl or -phenyl-CO-cyclobutyl);

-aryl-X-aryl (eg. -phenyl-CO-phenyl or -phenyl-O-phenyl);

-aryl-X-heterocyclyl (eg. -phenyl-CO-morpholinyl or -phenyl-pyrrolidinyl) optionally substituted by one or more (eg. 1, 2 or 3) halogen (eg, -2-chlorophenyl-CO-morpholinyl) or oxo groups;

-aryl-X-heteroaryl (eg. -phenyl-thiazolyl, -phenyl-oxadiazolyl (eg. -phenyl-1,2,4-oxadiazolyl or -phenyl-1,3,4-oxadiazolyl), -phenyl-pyrrolyl, -phenyl-oxazolyl or -phenyl-isoxazolyl) optionally substituted by a $C_{1-6}$ alkyl (eg. methyl) or aryl (eg. phenyl) group;

-heterocyclyl (eg. dihydrobenzofuranyl, dihydrobenzoxazinyl or indolinyl) optionally substituted by one or more (eg. 1, 2 or 3) $C_{1-6}$ alkyl (eg. methyl) or —COC$C_{1-6}$ alkyl (eg. —COMe) groups;

heteroaryl (eg. pyridyl, pyrimidyl, pyrazinyl, pyridazinyl, quinolinyl, isoquinolinyl or benzothiazolyl) optionally substituted by one or more (eg. 1, 2 or 3) cyano, halogen (eg. bromine or chlorine), polyhalo$C_{1-6}$ alkyl (eg. $CF_3$), $C_{1-6}$ alkyl (eg. methyl), $C_{1-6}$ alkoxy (eg. methoxy), $C_{1-6}$ alkoxycarbonyl (eg. methoxycarbonyl) or —CONR$^{15}$R$^{16}$ (eg. —CON(H)(Me) or —CON(Me)$_2$) groups;

-heteroaryl-X-aryl (eg. -pyrimidinyl-phenyl) optionally substituted by one or more (eg. 1, 2 or 3) cyano or $C_{1-6}$ alkylsulfonyl (eg. MeSO$_2$) groups;

-heteroaryl-X-heterocyclyl (eg. -pyrimidyl-morpholinyl, -pyrimidinyl-dihydrobenzofuranyl or -pyridyl-CO-pyrrolidinyl); or -heteroaryl-X-heteroaryl (eg. -pyrimidyl-pyridyl).

More preferably, R$^1$ represents

-aryl (eg. phenyl, naphthyl or indanone) optionally substituted by one or more (eg. 1, 2 or 3) halogen (eg. fluorine, chlorine or bromine), $C_{1-6}$ alkyl (eg. isopropyl), polyhalo$C_{1-6}$ alkyl (eg. $CF_3$), $C_{1-6}$ alkoxy (eg. methoxy or isopropyloxy), polyhalo$C_{1-6}$ alkoxy (eg. trifluoromethoxy or difluoromethoxy), —COC$_{1-6}$ alkyl (eg. —COMe or —COEt), —C(R$^{15}$)=NOR$^{16}$ (eg. —C(Me)=NOMe or —C(Me)=NOEt), —NR$^{15}$COR$^{16}$ (eg. —NHCOMe), —COC$_{1-6}$ alkyl-halogen (eg. —COCH$_2$—F), —COC$_{1-6}$ alkyl-cyano (eg. —COCH$_2$CN), cyano or $C_{1-6}$ alkoxycarbonyl (eg. ethoxycarbonyl) groups;

-aryl-X-$C_{3-7}$ cycloalkyl (eg. -phenyl-CO-cyclopropyl or -phenyl-CO-cyclobutyl);

-aryl-X-heteroaryl (eg. -phenyl-thiazolyl, -phenyl-oxadiazolyl, -phenyl-pyrrolyl, -phenyl-oxazolyl or -phenyl-isoxazolyl) optionally substituted by a $C_{1-6}$ alkyl (eg. methyl) or aryl (eg. phenyl) group; or -heteroaryl (eg. pyridyl, pyrimidyl, pyrazinyl, pyridazinyl, quinolinyl, isoquinolinyl or benzothiazolyl) optionally substituted by one or more (eg. 1, 2 or 3) cyano, halogen (eg. bromine or chlorine), polyhalo$C_{1-6}$ alkyl (eg. $CF_3$), $C_{1-6}$ alkyl (eg. methyl), $C_{1-6}$ alkoxy (eg. methoxy), $C_{1-6}$ alkoxycarbonyl (eg. methoxycarbonyl) or —CONR$^{15}$R$^{16}$ (eg. —CON(H)(Me) or —CON(Me)$_2$) groups.

Most preferably, R$^1$ represents

-aryl (eg. phenyl) optionally substituted by one or more (eg. 1, 2 or 3) halogen (eg. fluorine or chlorine), polyhalo$C_{1-6}$ alkyl (eg. $CF_3$), —NR$^{15}$COR$^{16}$ (eg. —NHCOMe), —COC$_{1-6}$ alkyl (eg. —COMe or —COEt) or cyano groups;

-aryl-X-$C_{3-7}$ cycloalkyl (eg. -phenyl-CO-cyclopropyl);

-aryl-X-heteroaryl (eg. -phenyl-oxadiazolyl or -phenyl-oxazolyl) optionally substituted by a $C_{1-6}$ alkyl (eg. methyl) or aryl (eg. phenyl) group; or -heteroaryl (eg. pyridyl, pyrimidyl, pyrazinyl, pyridazinyl or quinolinyl) optionally substituted by one or more (eg. 1, 2 or 3) halogen (eg. bromine or chlorine), polyhalo$C_{1-6}$ alkyl (eg. $CF_3$), $C_{1-6}$ alkyl (eg. methyl) or cyano groups.

Especially preferably, R$^1$ represents

-aryl (eg. phenyl) optionally substituted at the 4-position by a —COC$_{1-6}$ alkyl (eg. —COMe or —COEt) or cyano group; or -heteroaryl (eg. pyridyl or quinolinyl) optionally substituted by one or more (eg. 1, 2 or 3) $C_{1-6}$ alkyl (eg. methyl) or polyhalo$C_{1-6}$ alkyl (eg. $CF_3$) groups.

Most especially preferably, R$^1$ represents

-pyridyl (eg. -3-pyridyl) substituted at the 6-position by a polyhalo$C_{1-6}$ alkyl (eg. $CF_3$) group (eg. 6-$CF_3$-pyridin-3-yl).

Preferably X represents a bond, O or CO, more preferably a bond or CO, most preferably a bond.

Preferably, m represents 0.

Preferably, n represents 0, 1 or 2, more preferably 0 or 1, especially 0.

Preferably, q represents 1.

When present, preferably R$^2$ represents methyl.

When R$^2$ represents methyl, said R$^2$ group is preferably attached to the carbon atom adjacent to the N—R$^3$ group. When R$^2$ represents methyl, the stereochemistry of R$^2$ preferably has the S configuration.

Preferably, R$^3$ represents $C_{3-8}$ alkyl (eg. ethyl, isopropyl, n-propyl, isobutyl or isopentyl) or $C_{3-6}$ cycloalkyl (eg. cyclobutyl or cyclopentyl), more preferably isopropyl, isobutyl or cyclobutyl, most preferably isopropyl or cyclobutyl, especially isopropyl.

Preferred compounds according to the invention include examples E1-E198 as shown below, or a pharmaceutically acceptable salt thereof.

More preferred compounds according to the invention include:

1-Isopropyl-4-[1-(5-cyano-pyridin-2-yl)-piperidine-4-carbonyl]-piperazine (E1);

1-Isopropyl-4-[1-(5-methoxycarbonyl-4-trifluoromethylpyridin-2-yl)-piperidine-4-carbonyl]-piperazine (E4);1-Isopropyl-4-[1-(4ethoxycarbonylphenyl)-piperidine-4-carbonyl]-piperazine (E8); 1-Cyclobutyl-4-[1-(4-cyanophenyl)-piperidine-4-carbonyl]-piperazine (E9); 1-Cyclobutyl-4-[1-(4-cyano-3-fluorophenyl)-piperidine-4-carbonyl]-piperazine (E10); 1-Cyclobutyl4-[1-(4-cyano-2,6-difluorophenyl)-piperidine-4-carbonyl]-piperazine (E11); 1-Cyclobutyl-4-[1-(4-cyano-3-trifluoromethylphenyl)-piperidine-4-carbonyl]-piperazine (E12); 1-Cyclobutyl-4-[1-(4-cyano-naphthalen-1 -yl)-piperidine-4-carbonyl]-piperazine (E13); 1-Cyclobutyl-4-[1-(5-cyanopyridin-2-yl)-piperidine-4-carbonyl]-piperazine (E14); 1-Cyclobutyl-4-[1-(6-trifluoromethylpyridin-2-yl)-piperidine-4-carbonyl]-piperazine (E15); 1-Cyclobutyl-4-[1-(5-trifluoromethylpyridin-2-yl)-piperidine-4-carbonyl]-piperazine (E16); 1-Cyclobutyl-4-[1-(3-chloro-5-trifluoromethylpyridin-2-yl)-piperidine-4-carbonyl]-piperazine (E17); 1-Isopropyl-4-{1-[5-(4-methylsulfonylphenyl)-pyrimidin-2-yl]-piperidine-4-carbonyl}-piperazine (E25);1-Isopropyl-4-{1-[4-(morpholino-carbonyl)-phenyl]-piperidine-4-carbonyl}-piperazine (E30);

1-Cyclopentyl-4-[1-(4-cyano-phenyl)-piperidine4-carbonyl]-piperazine (E31);

(2R,6S)-1-Cyclobutyl-4-[1-(4-cyanophenyl)-piperidine-4-carbonyl]-2,6-dimethylpiperazine (E33);

1-Isopentyl4-[1-(5-cyano-pyridin-2-ylpiperidine-4-carbonyl]-piperazine (E35);

1-Cyclobutyl-4-[1-(4-cyanophenyl)-piperidine4-carbonyl]-[1,4]-diazepane (E36);

1-Cyclobutyl-4-[1-(5-cyanopyridin-2-yl)-piperidine4-carbonyl]-[1,4]-diazepane (E37);

1-Isopropyl-4-[1-(4-cyano-2,5-difluorophenyl)-piperidine-4-carbonyl]-[1,4]-diazepane (E39);

1-Isopropyl-4-[1-(4-cyano-3-chlorophenyl)-piperidine-4-carbonyl]-[1,4]-diazepane (E40);

1-Isopropyl-4-[1-(4-cyano-3-fluoro-phenyl)-piperidine4-carbonyl]-[1,4]-diazepane (E41);

1-Isopropyl-4-[1-(4-cyano-2,6-difluoro-phenyl)-piperidine-4-carbonyl]-[1,4]-diazepane (E42);
1-Isopropyl-4-[1-(4-cyano-2-fluoro-phenyl)-piperidine-4-carbonyl]-[1,4]-diazepane (E43);
1-Isopropyl4-[1-(4-cyano-3-trifluoromethyl-phenyl)-piperidine-4-carbonyl]-[1,4]-diazepane (E44);
1-Isopropyl-4-[1-(4-trifluoromethyl-phenyl)-piperidine-4-carbonyl]-[1,4]-diazepane (E45);
1-Isopropyl-4-[1-(4-cyano-naphthalen-1-yl)-piperidine-4-carbonyl]-[1,4]-diazepane (E46);
1-Isopropyl-4-[1-(3,4-dichlorophenyl)-piperidine-4-carbonyl]-[1,4]-diazepane (E54);
1-Isopropyl-4-[1-(4-trifluoromethoxyphenyl)-piperidine4-carbonyl]-[1,4]-diazepane (E56);
1-Isopropyl-4-[1-(4-difluoromethoxyphenyl)-piperidine-4-carbonyl]-[1,4]-diazepane (E59);
1-Isopropyl-4-[1-(4-phenoxyphenyl)-piperidine-4-carbonyl]-[1,4]-diazepane (E61);
1-Isopropyl-4-[1-(6-methoxypyridin-3-yl)-piperidine-4-carbonyl]-[1,4]-diazepane (E62);1-Isopropyl-4-[1-(4-cyano-2,3-difluorophenyl)-piperidine-4-carbonyl]-[1,4]-diazepane (E63);
1-Isopropyl-4-[1-(4-cyano-2-chlorophenyl)-piperidine-4-carbonyl]-[1,4]-diazepane (E64);
1-Cyclobutyl-4-[1-(4-cyano-2-chlorophenyl)-piperidine-4-carbonyl]-[1,4]-diazepane (E65);
1-Cyclobutyl-4-[1-(4-cyano-3-chlorophenyl)-piperidine4-carbonyl]-[1,4]-diazepane (E66);
1-Cyclobutyl-4-[1-(4-cyano-3-fluorophenyl)-piperidine4-carbonyl]-[1,4]-diazepane (E67);
1-Cyclobutyl-4-[1-(4-cyano-3-trifluoromethylphenyl)-piperidine4-carbonyl]-[1,4]-diazepane (E68);
1-Cyclobutyl-4-[1-(4-cyano-2,5-difluorophenyl)-piperidinecarbonyl]-[1,4]-diazepane (E69);
(S)-1-Isopropyl-4-[1-(4-cyanophenyl)-piperidine-4-carbonyl]-2-methylpiperazine (E70);
(S)-1-Isopropyl-4-[1-(6-cyanopyridin-3-yl)-piperidine-4-carbonyl]-2-methyl piperazine (E78);
(S)-1-Isopropyl-4-[1-(5-cyanopyridin-2-yl)-piperidine4-carbonyl]-2-methyl piperazine (E86);
(S)-1-Isopropyl-4-[1-(5-trifluoromethyl-pyrazin-2-yl)-piperidine4-carbonyl]-2-methyl piperazine (E87);
(S)-1-Isopropyl-4-[1-(6-trifluoromethyl-pyridazin-3-yl)-piperidine-4-carbonyl]-2-methyl piperazine (E88);
1-Isopropyl-4-{1-[4-(5-phenyl-1,3,4-oxadiazol-2-yl)phenyl]-piperidine-4-carbonyl} piperazine (E90);
1-Isopropyl-4-[1-(quinolin-6-yl)-piperidine4-carbonyl]piperazine (E91);
1-Cyclobutyl-4-[1-(6-trifluoromethylpyridin-3-yl)-piperidine-4-carbonyl]piperazine (E97);
1-Isopropyl-4-[1-(5-trifluoromethyl-pyrazin-2-yl)-piperidine4-carbonyl]-piperazine (E102);
(S)-1-Isobutyl-4-[1-(4-cyanophenyl)-piperidine-4-carbonyl]-piperazine (E104);
1-Isopropyl-4-[1-(4-cyclopropylcarbonylphenyl)-piperidine4-carbonyl]-piperazine (E105);
1-Isopropyl-4-[1-(2-methyl-quinolin-6-yl)-piperidine-4-carbonyl]-piperazine (E118);
1-Isopropyl-4-[1-(6-cyano-pyridin-3-yl)-piperidine-4-carbonyl]-piperazine (E129);
1-Cyclobutyl-4-[1-(6-trifluoromethylpyridin-3-yl)-piperidine4-carbonyl]-[1,4]-diazepane (E136);
1-Cyclobutyl-4-[1-(2-cyanopyridin-4-yl)-piperidine-4-carbonyl]-[1,4]-diazepane (E137);
1-Isopropyl-4-[1-(6-trifluoromethylpyridazin-3-yl)-piperidine-4-carbonyl]-[1,4]-diazepane (E138);
1-Isopropyl-4-[1-(5-trifluoromethylpyrazin-2-yl)-piperidine4-carbonyl]-[1,4]-diazepane (E139);
1-Isopropyl-4-{1-[4-(2-methyl-1,3-oxazol-5-yl)phenyl]-piperidine4-carbonyl}-[1,4]-diazepane (E154);
1-Isopropyl-4-{1-[4-(3-methyl-1,2,4-oxadiazol-5-yl)phenyl]-piperidine-4-carbonyl}-[1,4]-diazepane (E168);
1-Isopropyl-4-[1-(4-acetamido-3-fluorophenyl)-piperidine4-carbonyl]-[1,4]-diazepane (E169);
1-Cyclobutyl-4-[1-(4-acetylphenyl)-piperidine-4-carbonyl]-[1,4]-diazepane (E170);
1-Cyclobutyl-4-[1-(6-cyano-pyridin-3-yl)-piperidine-4-carbonyl]-[1,4]-diazepane (E179);
1-Isopropyl-4-[1-(6-cyano-pyridin-3-yl)-piperidine-4-carbonyl]-[1,4]-diazepane (E180);
1-Isopropyl-4-[1-(2-methyl-quinolin-4-yl)-piperidine-4-carbonyl]-[1,4]-diazepane (E183);
1-Isopropyl-4-{1-[4-(3-methyl-1,2,4-oxadiazol-5-yl)phenyl]-piperidine-4-carbonyl}-piperazine (E185);
1-Isopropyl-4-[1-(2-trifluoromethylpyrimidin-5-yl)-piperidine-4-carbonyl]-[1,4]-diazepane (E198)

or a pharmaceutically acceptable salt thereof.

Most preferred compounds according to the invention include:
1-Isopropyl-4-[1-(4-cyanophenyl)-piperidine-4-carbonyl]-piperazine (E2);
1-Isopropyl-4-[1-(4-cyanophenyl)-piperidine4-carbonyl]-[1,4]-diazepane (E38);
(S)-1-Isopropyl-4-[1-(6-trifluoromethylpyridin-3-yl)-piperidine-4-carbonyl]-2-methyl piperazine (E79);
1-Isopropyl-4-[1-(4-acetylphenyl)-piperidine-4-carbonyl]-[1,4]-diazepane (E150);
1-Isopropyl-4-[1-(4-propanoylphenyl)-piperidine-4-carbonyl]-[1,4]-diazepane (E151);

or a pharmaceutically acceptable salt thereof.

Especially preferred compounds according to the invention include:
1-Isopropyl-4-[1-(6-trifluoromethylpyridin-3-yl)-piperidine-4-carbonyl]-piperazine (E96);
1-Isopropyl-4-[1-(6-trifluoromethylpyridin-3-yl)-pipenidine-4-carbonyl]-[1,4]-diazepane (E135);

or a pharmaceutically acceptable salt thereof.

Because of their potential use in medicine, the salts of the compounds of formula (I) are preferably pharmaceutically acceptable.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalesulfonate) or hexanoate salt.

The invention includes within its scope all possible stoichiometric and non-stoichiometric forms of the salts of the compounds of formula (I) including hydrates and solvates.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The present invention also provides a process for the preparation of a compound of formula (I) or a pharmaceutically acceptable salt thereof, which process comprises:

(a) reacting a compound of formula (II)

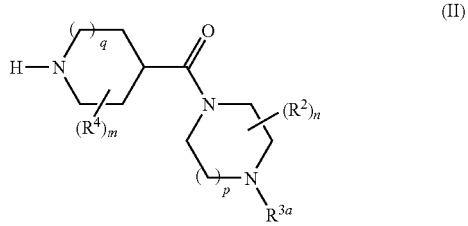

or an optionally activated or protected derivative thereof, wherein $R^2$, $R^4$, m, n, p and q are as defined above and $R^{3a}$ is as defined for $R^3$ above or a group convertible to $R^3$, with a compound of formula $R^1$-$L^1$, wherein $R^1$ is as defined above and $L^1$ represents a suitable leaving group, such as a halogen atom (eg. fluorine, chlorine, bromine or iodine) or triflate, followed by a deprotection reaction as necessary; or (b) reacting a compound of formula (III)

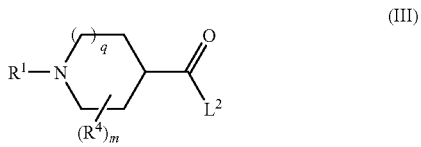

wherein $R^1$, $R^4$, m and q are as defined above and $L^2$ represents OH or a suitable leaving group, such as a halogen atom (eg. chlorine), with a compound of formula (IV)

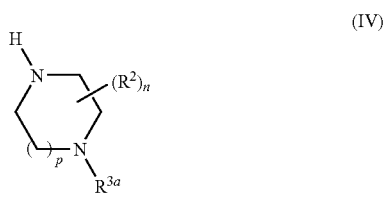

wherein $R^2$, n and p are as defined above $R^{3a}$ is as defined for $R^3$ above or a group convertible to $R^3$; or (c) deprotecting a compound of formula (I) or converting groups which are protected; and optionally thereafter (d) interconversion to other compounds of formula (I).

Process (a) typically comprises the use of a suitable base, such as potassium carbonate in a suitable solvent such as dimethylsulfoxide or N,N-dimethylformamide at elevated temperature. Alternatively process (a) may be carried out with a suitable catalyst such as tris(dibenzylideneacetone)dipalladium(0) and 2-dicyclohexylphosphino-2'-(N,N-dimethylamino)biphenyl or bis(dibenzylideneacetone)palladium and 2-dicyclohexylphosphino-2'-(N,N-dimethylamino)biphenyl or acetato(2'-di-t-butylphosphin-1,1'-biphenyl-2-yl)palladium II in the presence of a suitable base such as sodium t-butoxide or potassium phosphate in a solvent such as o-xylene, dioxane or toluene, optionally at an elevated temperature.

An $R^{3a}$ group convertible to $R^3$ may for example be a protecting group such as tert-butoxycarbonyl which may be removed under acidic conditions, eg trifluoroacetic acid or HCl or a benzyloxycarbonyl group which may be removed by hydrogenolysis, to give a compound where $R^3$ represents hydrogen. Subsequent conversion to a compound where $R^{3a}$ represents $R^3$ may be carried out by reductive amination with a compound of formula $R^3$=O in the presence of sodium triacetoxyborohydride or alkylation with a compound of formula $R^3$—$L^3$ where $L^3$ is a leaving group such as bromine or iodine. When $R^2$ represents methyl at the carbon atom adjacent to N—$R^{3a}$, $R^{3a}$ may represent hydrogen which may subsequently be converted to $R^3$ as described above.

Process (b) typically comprises activation of the compound of formula (III) wherein $L^2$ represents OH with a coupling reagent such as 1-(3-dimethylaminopropyl)-3-ethylcarbodiimide hydrochloride (EDC) in the presence of 1-hydroxybenzotriazole (HOBT) or 1-hydroxyazabenzotriazole (HOAT) in a suitable solvent such as dichloromethane or dimethylformamide followed by reaction with the compound of formula (IV).

Process (b) may also involve halogenation of the compound of formula (III) wherein $L^2$ represents OH with a suitable halogenating agent (eg. thionyl chloride or oxalyl chloride) followed by reaction with the compound of formula (IV) in the presence of a suitable base such as triethylamine or a solid supported base such as diethylaminomethylpolystyrene in a suitable solvent such as dichloromethane In process (c), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (d) may be performed using conventional interconversion procedures such as epimerisation, oxidation, reduction, alkylation, nucleophilic or electrophilic aromatic substitution, ester hydrolysis or amide bond formation. Examples of transition metal mediated coupling reactions useful as interconversion procedures include the following: Palladium catalysed coupling reactions between organic electrophiles, such as aryl halides, and organometallic reagents, for example boronic acids (Suzuki cross-coupling reactions); Palladium catalysed amination and amidation reactions between organic electrophiles, such as aryl halides, and nucleophiles, such as amines and amides; Copper catalysed amidabon reactions between organic electrophiles (such as aryl halides) and nucleophiles such as amides; and Copper mediated coupling reactions between phenols and boronic acids.

Compounds of formula (II) may be prepared in accordance with the following procedure:

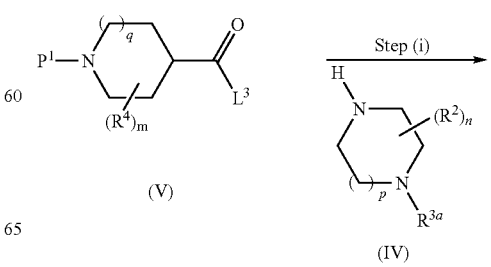

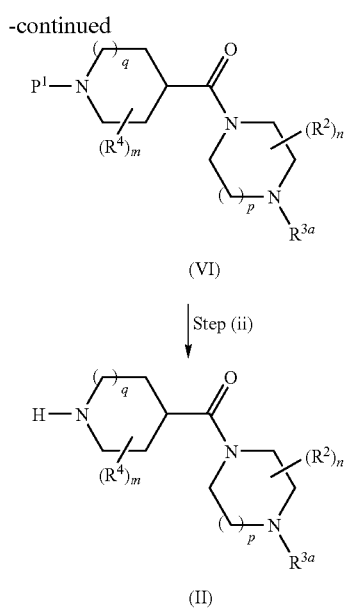

(VI)

↓ Step (ii)

(II)

wherein $R^2$, $R^4$, m, n, p and q are as defined above, $R^{3a}$ is as defined for $R^3$ above or a group convertible to $R^3$, $L^3$ represents OH or a suitable leaving group such as a halogen atom (eg. chlorine), and $P^1$ represents a suitable protecting group such as t-butoxycarbonyl.

When $L^3$ represents OH, step (i) typically comprises the use of suitable coupling conditions eg 1-(3-dimethylaminopropyl)-3-ethylcarbodiimide hydrochloride (EDC) in the presence of 1-hydroxybenzotriazole (HOBT) or 1-hydroxy-7-azabenzotriazole (HOAT).

When $L^3$ represents a suitable leaving group such as a halogen atom (eg. chlorine), step (i) typically comprises the use of a suitable base such as triethylamine in a suitable solvent such as dichloromethane.

Step (ii) typically comprises a suitable deprotection reaction using standard conditions such as those described above for process (c). Where $P^1$ is a tert butoxycarbonyl group this may involve a suitable acid such as HCl or trifluoroacetic acid Compounds of formula (III) wherein $L^2$ represents OH, may be prepared in accordance with the following procedure:

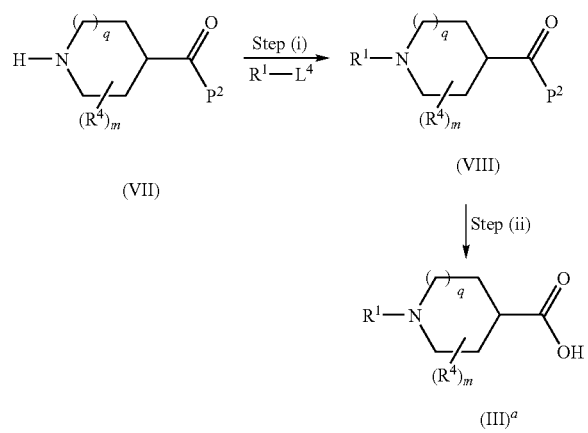

wherein $R^1$, $R^4$, m and q are as defined above, $L^4$ represents a suitable leaving group such as a halogen atom or triflate and $P^2$ represents a suitable protecting group such as methoxy, ethoxy, t-butoxy or benzyloxy.

Step (i) is typically carried out in a suitable solvent such as N,N-dimethylformamide or dimethylsulfoxide in the presence of a base such as potassium carbonate. Alternatively step (i) may be carried out with a suitable catalyst such as tris(dibenzylideneacetone)dipalladium(0) and 2-dicyclohexylphosphino-2'-(N,N-dimethylamino)biphenyl or bis(dibenzylideneacetone)palladium and 2-dicyclohexylphosphino-2'-(N,N-dimethylamino)biphenyl or acetato(2'-di-t-butylphosphin-1,1'-biphenyl-2-yl)palladium II in the presence of a suitable base such as sodium t-butoxide or potassium phosphate in a solvent such as o-xylene, dioxane or toluene, optionally at an elevated temperature.

Step (ii) typically comprises a suitable deprotection reaction using standard conditions such as those described above for process (c). Where $P^2$ is an alkoxy group such as ethoxy this may involve suitable acid or base catalysed hydrolysis eg. using aqueous hydrochloric acid or a base such as sodium hydroxide or lithium hydroxide.

Compounds of formula (III) wherein $L^2$ represents a suitable leaving group, such as a halogen atom (eg. chlorine) may be prepared by treating a compound of formula $(III)^a$ with thionyl chloride or oxalyl chloride.

Compounds of formula (IV), (V), (VII) and $R^1$-$L^4$ are either known in the literature or can be prepared by analogous methods.

Compounds of formula (I) and their pharmaceutically acceptable salts have affinity for and are antagonists and/or inverse agonists of the histamine H3 receptor and are believed to be of potential use in the treatment of neurological diseases including Alzheimer's disease, dementia, age-related memory dysfunction, mild cognitive impairment, cognitive deficit, epilepsy, neuropathic pain, inflammatory pain, migraine, Parkinson's disease, multiple sclerosis, stroke and sleep disorders including narcolepsy; psychiatric disorders including schizophrenia (particularly cognitive deficit of schizophrenia), attention deficit hyperactivity disorder, depression and addiction; and other diseases including obesity, asthma, allergic rhinitis, nasal congestion, chronic obstructive pulmonary disease and gastrointestinal disorders.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

Compounds of formula (I) may be used in combination with other therapeutic agents, for example medicaments claimed to be useful as either disease modifying or symptomatic treatments of Alzheimer's disease. Suitable examples of such other therapeutic agents may be agents known to modify cholinergic transmission such as 5-$HT_5$ antagonists, M1 muscarinic agonists, M2 muscarinic antagonists or acetylcholinesterase inhibitors. Compounds of formula (I) may also be used in combination with histamine H1 antagonists, such a combination has the potential to be useful in the treatment of various respiratory disorders, such as asthma, allergic rhinitis, nasal congestion or chronic obstructive pulmonary disease. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Descriptions and Examples illustrate the preparation of compounds of the invention.

It will be appreciated that any of the following hydrochloride salt compounds may be converted into the corresponding free base compounds by treatment with saturated aqueous potassium carbonate solution followed by extraction into DCM using the procedure described in Description 8, step 4.

It will also be appreciated that '1,4-Diazepane' is used throughout to refer to the ring system below which may also be referred to as 'hexahydro-1H-1,4diazepine'.

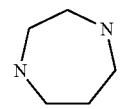

Description 1

1-Isopropyl-4-(piperidine-4-carbonyl)-piperazine
(D1)

Step 1:
1-Isopropyl-4-(piperidine-4-carbonyl)-piperazine dihydrochloride 1-tert-Butoxycarbonyl-piperidine-4-carboxylate (5 g) in DMF (60 ml) was treated with EDC (5.5 g) followed by HOAT (0.1 g). After 5 min, N-isopropylpiperazine (2.8 g) in DMF (5 ml) was added and the reaction was left stirring for 18 h. The reaction was then diluted with EtOAc (150 ml) and washed with saturated brine/sodium hydrogen carbonate (1:1, 200 ml) followed by brine (3×200 ml). The EtOAc layer was evaporated to near dryness and the residue treated with TFA/water (40 ml, 95:5) for 5 h prior to evaporation and re-evaporation from toluene (3×60 ml). The residue was taken up into a minimum volume of EtOAc and treated with HCl (30 ml, 2N solution in diethyl ether) for 1 h. The resulting sub-titled compound was filtered off and washed with diethyl ether before drying under vacuum (4.8 g).

Step 2:
1-Isopropyl-4-(piperidine-4-carbonyl)-piperazine

The product of D1, Step 1, was dissolved in water and basified with potassium carbonate, followed by extraction with EtOAc and evaporation gave the title compound (D1) as the free base (3.5 g). $^1$H NMR δ [MeOH-d4]: 1.073 (6H, d, J=6.4 Hz), 1.69-1.75 (4H, m), 2.5-2.58 (4H, m), 2.69-2.82 (3H, m), 2.85-2.94 (1H, m), 3.13-3.22 (2H, m) and 3.54-3.65 (4H, m).

Description 2

1-Isopropyl-4-[1-(5-bromno-pyrimidin-2-yl)-piperidine-4-carbonyl]-piperazine (D2)

Potassium carbonate (2.06 g) was added to a mixture of 5-bromo-2-chloropyrimidine (2.89 g) and 1-isopropyl-4-(piperidine-4-carbonyl)-piperazine (D1)(3.57 g) in DMF (60 ml). The reaction mixture was allowed to stir at rt overnight. The DMF was removed by evaporation and the resulting residue was partitioned between $H_2O$/EtOAc(20:20 ml). The EtOAc layer was dried ($MgSO_4$) and filtered, the filtrate was evaporated to dryness to give the title compound (D2) as a white solid (4 g). $^1$H NMR δ [DMSO-d6]: 0.98 (6H, d, J=6.5), 1.4-1.5 (2H, m), 1.6-1.7 (2H, m), 2.30-2.35 (2H, m), 2.40-2.48 (2H, m), 2.64-2.70 (1H, m) 2.93-3.00 (3H, m), 3.4-3.55 (4H, m) 4.52-4.59 (2H, m) 8.45 (2H, s).

Description 3

1-(4-Cyanophenyl)-piperidine-4-carboxylic acid (D3)

Step 1: Ethyl
1-(4-cyanophenyl)-piperidine-4-carboxylate

To 4-fluorobenzonitrile (11.56 g) in DMSO (200 ml) was added piperidine-4carboxylic acid ethyl ester (15 g) and potassium carbonate (14.4 g) and the reaction was heated to 120° C. for 4 h. After cooling solvent was evaporated and the residue taken up into EtOAc (150 ml) and washed with HCl (1M, 2×100 ml), sodium hydrogen carbonate solution (2×100 ml) and brine (100ml). Evaporation of the organic layer provided the subtitled compound (22.6 g). LCMS electrospray (+ve) 259 ($MH^+$).

Step 2: 1-(4-Cyanophenyl)-piperidine-4-carboxylic acid

The product of D3, Step 1 (22.6 g) was dissolved in 1,4-dioxane (150 ml) and 2M sodium hydroxide (87 ml). The reaction was then stirred at rt for 2 h and then further 2M sodium hydroxide (87 ml) was added and the reaction heated to 70° C. for 2 h. The reaction mixture was then evaporated and the residue acidified to pH-2 with aqueous 2N HCl. The aqueous solution was then extracted with DCM (2×200 ml) and the combined organic layers washed with brine (100 ml), dried ($MgSO_4$) and evaporated to give the title compound (D3) as a white solid (14.8 g). LCMS electrospray(+ve) 231 ($MH^+$).

Description 4

1-[1-(4-Cyanophenyl)-piperidine-4-carbonyl]-[1,4]-diazepane hydrochloride (D4)

Step 1: 1-tert-Butoxycarbonyl-4-[1-(4-cyanophenyl)-piperidine-4-carbonyl]-[1,4]diazepane 1-(4-Cyanophenyl)-piperidine-4carboxylic acid (D3) (3.94 g), HOBT (1.01 g), TEA (2.7 ml) and 1-tert-butoxycarbonyl-1,4-diazepane (3.0 g) were stirred in DMF (25 ml) and then EDC (3.7 g) was added and the reaction stirred at rt overnight. The solvent was evaporated and the residue re-dissolved in DCM (100 ml) and washed with saturated sodium hydrogen carbonate (2×80 ml), brine (75 ml) and the organic layer dried ($MgSO_4$) and evaporated. The crude product was then purified by column chromatography [silica gel, step gradient 0-10% MeOH in DCM]. Fractions containing the required product were evaporated to give the subtitled compound as a white solid (0.92 g). LCMS electrospray(+ve) 413 ($MH^+$).

Step 2: 1-[1-(4-Cyanophenyl)-piperldine-4-carbonyl]-[1,4]diazepane hydrochloride The product of D4, Step 1 (0.92 g) was dissolved in DCM (25 ml) and 4N HCl in 1,4-dioxane (5 ml) was added and the reaction stirred at rt for 2 h. The solvent was then evaporated to give the title compound (D4) as a white solid (0.77 g). LCMS electrospray(+ve) 313 ($MH^+$).

Description 5

1-Cyclopentyl-4-(piperidine-4-carbonyl)-piperazine di-hydrochloride (D5)

Step 1: 1-Cyclopentyl-4-[1-tert-butoxycarbonyl-piperidine-4-carbonyl]-piperazine 1-tert-Butoxycarbonyl-piperidine-4-carboxylic acid (2.2 g) in dry DMF (40 ml) was treated with EDC (3.71 g) followed by HOAT (0.1 g). After 5 min, N-cyclopentylpiperazine (1.5 g) in dry DMF (5 ml) was added and the reaction mixture was stirred at rt for 18 h. Excess DMF was removed by evaporation and the resulting residue was re-dissolved in DCM, adsorbed onto silica gel (10 g) and purified by chromatography [silica gel 0-10% MeOH (containing 10% 0.88 ammonia solution/DCM)]. The pure fractions were combined and the solvent removed by evaporation to give the subtitled compound (2 g). LCMS electrospray(+ve) 366($MH^+$).

Step 2:
1-Cyclopentyl-4-(piperldine-4-carbonyl)-piperazine di-hydrochloride

The product of D5, Step 1 (2 g) was dissolved in dry MeOH (30 ml) and treated with 4N dioxan/HCl (5 ml). The reaction mixture was stirred at rt for 18 h. Excess solvent was removed by evaporation to give the title compound (D5) as a cream solid (2 g). LCMS electrospray (+ve) 266(MH$^+$).

Description 6

1-Cyclobutyl-piperazine di-hydrochloride (D6)

Step 1:
1-tert-Butoxycarbonyl-4-cyclobutyl-piperazine 1-tert-Butoxycarbonyl-piperazine (5.6 g) was dissolved in dry DCM (100 ml) followed by the addition of cyclobutanone (2.10 g). The reaction mixture was stirred at rt for 30 min. Sodium triacetoxyborohydride (6.37 g) was added portionwise over 15 min. The mixture was then stirred at rt overnight to give a black solution. The reaction mixture was washed with 1N NaOH (70 ml) and the DCM layer was separated, dried (MgSO$_4$) and filtered. The filtrate was evaporated to dryness to give the subtitled compound as an oil (6.1 g) $^1$H NMR δ [DMSO-d6]: 1.39 (6H, s), 1.68-1.87 (4H, m), 1.9-2.01 (2H, m), 2.15-2.2 (3H, m), 2.5 (1H, m), 2.6-2.78 (1H, m), 3.18-3.3 (4H, m).

Step 2: 1-Cyclobutyl-piperazine di-hydrochloride

The product of D6, Step 1 (5.1 g) was dissolved in dry MeOH (150 ml) followed by the addition of 4N HCl in dioxan (10 ml). The reaction mixture was stirred at rt overnight before being evaporated to dryness to give the title compound as a white solid (D6)(4 g).

Description 7

1-Cyclobutyl-4-(piperidine carbonyl)-piperazine di-hydrochloride (D7)

1-Cyclobutyl-piperazine di-hydrochloride (D6)(1.8 g) in DMF (15 ml) was stirred with sodium hydrogen carbonate (1.53 g) for 5 min before being added to a DMF (15 ml) solution of 1-tert-butoxycarbonyl-piperidine-4-carboxylic acid (1.94 g), EDCl (3.2 g) and HOAT (0.05 g). After 4 h the reaction was diluted with EtOAc and washed with saturated sodium hydrogen carbonate solution and brine (3×), before being evaporated. The residue was dissolved in a small volume of EtOAc and treated with TFA (90% TFA/water). After 2 h toluene was added and the reaction evaporated and re-evaporated from toluene. The residue was taken up into EtOAc and treated with 2N HCl in diethyl ether. The precipitate was filtered, washed with diethyl ether and dried under vacuum. Crystallisation from ethanol/diethyl ether afforded the title compound (D7)(1.74 g). LCMS electrospray (+ve) 252(MH$^+$).

Description 8

1-Isopropyl-4-(piperidine-4-carbonyl)-[1,4]-diazepane (D8)

Step 1: 1-Benzyl-4-(1-tert-butoxycarbonyl-piperidine-4-carbonyl)-[1,4]-diazepane 1-Benzyl-[1,4]-diazepane (3.78 g) and 1-tert-butoxycarbonyl-piperidine-4-carboxylic acid (5.0 g) were dissolved in DCM (150 ml) and TEA (3.6 ml) was added followed by HOBT (1.34 g) and finally EDC (4.90 g). The reaction was stirred at rt overnight. The reaction mixture was then evaporated to a minimum, re-dissolved in DCM (50 ml) and washed with saturated sodium hydrogen carbonate solution (3×50 ml) and brine (50 ml). The organic layer was dried (MgSO$_4$) and evaporated to a crude which was purified by column chromatography [silica gel, step gradient 0-10% MeOH (containing 10% 0.880 ammonia solution) in DCM]. Fractions containing pure desired product were combined and evaporated to give the subtitled compound as a pale brown solid (7.1 g).

Step 2: 1-(1-tert-Butoxycarbonyl-piperidine-4-carbonyl)-[1,4]-diazepane

The product of D8, Step 1 (7.1 g) was dissolved in ethanol (100 ml) and 10% palladium on charcoal (1.0 g) was added and the reaction hydrogenated for 18 h. The catalyst was then removed by filtration and the filtrate evaporated to give the subtitled compound as a clear oil (5.0 g).

Step 3: 1-Isopropyl-4-(1-tert-butoxycarbonyl-piperidine-4-carbonyl)-[1,4]-diazepane The product of D8, Step 2 (2.0 g) was dissolved in DCM (50 ml) and acetone (0.94 ml) added and the mixture stirred for 5 min. Sodium triacetoxyborohydride (2.7 g) was then added and the reaction stirred at rt for 1.5 h. The reaction mixture was then washed with saturated potassium carbonate solution (50 ml), sodium hydrogen carbonate solution (3×50 ml) and brine (50 ml). The organic layer was dried (MgSO$_4$) and evaporated to give the subtitled compound as a white solid (1.50 g).

Step 4: 1-Isopropyl-4-(piperidine-4-carbonyl]-[1,4]-diazepane

The product of D8, Step 3 (1.5 g) was dissolved in methanol (30 ml) and 4N HCl in dioxane (10 ml) added. The reaction was stirred at rt for 16 h. The reaction mixture was then evaporated to a minimum and the residue basified with saturated potassium carbonate solution (50 ml) and extracted with DCM (3×50 ml). The organic layer was dried (MgSO$_4$) and evaporated to give the title compound (D8) as a white solid (0.75 g). MS electrospray (+ve) 254 (MH$^+$).

Description 9

1-Isopropyl-4-[1-(4-carboxy-phenyl)-piperldin-4-carbonyl]-piperazine hydrochloride (D9)

Step 1: 1-Isopropyl-4-[1-(4-ethoxycarbonyl-phenyl)-piperldin-4-carbonyl]-piperazine 1-Isopropyl4-(piperidine-4-carbonyl)piperazine (D1)(2.5 g), ethyl 4-fluorobenzoate (1.39 g) and potassium carbonate (3.55 g) was stirred in DMSO (50 ml) and heated to 120° C. for 2 h. The reaction was then heated to 140° C. for a further 2 h. The reaction was then evaporated to a minimum and the residue re-dissolved in DCM (50 ml) and washed with sodium hydrogen carbonate (3×50ml) and brine (50 ml). The organic layer was dried (MgSO$_4$) and evaporated. The crude product was purified by column chromatography [silica gel, step gradient 0-10% MeOH (containing 10% 0.880 ammonia solution) in DCM]. Fractions containing the required product were evaporated to give the subtitled compound as a white solid (1.20 g). MS electrospray (+ve) 388 (MH$^+$).

Step 2: 1-Isopropyl-4-[1-(4-carboxy-phenyl)-piperidin-4-carbonyl]-piperazine hydrochloride The product of D9, Step 1 (1.22 g) was dissolved in dioxane (20 ml) and 2M lithium hydroxide (3.1 ml) added and the mixture heated to reflux for 2 h. The reaction mixture was then evaporated to a minimum, re-dissolved in DCM (50 ml) and treated with 4N HCl in dioxane (20 ml). The mixture was then evaporated (co-evaporated with toluene) to give the title compound (D9) as a white solid (1.51 g, contains 2 eq. LiCl). MS electrospray (+ve) 360 (MH$^+$).

Description 10

1-Cyclobutyl-4-(piperidine-4-carbonyl)-[1,4]-diazepane (D10)

Step 1: 1-Cyclobutyl-4-(1-tert-butoxycarbonyl-piperidine-4-carbonyl)-[1,4]-diazepane 1-(1-tert-Butoxycarbonyl-piperidine-4-carbonyl)-[1,4]-diazepane (2.0 g)(D8, Step 2) was dissolved in DCM (50 ml) and cyclobutanone (0.96 ml) added and the mixture stirred for 5 min. Sodium triacetoxyborohydride (2.7 g) was then added and the reaction stirred at rt for 1.5 h. The reaction mixture was then washed with saturated potassium carbonate solution (50 ml), sodium hydrogen carbonate solution (3×50 ml) and brine (50 ml). The organic layer was dried (MgSO$_4$) and evaporated to give the subtitled compound as a white solid (1.67 g).

Step 2: 1-Cyclobutyl-4-(piperidine-4-carbonyl)-[1,4]-diazepane

The product of D10, Step 1 (1.67 g) was dissolved in methanol (30 ml) and 4N HCl in dioxane (10 ml) added. The reaction was then stirred at rt for 16 h. The reaction mixture was then evaporated to a minimum and the residue basified with saturated potassium carbonate solution (50 ml) and extracted with DCM (3×50 ml). The organic layer was then dried (MgSO$_4$) and evaporated to give the title compound (D10) as a white solid (1.50 g). MS electrospray (+ve) 266 (MH$^+$). $^1$H NMR δ [DMSO-d6]: 3.60 (5H, m), 3.30 (1H, m), 3.10-2.65 (4H, m), 2.41 (4H, m), 2.05-1.58 (12H, m).

Description 11

1-(5-Cyano-pyridin-2-yl)-piperidine4-carboxylic acid (D11)

Step 1: Ethyl 1-(5-cyano-pyridin-2-yl)-piperidine-4-carboxylic acid

Piperidine-4-carboxylic acid ethyl ester (5.7 g) was dissolved in DMSO (100 ml) and potassium carbonate added followed by 6-chloronicotinitrile (5.0 g). The reaction was heated to 50° C. for 4 h under argon. The reaction mixture was then evaporated to a minimum and the residue acidified to pH-2 with aqueous 1N HCl solution. The aqueous mixture was then extracted with DCM (2×50 ml). The combined organic layers were then washed with sodium hydrogen carbonate (2×50 ml), brine (50 ml) and then dried (MgSO$_4$) and evaporated to give the subtitled compound as a white solid (8.96 g).

Step 2: 1-(5-Cyano-pyridin-2-yl)-piperidine-4-carboxylic acid

The product of D11, Step 1 (8.96 g) was dissolved in 1,4-dioxane (50 ml) and 1M LiOH solution (38 ml) added and the solution stirred at rt for 4 h. The reaction mixture was then evaporated to a minimum and the residue acidified to pH-2 with aqueous 2N HCl acid and extracted with DCM (2×100 ml). The combined organic extracts were then washed with brine (50 ml), dried (MgSO$_4$) and evaporated to give the title compound (D11) as a white powder (6.60 g).

Description 12

1-(5-Cyano-pyridin-2-yl)-piperidinecarbonyl chloride (D12)

1-(5-Cyano-pyridin-2-yl)-piperidine-4-carboxylic acid (D11)(5.5 g) was heated to reflux in thionyl chloride (50 ml) for 1.5 h and then allowed to stand at rt under argon overnight. The reaction was then evaporated (co-evaporated 3× with DCM) to give the title compound (D12) as a yellow solid (5.70 g).

Description 13

(2R,6S)-4-[1-(4-Cyanophenyl)-piperidine-4-carbonyl]-2,6-dimethylpiperazine hydrochloride (D13)

1-(4-Cyanophenyl)-piperidine4-carboxylic acid (D3) (6.92 g), HOBT (1.77 g), TEA (4.7 ml) and (2R,6S)-2,6-dimethylpiperazine (3.0 g) were stirred in DMF (25 ml) and then EDC (3.7 g) was added and the reaction stirred at rt overnight. The solvent was evaporated and the residue redissolved in DCM (100 ml) and washed with saturated sodium hydrogen carbonate (2×80 ml), brine (75 ml) and the organic layer dried (MgSO$_4$) and evaporated. The crude product was then purified by column chromatography [silica gel, step gradient 0-10% MeOH (containing 10% 0.880 ammonia solution) in DCM]. Fractions containing the required product were evaporated to give the free base compound which was dissolved in DCM (10 ml) and treated with 1N HCl in diethyl ether to give the title compound (D13) as a white precipitate which was filtered off (1.80 g). MS electrospray (+ve) 327 (MH$^+$).

Description 14

1-[1-(5-Cyanopyrldin-2-yl)-piperidine-4-carbonyl]-[1,4]diazepane hydrochloride (D14)

1-tert-Butoxy-carbonyl-[1,4]-diazepane (4.0 g) and TEA (3.63 ml) were stirred in DCM (15 ml). 1-(5-Cyano-pyridin-2-yl)-piperidine4-carbonyl chloride (D12)(5.70 g) in DCM (15 ml) was then added and the reaction stirred at rt under argon overnight. The reaction mixture was then washed with sodium hydrogen carbonate (2×50 ml) and brine (50 ml). The organic layer was dried (MgSO$_4$) and evaporated to give a crude product which was purified by column chromatography [silica gel, gradient elution 0-100% EtOAc in hexane]. Pure product fractions were combined and evaporated to give a pale yellow solid (1.10 g) which was dissolved in 1,4-dioxane (30 ml) treated with 4N HCl in 1,4-dioxane (5 ml) and then stirred at rt for 2 h. The solvent was evaporated to give the title compound (D14) as a yellow solid (0.92 g).

Description 15

(S)-1-[1-(4-Cyanophenyl)-piperidine-4-carbonyl]-3-methylpiperazine (D15)

A stirred solution of 1-(4-cyanophenyl)-piperidine-4-carboxylic acid (D3)(230 mg) in DCM (10 ml) at rt was treated with oxalyl chloride (0.13 ml) and 10% DMF in DCM (1 drop). After 1 h the solution was evaporated and then re-evaporated from DCM (2×5 ml). The acid chloride was redissolved in DCM (10 ml) at rt and treated with diethylaminomethylpolystyrene (780 mg, 3.2 mmol/g) and (S)-2-methylpiperazine (100 mg) and stirred overnight. The mixture was flash chromatographed [silica gel, step gradient 4-10% MeOH (containing 10% 0.880 ammonia solution) in DCM]. Fractions containing the required product were evaporated to give the title compound (D15) (248 mg). MS electrospray (+ve) 313 (MH$^+$). $^1$H NMR δ (CDCl$_3$): 7.47 (2H, d, J=9 Hz), 6.85 (2H, d, J=9 Hz), 4.47 (1H, m), 4.60-4.40 (1H, m), 3.97-3.65 (3H, m), 3.24-2.55 (8H, m), 2.28 (1H, m), 2.03-1.61 (4H, m), 1.80-1.45 (4H, m), 1.08 (3H, m)

Description 16

(R)-1-[1-(4-Cyanophenyl)-piperidine4-carbonyl]-3-methylpiperazine (D16)

The title compound (D16) was prepared from 1-(4-cyanophenyl)-piperidine4-carboxylic acid (D3) and (R)-2-methylpiperazine using the procedure of Description D15.

Description 17

(2R, 5S) and (2S, 5R)-1-[1-(4-Cyanophenyl)-piperidine-4-carbonyl]-2,5-dimethylpiperazine (D17)

The title compound (D17) was prepared from 1-(4-cyanophenyl)-piperidine4-carboxylic acid (D3) and (2S, 5R)-2,5-dimethylpiperazine using the procedure of Description D15.

Description 18

(3S, 5S)-1-[1-(4-Cyanophenyl)-piperidine-4-carbonyl]-3,5-dimethylpiperazine (D18)

The title compound (D18) was prepared using a similar procedure to Description 4 step 1 from 1-(4-cyanophenyl)-piperidine4-carboxylic acid (D3), (2S, 6S)-2,6-dimethylpiperazine dihydrochloride (J. W. Mickleson, K. L. Belonga and E. J. Jacobsen, J. Org. Chem., 1995, 60(13), 4177-4183), EDC, HOBT and N-methyl morpholine in DMF.

Description 19

(S)-1-Benzyloxycarbonyl-3-methylpiperazine (D19)

Benzyl chloroformate (16.3 ml) in DCM (30 ml) was added dropwise to a cooled solution at 0° C. of (S)2-methylpiperazine (10 g) in DCM (200 ml) and triethylamine (14.5 ml). The temperature was allowed to rise from 0° C. to rt and the reaction mixture was stirred at rt for 3 h. The mixture was washed with saturated aqueous NaHCO$_3$ (2×100 ml). The DCM layer was dried (MgSO$_4$) and filtered. The filtrate was absorbed onto silica and then purified by column chromatography [silica gel, step gradient 0-10% MeOH (containing 10% 0.88 ammonia solution) in DCM] to give the title compound (D19) as an oil (10.18 g). LCMS electrospray (+ve) 235 (MH$^+$).

Description 20

(S)-1-Benzyloxycarbonyl-4-[1-(tert-butoxycarbonyl)-piperidine-4-carbonyl]-3-methylpiperazine (D20)

1-(tert-Butoxycarbonyl)-piperidine4-carboxylic acid (0.53 g), (S)-1-benzyloxycarbonyl-3-methylpiperazine (D19)(0.5 g), HOBt (0.29 g) and diethylaminomethyl polystyrene (1.78 g) were stirred in DCM (30 ml), then EDC (0.53 g) was added and the reaction was stirred at rt overnight. The mixture was filtered and washed with saturated sodium hydrogen carbonate solution (3×50 ml) and brine (30 ml). The organic layer was dried (MgSO$_4$) and evaporated to give a crude yellow oil which was purified by chromatography [silica gel; 0-100% ethyl acetate/hexane) to give the tide compound (D20) as a clear oil which crystallised on standing (0.88 g).

Description 21

(S)-1-[1-(tert-Butoxycarbonyl)-piperidine-4-carbonyl]-2-methylpiperazine (D21)

(S)-1-Benzyloxycarbonyl-4-[1-(tert-butoxycarbonyl)-piperidine-4-carbonyl]-3-methylpiperazine (D20)(0.38 g) was dissolved in ethanol (10 ml) and hydrogenated at atmospheric pressure over 10% Palladium on charcoal (10% water paste, catalytic quantity). After 16 h the catalyst was removed by filtration and the filtrate was evaporated to give the title compound (D21) as a white powder (0.26 g).

Description 22

(S)-1-Isopropyl-4-[1-(tert-butoxycarbonyl)-piperidine-4-carbonyl]-3-methylpiperazine (D22)

(S)-1-[1-(tert-Butoxycarbonyl)-piperidine-4-carbonyl]-2-methylpiperazine (D21)(0.13 g), 2-iodopropane (0.08 ml) and potassium carbonate (0.1 g) in acetonitrile (2 ml) were heated at 120° C. in an Emerys Optimiser microwave for 45 min. The mixture was then filtered and evaporated. The crude product was redissolved in DCM (30 ml) and washed with saturated sodium hydrogen carbonate solution (3×20 ml) and brine (20 ml). The organic layer was dried (MgSO$_4$) and evaporated to give the title compound (D22) as a clear oil (0.11 g)

Description 23

(S)-1-Isopropyl-4-(piperidine-4-carbonyl)-3-methylpiperazine dihydrochloride (D23)

(S)-1-Isopropyl4-[1-(tert-butoxycarbonyl)-piperidine4-carbonyl]-3-methylpiperazine (D22)(0.11 g) was dissolved in methanol (10 ml) and treated with HCl (4N HCl in diethyl ether; 10 ml). After being stirred at rt overnight the reaction mixture was evaporated to a minimum, co-evaporated from methanol, and then dried at 50° C. to give the title compound (D23) as a pale brown solid (0.10 g)

Description 24

(S)-1-Cyclobutyl-4-[1-(tert-butoxycarbonyl)-piperidine-4-carbonyl]-3-methylpiperazine (D24)

(S)-1-[1-(tert-Butoxycarbonyl)-piperidine-4-carbonyl]-2-methylpiperazine (D21)(0.13 g) and cyclobutanone (0.1 ml) were stirred in methanol (10 ml) at rt for 10 min and then sodium triacetoxyborohydride (0.26 g) was added and the reaction stirred at rt overnight. The reaction mixture was evaporated to a minimum and then redissolved in DCM (30 ml), and washed with saturated potassium carbonate solution (3×25 ml). The organic layer was dried (MgSO$_4$) and evaporated to give the title compound (D24) as a clear oil (0.13 g).

Description 25

(S)-1-Cyclobutyl-4-(piperidine-4-carbonyl)-3-methylpiperazine dihydrochloride (D25)

The title compound (D25) was prepared from (S)-1-cyclobutyl-4-[1-(tert-butoxycarbonyl)-piperidine-4-carbonyl]-3-methylpiperazine (D24) using the procedure of Description 23.

Description 26

(S) 1-Isopropyl-4-(benzyloxycarbonyl)-2-methylpiperazine (D26)

Potassium carbonate (11.2 g) was added to a solution of (S)-1-benzyloxycarbonyl-3-methylpiperazine (D19)(10.18 g) in CH$_3$CN (60 ml), followed by isopropyl iodide (11.3 ml) and the mixture was heated at reflux overnight. The reaction mixture was then allowed to cool to rt and the inorganics were filtered off. The filtrate was evaporated to give an oil which was taken up in EtOAc (100 ml) and washed with water (2×50 ml). The EtOAc layer was dried (MgSO$_4$) and concentrated to give the title compound (D26) as an oil (8 g). LCMS electrospray (+ve) 277 (MH$^+$).

Description 27

(S)-1-Isopropyl-2-methylpiperazine hydrochloride (D27)

(S)-1-isopropyl-4-(benzyloxycarbonyl)-2-methylpiperazine (D26)(7.6 g) was dissolved in EtOH (120 ml) and treated with 10% Pd/C (2 g) and hydrogenated under atmospheric conditions overnight. The catalyst was filtered off and washed with EtOH (30 ml). The filtrate was treated with ethereal HCl (10 ml, 1N HCl in diethyl ether) and evaporated to dryness to give the title compound (D27) as a solid (2 g). LCMS electrospray (+ve) 143 (MH$^+$).

Description 28

(S)-1-isopropyl-4-[1-(tert-Butoxycarbonyl)-piperidine-4-carbonyl]-2-methyl piperazine (D28)

1-(tert-Butoxycarbonyl)-piperidine4-carboxylic acid (3.2 g) in dry DMF (30 ml) was treated first with EDC (5.4 g) and catalytic HOAt followed by (S)-1-isopropyl-2-methyl piperazine hydrochloride (D27)(2 g) and N,N-diisopropylethylamine (5 ml). After the reaction mixture was stirred overnight, water (50 ml) was added and the cloudy precipitate was extracted into EtOAc (2×25 ml), dried (MgSO$_4$) and filtered. The filtrate was absorbed on silica and purified by column chromatography [silica gel, step gradient 0-10% MeOH (containing 10% 0.88 ammonia solution) in DCM]. The fractions containing the required product were evaporated to give the title compound (D28) as an oil (3.8 g). LCMS electrospray (+ve) 354 (MH$^+$).

Description 29

(S)-1-isopropyl-4-(piperidine-4-carbonyl)-2-methylpiperazine dihydrochloride (D29)

(S)-1-Isopropyl-4-[1-(tert-butoxycarbonyl)-piperidine-4-carbonyl]-2-methyl-piperazine (D28)(3.8 g) was treated with HCl as described in Description 8 step 4 to give the title dihydrochloride (D29) as a white solid (2.5 g). LCMS electrospray (+ve) 254 (MH$^+$).

Description 30

5-Bromo-2-trifluoromethylpyrimidine (D30)

A mixture of potassium fluoride (1.77 g) and cuprous iodide (5.79 g) was stirred and heated together using a heat gun under vacuum (~1 mm) for 20 min. After cooling, dimethyl formamide (20 ml) and N-methyl pyrrolidinone (20 ml) were added followed by (trifluoromethyl)trimethylsilane (4.1 ml) and 5-bromo-2-iodopyrimidine (6.5 g). The mixture was stirred at rt for 5 h and then the brown solution was poured into 6N ammonia solution. The product was extracted into ethyl acetate and the extracts were washed with sodium bicarbonate solution and brine and then dried (Na$_2$SO$_4$) and evaporated. Chromatography on silica gel (elution with 20-50% dichloromethane in pentane) gave the title compound (D30) as a white solid (2.4 g). $^1$H NMR (CDCl$_3$): 8.97 (2H, s).

Description 31

2-Chloro-5-trifluoromethylpyrazine (D31)

2-Amino-5-trifluoromethylpyrazine (Miesel, U.S. Pat. No. 4,293,552) was converted into 5-trifluoromethylpyrazin-2-one (Fitzjohn, EP 408196). 5-Trifluoromethylpyrazin-2-one (0.5 g) was heated at reflux in POCl$_3$ (3 ml) containing 1 drop of conc. H$_2$SO$_4$ for 3 h. The cooled mixture was poured onto ice and brought to pH 5 by addition of solid NaHCO$_3$ and extracted (3×) with diethyl ether. The ethereal extracts were washed with water and brine, dried (Na$_2$SO$_4$) and evaporated to give the title compound (D31) as a light yellow oil (0.2 g) which was sufficiently pure for use without further purification. $^1$H NMR δ [CDCl$_3$]: 8.72 (1H, s), 8.76 (1H, s).

Description 32

(S)-1-Methylpropyl methanesulfonate (D32)

An ice cold solution of (S)-2-butanol (888 mg) in DCM (15 ml) was treated with Et$_3$N (1.26 ml) and followed by dropwise addition of methanesulfonyl chloride (0.52 ml). After 1 h the solution was washed with saturated sodium hydrogen carbonate solution (5 ml), water (2×5 ml), brine (5 ml), dried (MgSO$_4$) and evaporated to give the title compound (D32)

(1.01 g). $^1$H NMR δ (CDCl$_3$): 4.74 (1H, m), 3.00 (3H, s), 1.67 (2H, m), 1.41 (1H, d, J=6.5 Hz), 0.99 (3H, t, J=7.5 Hz).

Description 33

(R)-1-Methylpropyl methanesulfonate (D33)

An ice cold solution of (R)-2-butanol (888 mg) in DCM (15 ml) was treated with Et$_3$N (1.26 ml) and followed by dropwise addition of methanesulfonyl chloride (0.52 ml). After 1 h the solution was washed with saturated sodium hydrogen carbonate solution (5 ml), water (2×5 ml), brine (5 ml), dried (MgSO$_4$) and evaporated to give the title compound (D33) (0.9 g). $^1$H NMR δ (CDCl$_3$): 4.74 (1H, m), 3.00 (3H, s), 1.67 (2H, m), 1.41 (1H, d, J=6.5 Hz), 0.99 (3H, t, J=7.5 Hz).

Description 34

1-[1-(4-Cyanophenyl)-piperidine-4-carbonyl]-piperazine hydrochloride (D34)

The title compound (D34) was prepared from 1-(4-cyanophenyl)-piperidine-4-carboxylic acid (D3) and 1-tert-butoxycarbonylpiperazine in a similar manner to Description 4.

Description 35

2-Chloro-5-(1-pyrrolidinylcarbonyl)pyridine (D35)

6-Chloronicotinic acid (1 g) in DMF (30 ml) was treated with EDC (2.43 g) followed by HOAt (10 mg). After 15 min N,N-diisopropylethylamine (2.2 ml) followed by pyrrolidine (0.53 ml) was added. The reaction mixture was allowed to stir at rt overnight. The DMF was removed by evaporation and the resulting residue was partitioned between saturated NaHCO$_3$ and DCM. The DCM layer was dried (MgSO$_4$) and filtered, the filtrate was absorbed on silica gel and purified by column chromatography [silica gel, step gradient 0-10% MeOH (containing 10% 0.88 ammonia solution) in DCM]. Fractions containing the required product were evaporated to give the title compound (D35) as a solid (0.28 g). MS electrospray (+ve ion) 211 (MH$^+$).

Description 36

2-Chloro-5-(dimethylaminocarbonyl)pyridine (D36)

The title compound (D36) was prepared from dimethylamine and 6-chloronicotinic acid according to the procedure described for Description 35. MS electrospray (+ve ion) 185 (MH$^+$).

Description 37

4-(4-Bromophenyl)-2-methyl-oxazole (D37)

4-Bromophenacyl bromide (21.3 g) and acetamide (11.3 g) were heated together at 130° C. under argon. After 2.5 h the reaction mixture was allowed to cool, and partitioned between water (150 ml) and Et$_2$O (150 ml). The organic phase was washed with aqueous NaOH (0.5N), aqueous HCl (0.5M) and saturated aqueous NaCl solution (100 ml of each), dried (MgSO$_4$) and evaporated to give a brown solid which was recrystallised from hexanes to give the title compound (D37) as an orange solid (4.1 g). LCMS electrospray (+ve) 239 (MH$^+$).

Description 38

5-(4-Bromophenyl)-2-methyl-oxazole (D38)

Trifluoromethanesulfonic acid (6.6 ml) was added to a flask containing iodobenzene diacetate (12.2 g) and MeCN (200 ml) at rt. After 25 min. a solution of 4'-bromoacetophenone (5 g) in MeCN (50 ml) was added and the resultant mixture heated at reflux for 6 h. The reaction was allowed to cool to rt before the solvent was evaporated and the residue partitioned between saturated aqueous Na$_2$CO$_3$ (150 ml) and EtOAc (150 ml). The organic phase was washed with saturated brine (150 ml), dried (MgSO$_4$) and evaporated to give an orange solid. The crude product was purified by column chromatography (silica gel, 50% EtOAc in hexane) to give the title compound (D38) as a pale yellow solid (3.5 g). LCMS electrospray (+ve) 239 (MH$^+$).

Description 39

5-(4-Bromophenyl)-3-methyl isoxazole (D39)

A solution of n-BuLi (81 ml of a 1.6M solution in hexanes) was added to a solution of acetone oxime (4.85 g) in THF (100 ml) at 0° C. The reaction mixture was allowed to warm to rt over 1 h. A solution of methyl 4-bromobenzoate (9.4 g) in THF (30 ml) was then added to the reaction mixture and allowed to stir for 24 h. Water (50 ml) was added to the reaction, the organics were extracted and evaporated to give a brown oil, which was further evaporated from toluene (2×25 ml). The crude product was purified by column chromatography (silica gel, 10-25% gradient of EtOAc in hexane) to give the title compound (D39) as a pale yellow solid (5.4 g). LCMS electrospray (+ve) 239 (MH$^+$).

Description 40

3-(4-Bromophenyl)-5-methyl-1,2,4-oxadiazole (D40)

Step 1:
4-Bromo-N-hydroxy-benzenecarboximidamide

4-Bromophenylcarbonitrile (10.2 g), hydroxylamine hydrochloride (7.8 g) and Et$_3$N (11.3 g) were dissolved in EtOH (250 ml) and the reaction mixture was heated at reflux for 3 h, after which it was evaporated to form a white precipitate of the desired amidoxime, which was filtered off and washed with water (25 ml). The filtrate was extracted into EtOAc (2×25 ml), and the combined organic extracts were dried (Na$_2$SO$_4$) and evaporated to give a second crop of the subtitle compound (combined yield=11.1 g). LCMS electrospray (+ve) 216 (MH$^+$).

Step 2:
3-(4-Bromophenyl)-5-methyl-1,2,4-oxadiazole

The product from D40, step 1 was suspended in acetic anhydride and heated to 100° C. for 4 h, then 120° C. for 3 h. After cooling the reaction mixture was evaporated to give a brown solid. This was partitioned between saturated aqueous NaHCO$_3$ and EtOAc. The organic phase was washed with saturated aqueous NaCl, dried (Na$_2$SO$_4$) and evaporated to give a yellow solid. The crude product was purified by column chromatography (silica gel, 10-100% gradient of EtOAc in hexane) to give the title compound (D40) as a white solid (6.2 g). LCMS electrospray (+ve) 240 (MH$^+$).

Description 41

5-(4-Bromophenyl)-3-methyl-1,2,4-oxadiazole (D41)

4-Bromobenzamide (5.3 g) and dimethylformamide dimethoxyacetal (35 ml) were heated together at 125° C. for 2 h. The reaction was allowed to cool to rt and the liquid evaporated to give a pale yellow solid. Hydroxylamine hydrochloride (2.2 g) in 1N NaOH solution (36 ml) was added, followed by dioxane (36 ml) then AcOH (48 ml). The reaction mixture was stirred at rt for 30 min then heated at 90° C. for 3 h. The reaction was allowed to cool to rt and saturated aqueous $K_2CO_3$ solution (100 ml) was added followed by DCM (200 ml) before filtering. The organic phase was separated from the mixture, then saturated brine (100 ml) was added and the aqueous phase was extracted into EtOAc (200 ml). The combined organic phases were dried ($Na_2SO_4$) and evaporated to give a brown solid. The crude product was purified by column chromatography (silica gel, step gradient 10-50% EtOAc in hexane) to give the title compound (D41) as a white solid (2.9 g). LCMS electrospray (+ve) 240 (MH$^+$).

Description 42

2-Chloro-5-(methylaminocarbonyl)pyridine (D42)

The title compound (D42) was prepared from methylamine and 6-chloronicotinic acid according to the procedure described for Description 35.

EXAMPLE 1

1-Isopropyl-4-[1-(5-cyano-pyridin-2-yl)-piperidine4-carbonyl]-piperazine hydrochloride (E1)

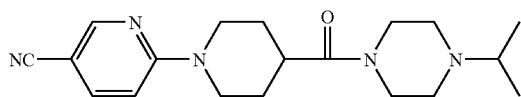

To 1-isopropyl-4-(piperidine4-carbonyl)-piperazine (0.239 g)(D1) and 2-chloro-5-cyano-pyridine (0.138 g), dissolved in DMSO (5 ml), was added potassium carbonate (0.14 g). The reaction was heated to 80° C. for 4 h before cooling and dilution with saturated sodium hydrogen carbonate (50 ml) and EtOAc (80 ml). The EtOAc layer was washed further with brine (3×80 ml) and then extracted with 1N HCl. The aqueous HCl extract was basified and back-extracted with EtOAc which was concentrated under vacuum. A solution of 2N HCl in diethyl ether (1 ml) was then added and the precipitate filtered and washed with diethyl ether. Crystallisation from methanol afforded the title compound (E1)(0.15 g). $^1$H NMR δ [DMSO-d6]:1.29 (6H, d, J=6.4 Hz), 1.4-1.6 (2H, m), 1.7-1.85 (2H, m), 2.8-3.27 (6H, m), 3.32-3.62 (3H, m), 3.69 (1H, m), 4.24 (1H, brd, J=13 Hz), 4.35-4.55 (3H, m), 6.96 (1H, d, J=9.1 Hz), 7.84 (1H, dd, J=9.1Hz and 1.5 Hz), 8.47 (1H, d, J=1.5 Hz) and 11.36 (1H, brs). MS electrospray; (+ve ion) 342 (MH+).

EXAMPLE 2

1-Isopropyl-4-[1-(4-cyanophenyl)-piperidine-4-carbonyl]-piperazine hydrochloride (E2)

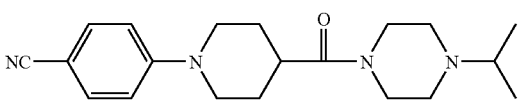

The title compound (E2) was prepared from 4-fluorobenzonitrile and 1-isopropyl-4-(piperidine-4-carbonyl)-piperazine (D1) according to the procedure described in Example 1, except that the reaction was carried out at 120° C. for 8 h. $^1$H NMR δ [DMSO-d6]: 1.29 (6H, d, J=6.5 Hz), 1.4-1.8 (4H, m), 2.8-3.1 (5H, m), 3.11-3.22 (1H, m), 3.31-3.5 (3H, m), 3.62-3.77 (1H, m), 3.89-4 (2H, m), 4.2 (1H, brd, J=13.5 Hz), 7.03 (2H, d, J=9 Hz), 7.56 (2H, d, J=9 Hz) and 11.43 (1H, brs). MS electrospray; (+ve ion) 341 (MH+).

EXAMPLES 3-5 (E3-E5)

Example 3 was prepared as described for D2. Examples 4 and 5 were prepared from 1-isopropyl4-(piperidine4-carbonyl)-piperazine (D1) and the appropriate heteroaryl chloride using the procedure described in Example 1 and displayed $^1$H NMR and mass spectral data that were consistent with structure.

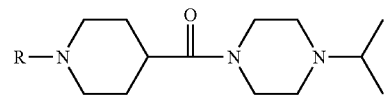

| Example No | R | Heteroaryl Chloride | Mass Spectrum (ES$^{+}$) |
|---|---|---|---|
| E3 | Br—⟨pyrimidine⟩— | Br—⟨pyrimidine⟩—Cl | [MH]$^+$ 396/398 |
| E4 | MeO$_2$C—⟨pyridine, F$_3$C⟩— | MeO$_2$C—⟨pyridine, F$_3$C⟩—Cl | [MH]$^+$ 443 |

-continued

| Example No | R | Heteroaryl Chloride | Mass Spectrum (ES+) |
|---|---|---|---|
| E5 | 4-cyano-2-methylpyridin-yl (pyridine with NC and methyl) | 2-chloro-4-cyanopyridine | [MH]+ 342 |

EXAMPLES 6-8 (E6-E8)

Examples 6 and 7 were prepared from 1-isopropyl-4-(piperidine-4-carbonyl)-piperazine (D1) and the appropriate aryl fluoride using the procedure described in Example 2. Example 8 was prepared using the procedure described in D9, Step 1. Compounds displayed $^1$H NMR and mass spectral data that were consistent with structure.

| Example No | R | Aryl Fluoride | Mass Spectrum (ES+) |
|---|---|---|---|
| E6 | 2-cyanophenyl | 2-fluorobenzonitrile | [MH]+ 341 |
| E7 | 3-cyanophenyl | 3-fluorobenzonitrile | [MH]+ 341 |
| E8 | 4-(EtO₂C)phenyl | ethyl 4-fluorobenzoate | [MH]+ 388 |

EXAMPLES 9-19 (E9-E19)

Examples 9-19 were prepared from 1-cyclobutyl-4-(piperidine-4-carbonyl)-piperazine di-hydrochloride (D7) and the appropriate aryl halide, using the procedures described in Example 1 (for E14-E19) and Example 2 (for E9-E13), and displayed $^1$H NMR and mass spectral data that were consistent with structure.

| Example No | R | Mass Spectrum (ES+) |
|---|---|---|
| E9 | 4-cyanophenyl | [MH]+ 353 |

-continued

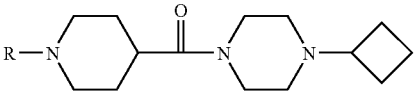

| Example No | R | Mass Spectrum (ES+) |
|---|---|---|
| E10 | 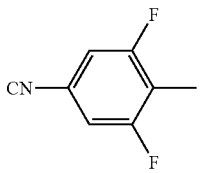 | [MH]+ 371 |
| E11 | 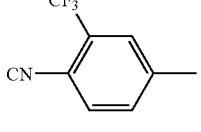 | [MH]+ 389 |
| E12 | 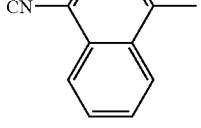 | [MH]+ 421 |
| E13 | 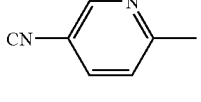 | [MH]+ 403 |
| E14 | 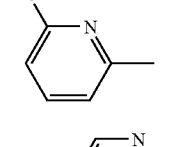 | [MH]+ 354 |
| E15 | 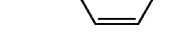 | [MH]+ 397 |
| E16 | 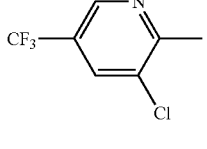 | [MH]+ 397 |
| E17 | 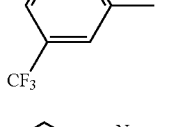 | [MH]+ 431 |
| E18 | 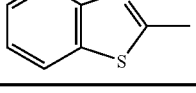 | [MH]+ 397 |
| E19 |  | [MH]+ 385 |

EXAMPLE 20

1-Isopropyl-4-[1-(5-cyano-pyrimidin-2-yl)-piperidine-4-carbonyl]-piperazine hydrochloride (E20)

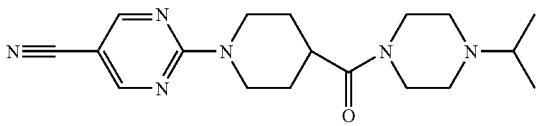

1-Isopropyl-4-[1-(5-bromo-pyrimidin-2-yl)-piperidine-4-carbonyl]-piperazine (D2)(0.5 g) in DMF (10 ml) was treated with CuCN (0.1 g) and the reaction mixture was refluxed overnight. The DMF was removed by evaporation and the residue was partitioned between $H_2O$/EtOAc (20:20 ml). The EtOAc layer was dried ($MgSO_4$) and evaporated to dryness and purified first by chromatography [silica gel 0-10% MeOH (containing 10% 0.88 ammonia solution)/DCM] followed by further purification on a Waters Mass Directed Auto Preparative HPLC eluting with (0.1% formic acid in water and 0.1% formic acid acetonitrile gradient 10-100%). The isolated product peaks were combined and evaporated to give the desired product as the formate salt which was converted to the HCl salt in MeOH/ethereal 1N HCl (2 ml). The solvents were removed by evaporation to give the title compound (E20) as a white solid (17 mg). $^1$H NMR δ [DMSO-d6]: 1.29 (6H, d, J=6.5), 1.40-1.58 (2H, m), 1.70-1.81 (2H, m), 2.90-3.5 (10H, m), 4.25-4.8 (4H, m), 8.74 (2H, s), 10.9 (1H, bs). LCMS electrospray (+ve) 343 (MH+).

EXAMPLE 21

1-Isopropyl-4-{1-[5-(pyridin-3-yl)-pyrimidin-2-yl]piperldine-4-carbonyl}-piperazine hydrochloride (E21)

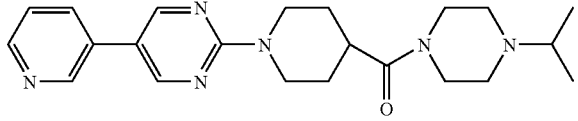

A mixture of 1-isopropyl-4-[1-(5-bromo-pyrimidin-2-yl)-piperidine-4-carbonyl]-piperazine (D2)(0.25 g), 3-pyridyl boronic acid (0.1 g), 2M $K_2CO_3$ (1.5 ml) and EtOH (1.5 ml) in toluene (10 ml) were stirred under a stream of argon for 30 min. After this time Pd(PPh$_3$)$_4$ (50 mg) was added and the reaction mixture was refluxed overnight. Water (1 ml) was added and the reaction mixture was stirred at rt for 5 min. The mixture was passed through a 20 g Varian Hydromatrix disposable liquid/liquid extraction cartridge and washed with EtOAc (30 ml). The EtOAc layer was absorbed on silica (4 g) and purified by chromatography [silica gel 0-10% MeOH (containing 10% 0.88 ammonia solution)/DCM]. The free base was dissolved in MeOH (5 ml) and treated with 1N ethereal HCl (2 ml). The solvents were removed by evaporation to give the title compound (E21) as a white solid (150 mg). $^1$H NMR δ [DMSO-d6]: 1.29 (6H, d, J=6.5), 1.4-1.6 (2H, m), 1.7-1.8 (2H, m), 2.8-2.9 (1H, m), 3.0-3.2 (6H, m), 3.38-3.44 (2H, m), 3.42-3.5 (1H, m), 3.66-3.73 (1H, m), 4.25-4.3 (1H, s), 4.47-4.5 (1H, m), 4.74-4.8 (2H, m), 8.0-8.08 (1H, m), 8.78-8.81 (2H, dd, J=2.5), 8.90 (1H, s), 9.23 (1H, d, J=1.5), 11.20 (1H, brs); LCMS electrospray (+ve) 395(MH+).

EXAMPLE 22

1-Isopropyl-4-[1-(5-morpholino-pyrimidin-2-yl)-piperidine-4-carbonyl]-piperazine hydrochloride (E22)

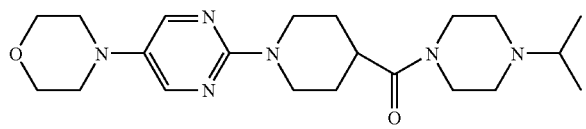

Bis(tri-t-butylphosphine)palladium(0)(20 mg) was added to o-xylene(10 ml) and the reaction mixture was stirred at rt for 10 min to give an orange coloured solution. 1-Isopropyl-4-[1-(5-bromo-pyrimidin-2-yl)-piperidine-4-carbonyl]-piperazine (D2)(0.25 g) in o-xylene (10 ml) was added to the orange solution followed by addition of NaO$^t$Bu (84 mg) and morpholine (0.12 g) The reaction mixture was refluxed for 1 h. After cooling the reaction mixture was partitioned between H$_2$O/EtOAc (30:20 ml), the EtOAc layer was dried (MgSO$_4$) and filtered, the filtrate was absorbed onto silica gel (3 g) and purified by chromatography [silica gel 0-10% MeOH (containing 10% 0.88 ammonia solution)/DCM]. The free base was taken up in dry MeOH (3 ml) and treated with ethereal HCl. The solvents were removed by evaporation to give the title compound (E22) as a white solid (67 mg). $^1$H NMR δ [DMSO-d6]: 1.29 (6H, d, J=6.5), 1.4-1.6 (2H, m), 1.68-1.7 (2H, m), 2.92-3.16 (10H, m), 3.37-3.65 (4H, m), 3.74-3.76 (4H, m), 4.22-4.25(1H, m), 4.47-4.60(3H, m), 8.26 (2H, s), 10.85 (1H, bs). LCMS electrospray (+ve) 403 (MH$^+$).

EXAMPLE 23

1-Isopropyl-4-[1-(2-morpholino-pyrimidin-5-yl)-piperidine-4-carbonyl]-piperazine hydrochloride (E23)

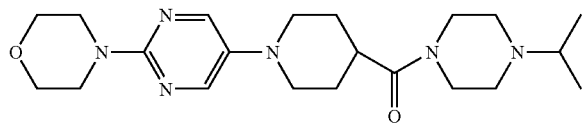

Step 1: 4-(5-Bromo-pyrimidin-2-yl)-morpholine

Potassium carbonate (0.34 g) was added to a solution of 2-chloro-5-bromo-pyrimidine (0.5 g) in DMF (20 ml). The reaction mixture was stirred at rt for 15 min. Morpholine (0.2 g) was added and the reaction mixture was stirred at rt for 2 h. The excess DMF was removed by evaporation and the residue was partitioned between H$_2$O/EtOAc (30:30 ml) The EtOAc layer was dried (MgSO$_4$) and evaporated to dryness to give the sub-title compound as a cream solid (0.2 g). LCMS electrospray(+ve) 246 (MH$^+$).

Step 2: 1 Isopropyl-4-(2-morpholino-pyrimidin-5-yl)-piperldine-4-carbonyl)-piperazine hydrochloride The title compound was prepared by reacting the product of E23, Step 1 with 1-isopropyl-4-(piperidine-4-carbonyl)-piperazine (D1) using the conditions described in Example 22. $^1$H NMR δ [DMSO-d6]; 1.29 (6H, d, J=6.5), 1.78 (4H, m), 2.80-3.1 (4H, m), 3.2-4.7 (18H, m), 8.35 (2H, s), 10.65 (m, 1H). LCMS electrospray(+ve) 403 (MH$^+$).

EXAMPLES 24-26 (E24-E26)

Examples 24-26 were prepared from 1-isopropyl-4-[1-(5-bromo-pyrimidin-2-yl)-piperldine-4-carbonyl]-piperazine (D2) and an appropriate aryl boronic acid using the procedure described in Example 21 and displayed $^1$H NMR and mass spectral data that were consistent with structure.

| Example No | R | Mass Spectrum (ES$^+$) |
|---|---|---|
| E24 | (2,3-dihydrobenzofuran-5-yl-pyrimidin-2-yl)- | [MH]$^+$ 436 |
| E25 | (4-methylsulfonylphenyl-pyrimidin-2-yl)- MeSO$_2$- | [MH]$^+$ 472 |
| E26 | (4-cyanophenyl-pyrimidin-2-yl)- NC- | [MH]$^+$ 419 |

EXAMPLES 27 and 28 (E27-E28)

Examples 27-28 were prepared and isolated as for Example 1, from 1-isopropyl-4-(piperidine-4-carbonyl)-piperazine (D1)(0.239 g) and 4-fluoro-acetophenone at 120° C. for 2 h, followed by condensation of the product with the corresponding hydroxylamine hydrochloride in refluxing methanol for 1 h. Conversion to the HCl salts, by precipitation from ethyl acetate with 2N HCl in diethyl ether, and crystallisation from ethanol afforded the examples which displayed $^1$H NMR and mass spectral data that were consistent with structure.

| Example No | R | Mass Spectrum (ES$^+$) |
|---|---|---|
| E27 | MeO—N= | [MH]$^+$ 387 |
| E28 | EtO—N= | [MH]$^+$ 401 |

EXAMPLE 29

1-Isopropyl-4-{1-[2-chloro-4-(morpholino-carbonyl)-phenyl]-piperidine-4-carbonyl}-piperazine hydrochloride (E29)

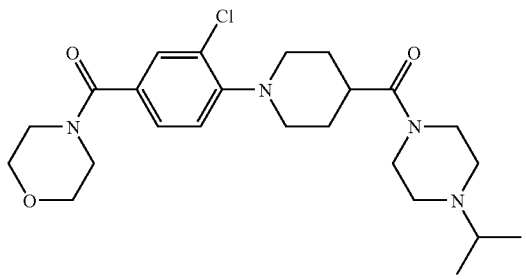

Step 1: 1-Isopropyl-4-[1-(2-chloro-4-chlorocarbonyl-phenyl)-piperidin-4-carbonyl]-piperazine hydrochloride 1-Isopropyl4-[1-(4-carboxy-phenyl)-piperidin-4-carbonyl]-piperazine hydrochloride (D9) (0.25 g) was dissolved in thionyl chloride (10 ml) and heated at reflux for 1.5 h. The reaction mixture was then evaporated to a minimum (co-evaporated with DCM, 3×10 ml) to give the subtitled compound as a yellow oil (0.25 g).

Step 2: 1-Isopropyl-4-{1-[2-chloro4-morpholino-carbonyl)-phenyl]-piperidine-4-carbonyl}-piperazine hydrochloride A stirred mixture of the product of E29, Step 1 (0.25 g) and diethylaminomethyl polystyrene (3.2 mmol/g, 0.45 g) in DCM (10 ml) at rt was treated with morpholine (0.035 g) and stirred for 16 h. The reaction mixture was chromatographed directly [silica gel, step gradient 0-10% MeOH (containing 10% 0.880 ammonia solution) in DCM]. Fractions containing the required product were evaporated, redissolved in DCM, treated with excess hydrogen chloride (1M solution in diethyl ether) and then concentrated and the residue crystallised from acetone to yield the title compound (E29) as a white powder (0.018 g). MS electrospray (+ion) 464 (MH$^+$). $^1$H NMR δ [DMSO-d6]: 10.30 (1H, s), 7.45 (1H, s), 7.32 (1H, d, J=8.0 Hz), 7.17 (1H, d, J=8.4 Hz), 4.55 (1H, m), 4.20 (1H, m), 3.62-3.28 (15H, m), 3.15-2.67 (5H, m), 1.77 (4H, m), 1.28 (6H, d, J=6.4 Hz).

EXAMPLE 30

1-Isopropyl-4-{1-[4-(morpholino-carbonyl)-phenyl]-piperidine-4-carbonyl}-piperazine hydrochloride (E30)

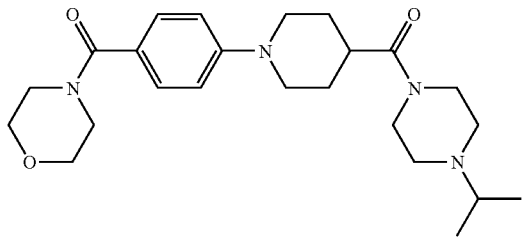

To a stirred solution of 1-isopropyl4-[1-(4-carboxy-phenyl)-piperidin4-carbonyl]-piperazine hydrochloride (D9) (0.25 g), morpholine (0.035 ml), HOBT (0.03 g), TEA (0.16 ml) in DCM (10 ml) was added EDC (0.10 g). DMF (2 ml)was added and the reaction stirred under argon overnight. The reaction mixture was then evaporated to a minimum and residue dissolved in DCM (50 ml) and washed with sodium hydrogen carbonate (3×50 ml) and then brine (50 ml). The organic layer was then dried (MgSO$_4$) and evaporated to give the free base product. Free base was converted to the HCl salt by dissolving in DCM (5 ml) and treating with excess 1HCl in diethyl ether, evaporated and then crystallised from acetone to give the title compound (E30) as a white solid (0.03 g). MS electrospray (+ve) 429 (MH$^+$). $^1$H NMR δ [DMSO-d6]: 10.85 (1H, s), 7.38 (2H, d, J=8.4 Hz), 7.08 (2H, m), 4.51 (1H, m), 4.22 (1H, m), 3.81 (2H, m), 3.68-3.35 (12H, m), 3.20-2.81 (6H, m), 1.74 (4H, m), 1.29 (6H, d, J=6.4 Hz).

EXAMPLE 31

1-Cyclopentyl-4-[1-(4cyano-phenyl)-piperidine-4-carbonyl]-piperazine hydrochloride (E31)

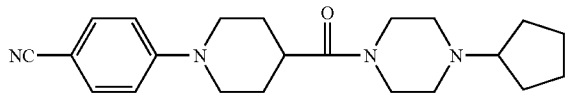

Potassium carbonate (0.8 g) was added to a stirred solution of 1-cyclopentyl-4-(piperidine-4-carbonyl)-piperazine di-hydrochloride (D5)(0.5 g) in dry DMSO (15 ml) followed by the addition of 4-benzonitrile (0.35 g). The reaction mixture was heated at 140° C. for 2 h. After cooling the reaction mixture was partitioned between H$_2$O/EtOAc (30:30 ml). The EtOAc layer was dried (MgSO$_4$) filtered and the filtrate was absorbed onto silica gel (4 g) and purified by chromatography [silica gel 0-10% MeOH (containing 10% 0.88 ammonia solution)/DCM]. The free base was dissolved in MeOH (3 ml) and treated with 1N ethereal HCl (2 ml). The solvents were removed by evaporation to give the title compound (E31) as a white solid (63 mg). $^1$H NMR δ [DMSO-d6]; 1.5-1.9 (12H, m), 2.9-3.06 (4H, m) 3.9-3.96 (2H, m), 4.18-4.45 (2H, m), 7.01 (2H, d J=9.2), 7.55 (2H,d J=9.2), 11.28 (1H, brs). LCMS electrospray(+ve) 356 (MH$^+$).

EXAMPLE 32

1-Cyclopentyl-4-[1-(5-cyano-pyridin-2.yl)-piperldine-4-carbonyl]-piperazine hydrochloride (E32)

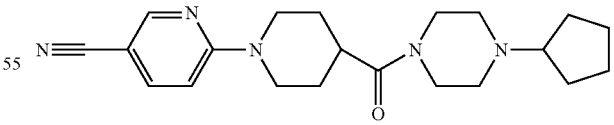

The title compound (E32) was prepared from 2-chloro-5-cyano-pyridine and 1-cyclopentyl-4-(piperidine-4-carbonyl)-piperazine di-hydrochloride (D5) according to the procedure described in Example 31. $^1$H NMR δ [DMSOd6]: 1.5 (4H, m), 1.67-1.88 (6H, m), 1.98-2.02 (2H, m), 2.87-2.97 (6H, m), 3.4-3.7 (4H, m), 4.17-4.7 (4H, m) 6.94 (1H, d, J=9 Hz), 7.8 (1H, d, J=9 Hz), 8.4 (1H, s) 11.5 (1H, brs). LCMS electrospray (+ve) 368 (MH+).

EXAMPLE 33

(2R,6S)-1-Cyclobutyl-4-[1-(4-cyanophenyl)-piperidine-4-carbonyl]-2,6-dimethylpiperazine hydrochloride (E33)

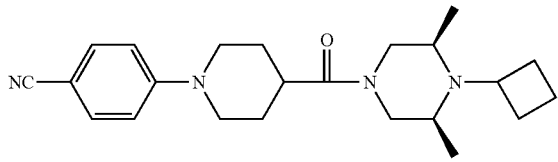

(2R,6S)-4-[1-(4-Cyanophenyl)-piperidine-4-carbonyl]-2,6-dimethylpiperazine hydrochloride (D13)(0.30 g), TEA (0.4 ml), cyclobutanone (0.13 g) and sodium triacetoxyborohydride (0.40 g) in DCM (5 ml) were heated to 100° C. in a microwave reactor for 5 min. The reaction mixture was then washed with saturated potassium carbonate solution (2×30 ml), and brine (30 ml). The organic layer was then dried (MgSO$_4$) and evaporated give the crude product which was purified by column chromatography [silica gel, step gradient 0-10% MeOH (containing 10% 0.880 ammonia solution) in DCM]. Fractions containing the required product were evaporated to give the free base compound which was converted to the HCl salt by redissolving in DCM and then treating with excess hydrogen chloride (1 M solution in diethyl ether), evaporating and then crystallising from acetone to give the title compound (E33) as a pale grey solid (0.053 g). MS electrospray (+ve) 381 (MH$^+$). $^1$H NMR δ [DMSO-d6]: 11.28 plus 10.10 (1H, m, rotomers), 7.59 (2H, d, J=8.4 Hz), 7.00 (2H, d, J=8.OHz), 4.31-3.73 (6H, m), 3.60-3.22 (3H, m), 2.97 (3H, m), 2.50-2.08 (4H, m), 1.78-1.61 (6H, m), 1.50-1.10 (6H, m).

EXAMPLE 34

1-Isopropyl-4-[1-phenyl-piperidine-4-carbonyl]-[1,4]-diazepane hydrochloride (E34)

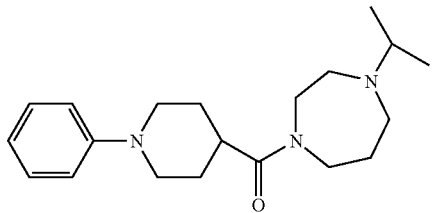

The title compound (E34) was prepared from 1-isopropyl-4-(piperidine-4-carbonyl)-[1,4]-diazepane (D8) and bromobenzene following the procedure of Example 45. LCMS electrospray (+ve) 330 (MH$^+$).

EXAMPLE 35

1-Isopentyl-4-[1-(5-cyano-pyridin-2-yl)-piperidine-4-carbonyl]-piperazine hydrochloride (E35)

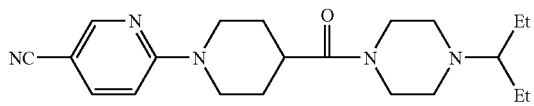

The title compound (E35) was prepared from N-isopentylpiperazine using the procedure described in Example 1. MS electrospray; (+ve ion) 370 (MH+).

EXAMPLE 36

1-Cyclobutyl-4-[1-(4-cyanophenyl)-piperldine-4-carbonyl]-[1,4]-diazepane hydrochloride (E36)

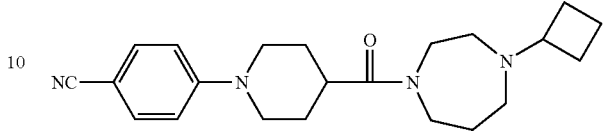

1-[1-(4-Cyanophenyl)piperidine-4-carbonyl]-[1,4]-diazepane hydrochloride (D4)(0.30 g) was dissolved in DCM (10ml). TEA (0.4 ml) and cyclobutanone (0.14 ml) were added and stirred for 5 min. Sodium triacetoxyborohydride (0.40 g) was then added and the reaction stirred at rt overnight. The reaction was then washed with aqueous saturated potassium carbonate solution (2×30 ml), brine (30 ml), dried (MgSO$_4$) and evaporated. The free base was redissolved in DCM and treated with excess hydrogen chloride (1M solution in diethyl ether) and concentrated to yield the title compound (E36) as a white solid (0.16 g). MS electrospray (+ve) 367 (MH$^+$). $^1$H NMR δ [DMSO-d6]: 10.95-10.78 (1H, m), 7.56 (2H, d, J=9.2 Hz), 7.02 (2H, d, J=8.8 Hz), 4.20-3.95 (3H, m), 3.62-3.39 (5H m), 3.07 (1H, m), 2.98-2.70 (5H, m), 2.49-2.01 (6H, m), 1.72-1.57 (6H, m).

EXAMPLE 37

1-Cyclobutyl-4-[1-(5-cyanopyridin-2-yl)-piperidine-4-carbonyl]-[1,4]-diazepane hydrochloride (E37)

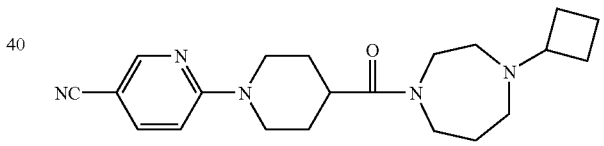

1-[1-(5-Cyanopyridin-2-yl)-piperidine-4-carbonyl]-[1,4]-diazepane hydrochloride (D14) (0.30 g) was dissolved in DCM (10 ml) and TEA (0.4 ml) was added followed by cyclobutanone (0.14 ml). The reaction was stirred for 5 min under argon and then sodium triacetoxyborohydride (0.41 g) was added and the reaction stirred at rt for 4 h. The reaction mixture was washed with saturated aqueous potassium carbonate (2×30 ml), saturated sodium hydrogen carbonate (2×50 ml) and brine (50 ml). The organic layer was then dried (MgSO$_4$) and evaporated to a crude which was purified by column chromatography [silica gel, step gradient 0-10% MeOH (containing 10% 0.880 ammonia solution) in DCM] to give the free base product which was converted to the HCl salt by redissolving in DCM and then treating with excess hydrogen chloride (1M solution in diethyl ether) and concentrating to yield the title compound (E37) as a pale yellow solid (0.047 g). MS electrospray (+ve) 368 (MH$^+$). $^1$H NMR δ [DMSO-d6]: 10.80-10.50 (1H, m), 8.47 (1H, s), 7.83 (1H, d, J=8.8 Hz), 6.95 (2H, d, J=8.8 Hz), 4.44 (2H, m), 4.05 (1H, m), 3.85-3.28 (6H, m), 3.07-2.72 (5H, m), 2.41-2.01 (6H, m), 1.82-1.41 (6H, m).

EXAMPLE 38

1-Isopropyl-4-[1-(4-cyanophenyl)-piperldine-4-carbonyl]-[1,4]-diazepane-hydrochloride (E38)

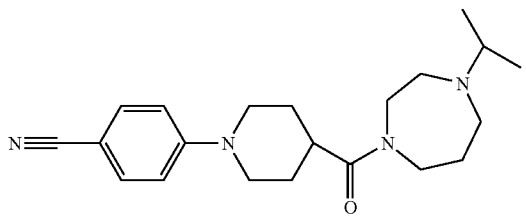

Triethylamine (0.18 ml) was added to a solution of 1-[1-(4-cyanophenyl)-piperidine-4-carbonyl]-[1,4]-diazepane hydrochloride (D4)(0.3 g) in dry DCM (15 ml) followed by the addition of acetone (0.15 g). The reaction was stirred at rt for 30 min followed by the addition of sodium triacetoxyborohydride (0.4 g). After 18 h 1N NaOH (2 ml) was added and stirring continued for a further 15 min. The reaction was then washed with water and the DCM layer was separated, dried ($MgSO_4$), absorbed onto silica gel (4 g) and purified by chromatography [silica gel 0-10% MeOH (containing 10% 0.88 ammonia solution)/DCM]. The free base was dissolved in MeOH (3 ml) and treated with 1N ethereal HCl (2 ml). The solvent was removed by evaporation to give the title compound (E38) as a white solid (0.1 g). $^1$H NMR δ [DMSO-d6]; 1.27 (6H, d J=6.5 Hz), 1.58 (2H, m), 1.74 (2H, m), 2.08 (1H, m), 2.32 (1H, m), 2.75-3.25 (6H, m), 3.35-3.76 (6H, m), 3.9-4.08 (2H, m), 7.0 (2H, d, J=8.8), 7.54 (2H, d J=8.8), 10.38-10.58 (1H, m). LCMS electrospray (+ve) 355 (MH$^+$).

EXAMPLE 39

1-Isopropyl-4-[1-(4-cyano-2,5-difluorophenyl)-piperidine-4-carbonyl]-[1,4]-diazepane hydrochloride (E39)

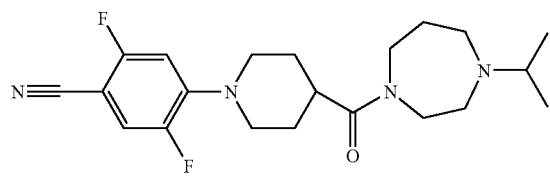

$K_2CO_3$ (0.5 g) eas added to a solution of 1-isopropyl-4-(piperidine-4-carbonyl)-[1,4]-diazepane (D8)(0.2 g) in dry DMSO (2 ml), and the resulting mixture was stirred at rt for 15 min, followed by the addition of 2,4,5-trifluorobenzonitrile (0.24 g) in dry DMF (1 ml). The reaction was then heated at 140° C. for 2 h before cooling to rt. Excess potassium carbonate was removed by filtration and the crude reaction mixture was purified first by adding the crude reaction to a Varian 10 g SCX column and eluting with MeOH (40 ml), then eluting with 10% 0.88 ammonia solution in MeOH (20 ml) which was evaporated to afford a residue that was further purified using a Waters mass directed auto preparative HPLC. The purified fractions were combined and the aqueous solvents were removed by evaporation and the residue re-dissolved in MeOH (2 ml) and treated with 1N ethereal HCl (1 ml) which gave a white solid which was washed with diethyl ether to give the title compound (E39)(34 mg). $^1$H NMR δ [MeOH-d4]; 1.37 (6H, m), 1.87 (4H, m), 2.19-2.29 (2H, m), 2.94-3.00 (3H, m), 3.29-3.3 (2H, m), 3.53-3.58 (7H, m), 3.86-3.98 (1H, m), 4.04-4.1 (1H, m), 6.9 (1H, dd, J=111.6 Hz), 7.4 (1H, dd, J=12.4hZ). LCMS electrospray (+ve) 391 (MH$^+$).

EXAMPLE 40

1-Isopropyl-4-[1-(4-cyano-3-chlorophenyl)-piperldine-4-carbonyl]-[1,4]-diazepane hydrochloride (E40)

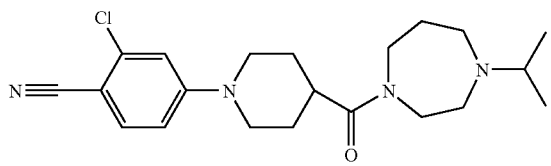

The title compound (E40) was prepared using 2-chloro-4-fluorobenzonitrile and the procedure described in Example 39. $^1$H NMR δ [MeOH-d4]; 1.37 (6H, m), 1.78-1.9 (4H, m), 2.29 (2H, m), 2.99-3.00 (3H, m), 3.04-3.31 (2H, m), 3.47-3.58 (5H, m), 3.87 (1H, m), 3.97-4.07 (2H, m), 4.07-4.09 (1H), 6.96 (1H, d, J=8.8 Hz), 7.08 (1H, d, J=2 Hz), 7.51 (1H, J=8.8 Hz). LCMS electrospray (+ve) 389 (MH$^+$).

EXAMPLE 41

1-Isopropyl-4-[1-(4-cyano-3-fluoro-phenyl)-piperidine-4-carbonyl]-[1,4]-diazepane hydrochloride (E41)

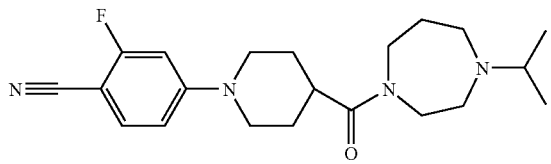

The title compound (E41) was prepared using 2,4-difluorobenzonitrile and the procedure described in Example 39. $^1$H NMR δ [MeOH-d4]: 1.37 (6H, m), 1.9 (4H, m), 2.19-2.33 (2H, m), 2.89-2.98 (3H, m), 3.27-3.3 (2H, m), 3.5-3.78 (6H, m), 3.80-3.90 (1H, m), 4.07-4.15 (1H, m), 4.07-4.09 (1H), 7.15 (1H, t, J=8.4 Hz), 7.44 (2H, dd J=6.4 Hz). LCMS electrospray (+ve) 373 (MH$^+$).

EXAMPLE 42

1-Isopropyl-4-[1-(4-cyano-2,6-difluoro-phenyl)-piperidine-4-carbonyl]-[1,4]-diazepane hydrochloride (E42)

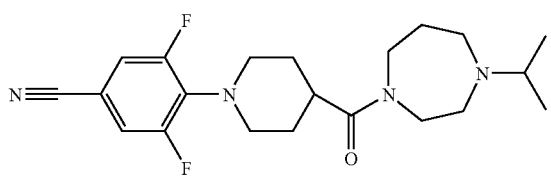

The title compound (E42) was prepared using 3,4,5-trifluorobenzonitrile and the procedure described in Example 39. $^1$H NMR δ [MeOH-d4]: 1.37 (6H, m), 1.78-1.92 (4H, m), 2.15-2.38 (2H, m), 2.80-2.93 (1H, m), 3.17-3.27 (4H, m), 3.4-3.78 (7H, m), 3.80-3.90 (1H, m), 4.07-4.15 (1H, m), 7.35 (2H, dd, J=2.4 Hz). LCMS electrospray (+ve) 391 (MH$^+$)

EXAMPLE 43

1-Isopropyl-4-[1-(4-cyano-2-fluoro-phenyl)-piperidine-4-carbonyl]-[1,4]-diazepane hydrochloride (E43)

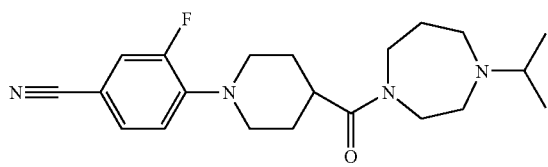

The title compound (E43) was prepared using 3,4-difluorobenzonitrile and the procedure described in Example 39. $^1$H NMR δ [MeOH-d4]: 1.37.(6H, m), 1.73-1.89 (4H, m), 2.18-2.37 (2H, m), 2.98-3.08 (3H, m), 3.15-3.27 (2H, m), 3.48-3.78 (5H, m), 3.80-3.90 (1H, m), 3.98-4.12 (2H, m), 4.05-4.12 (1H), 6.7-6.8 (2H, m), 7.45 (1H, t, J=8 Hz). LCMS electrospray (+ve) 373 (MH$^+$).

EXAMPLE 44

1-Isopropyl-4-[1-(4-cyano-3-trifluoromethyl-phenyl)-piperidine-4-carbonyl]-[1,4]-diazepane hydrochloride (E44)

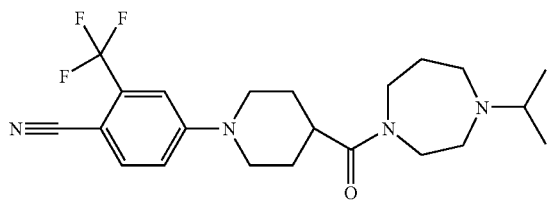

The title compound (E44) was prepared using 2-trifluoromethyl-4-fluorobenzonitrile and the procedure described in Example 39. $^1$H NMR δ [MeOH-d4]: 1.38 (6H, m), 1.75-1.91 (4H, m), 2.23-2.37 (2H, m), 2.80-3.08 (4H, m), 3.3-4.08 (1 OH, m), 7.18 (1H, d, J=8.8 Hz), 7.25 (1H, d, J=2.4), 7.68 (1H, d, J=8.8 Hz). LCMS electrospray (+ve) 423 (MH$^+$).

EXAMPLE 45

1-Isopropyl-4-[1-(4-trifluoromethyl-phenyl)-piperidine-4-carbonyl]-[1,4]-diazepane hydrochloride (E45)

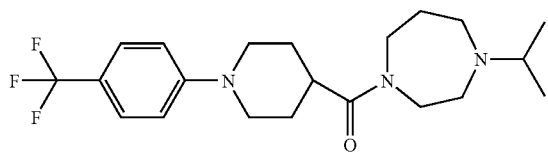

To 4-trifluoromethyl-iodobenzene (0.2 g) under argon in dry degassed dioxane (1.5 ml) was added bis(dibenzylideneacetone)palladium (0.02 g) followed by 2-dicyclohexylphosphine-2'-(N,N-dimethylamino)-biphenyl (0.055 g). After 15 min this solution was added to 1-isopropyl-4-(piperidine-4-carbonyl]-[1,4]-diazepane (D8)(0.15 g) as a slurry in dry degassed dioxane (1.5 ml) under argon. This was followed by addition of sodium-t-butoxide (0.06 g) and heating to 100° C. for 2 h. After cooling, saturated ammonium chloride solution (10 ml) was added along with EtOAc (20 ml). The reaction was filtered and washed with brine (2×) before being extracted with 1N HCl and then neutralised with potassium carbonate solution and back extracted into EtOAc. Concentration to low volume and addition of 2N HCl in diethyl ether caused the title hydrochloride salt to precipitate. Decantation of the supernatant and repeated trituration of the residue with diethyl ether afforded crude product that was crystallised from acetonitrile to afford the title compound (E45)(0.078 g). $^1$H NMR δ [MeOH-d4]: 1.38 (6H, m), 2.0-2.34 (6H, m), 2.86-4.11 (14H, m), 7.5-7.6 (2H, m) and 7.71-7.77 (2H, m). LCMS electrospray (+ve) 398 (MH$^+$).

EXAMPLES 46-69 (E46-E69)

Example 46 and Examples 63-69 were prepared from either 1-isopropyl-4-(piperidine4-carbonyl)-[1,4]-diazepane (D8) or 1-cyclobutyl-4-(piperidine-4-carbonyl)-[1,4]-diazepane (D10) and the appropriate aryl fluoride using the procedure described in Example 39. Examples 47-62 were prepared by coupling 1-isopropyl-4-(piperidine-4-carbonyl)-[1,4]-diazepane (D8) with the appropriate aryl halide (bromide or iodide) using the conditions described in Example 45. The products displayed $^1$H NMR and mass spectral data that were consistent with structure.

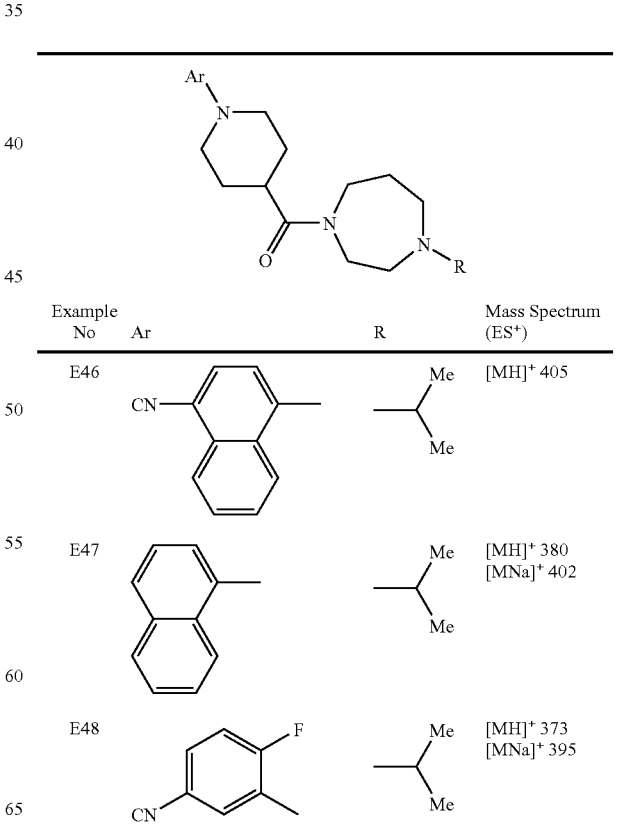

| Example No | Ar | R | Mass Spectrum (ES$^+$) |
|---|---|---|---|
| E46 | CN-naphthyl | Me, Me (isopropyl) | [MH]$^+$ 405 |
| E47 | naphthyl | Me, Me (isopropyl) | [MH]$^+$ 380 [MNa]$^+$ 402 |
| E48 | F, CN, Me-phenyl | Me, Me (isopropyl) | [MH]$^+$ 373 [MNa]$^+$ 395 |

-continued

![structure with Ar-N-piperidine-C(O)-N-diazepane-N-R]

| Example No | Ar | R | Mass Spectrum (ES+) |
|---|---|---|---|
| E49 | 4-isopropylphenyl | iPr (Me/Me) | [MH]+ 372 [MNa]+ 394 |
| E50 | 3-isopropoxyphenyl | iPr | [MH]+ 388 [2MNa]+ 797 |
| E51 | 3-CF3O-phenyl | iPr | [MH]+ 414 [MNa]+ 436 |
| E52 | 4-F-phenyl | iPr | [MH]+ 348 [MNa]+ 370 |
| E53 | 3-Cl-4-F-phenyl | iPr | [MH]+ 382/384 [MNa]+ 404/406 |
| E54 | 3,4-diCl-phenyl | iPr | [MH]+ 398/400/402 [MNa]+ 420/422 |
| E55 | 3,5-diCl-phenyl | iPr | [MH]+ 398/400/402 |
| E56 | 4-CF3O-phenyl | iPr | [MH]+ 414 |
| E57 | 4-MeO-phenyl | iPr | [MH]+ 360 [2MNa]+ 741 |
| E58 | 3-Cl-4-MeO-phenyl | iPr | [MH]+ 394/396 [MNa]+ 416/418 |
| E59 | 4-CHF2O-phenyl | iPr | [MH]+ 396 [MNa]+ 418 |
| E60 | 3-CHF2O-phenyl | iPr | [MH]+ 396 [MNa]+ 418 |
| E61 | 4-PhO-phenyl | iPr | [MH]+ 422 [2MNa]+ 865 |
| E62 | 6-MeO-pyridin-3-yl | iPr | [MH]+ 361 [MNa]+ 383 |
| E63 | 4-CN-2,3-diF-phenyl | iPr | [MH]+ 391 |
| E64 | 4-CN-3-Cl-phenyl | iPr | [MH]+ 389 |
| E65 | 4-CN-3-Cl-phenyl | cyclobutyl | [MH]+ 401/403 |
| E66 | 4-CN-2-Cl-phenyl | cyclobutyl | [MH]+ 401/403 |
| E67 | 4-CN-2-F-phenyl | cyclobutyl | [MH]+ 385 |

-continued

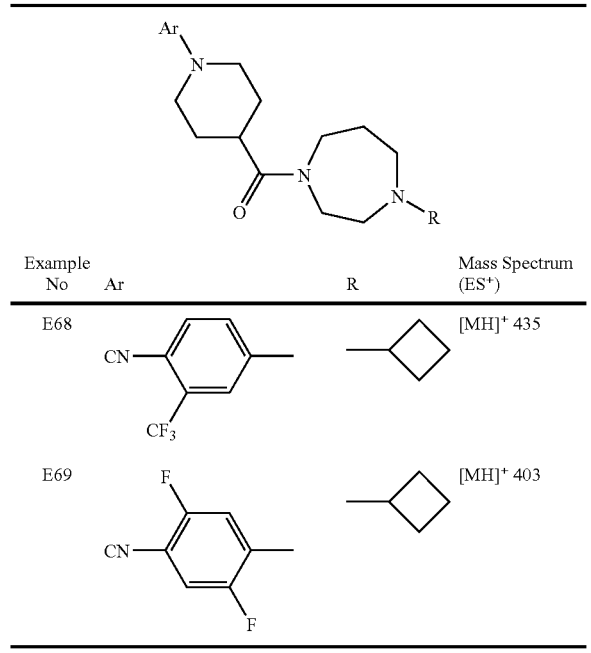

| Example No | Ar | R | Mass Spectrum (ES+) |
|---|---|---|---|
| E68 | CN— with CF3 | cyclobutyl | [MH]+ 435 |
| E69 | F, CN, F substituted | cyclobutyl | [MH]+ 403 |

EXAMPLE 70

(S)-1-Isopropyl-4-[1-(4-cyanophenyl)-piperldine-4-carbonyl]-2-methylpiperazine hydrochloride (E70)

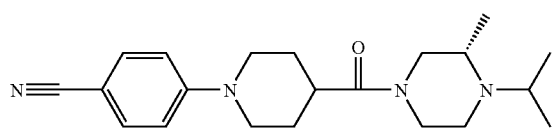

A mixture of (S)1-[1-(4-cyanophenyl)-piperidine-4-carbonyl]-3-methylpiperazine (D15) (194 mg), potassium carbonate (172 mg) and 2-iodopropane (0.06 ml) in MeCN (4 ml) was heated in a microwave oven at 150° C. for 10 min. Further 2-iodopropane (0.06 ml) was added and the reaction re-microwaved at 170° C. for 10 min, filtered and evaporated. The residue was flash chromatographed [silica gel, step gradient 2-7% MeOH (containing 10% 0.880 ammonia solution) in DCM]. Fractions containing the required product were evaporated to give the free base compound which was converted to the HCl salt by redissolving in DCM and then treating with excess hydrogen chloride (4M solution in 1,4-dioxan), evaporating and then crystallising from EtOH/diethyl ether to give the title compound (E70) as a white solid (105 mg). MS electrospray (+ve) 355 (MH+). $^1$H NMR δ [DMSO-d6]: 10.95-11.25 (1H, m), 7.56 (2H, d, J=9 Hz), 7.02 (2H, d, J=9 Hz), 4.28-2.68 (13H, m), 1.80-1.45 (4H, m), 1.38 (3H, s), 1.35 (3H, s), 1.12 (3H, d, J=6.5 Hz).

EXAMPLES 71 and 72 (E71 and E72)

Examples 71 and 72 (E71-E72) were prepared from (S)-1-[1-(4-cyanophenyl)-piperidine-4-carbonyl]-3-methylpiperazine (D15) by alkylation with ethyl iodide and cyclobutyl bromide respectively, using N,N-diisopropylethylamine as base in acetonitrile.

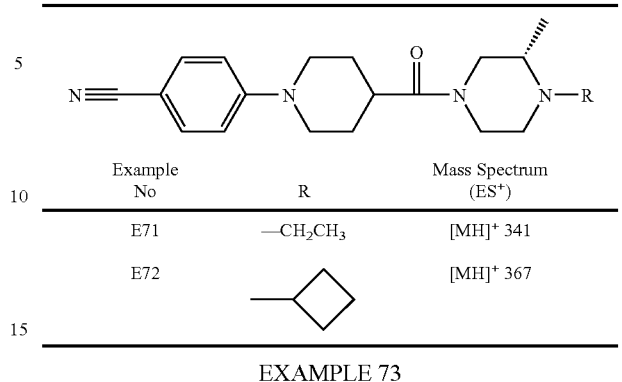

| Example No | R | Mass Spectrum (ES+) |
|---|---|---|
| E71 | —CH$_2$CH$_3$ | [MH]+ 341 |
| E72 | cyclobutyl | [MH]+ 367 |

EXAMPLE 73

(R)-1-Isopropyl-4-[1-(4-cyanophenyl)-piperidine-4-carbonyl]-2-methylpiperazine hydrochloride (E73)

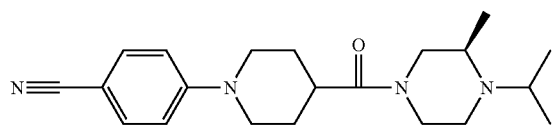

The title compound E73 was prepared from (R)-1-[1-(4-cyanophenyl)-piperidine-4-carbonyl]-3-methylpiperazine (D16) using the procedure described in E70. MS electrospray (+ve) 355 (MH+).

EXAMPLE 74

(2R, 5S) and (2S, 5R)-1-Isopropyl-4-[1-(4-cyanophenyl)-piperidine-4-carbonyl]-2,5-dimethylpiperazine hydrochloride (E74)

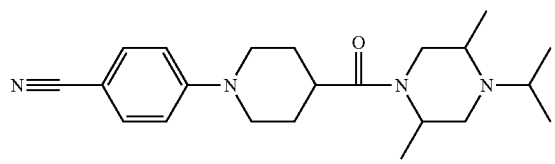

The title compound (E74) was prepared from (2R, 5S) and (2S, 5R)-1-[1-(4-cyanophenyl)-piperidine-4-carbonyl]-2,5-dimethylpiperazine (D17) by alkylation with isopropyl iodide using N,N-diisopropylethylamine as base in acetonitrile. MS electrospray (+ve) 369 (MH+).

EXAMPLE 75

(2S, 6S)-1-Ethyl-4-[1-(4-cyanophenyl)-piperidine-4-carbonyl]-2,6-dimethyl piperazine hydrochloride (E75)

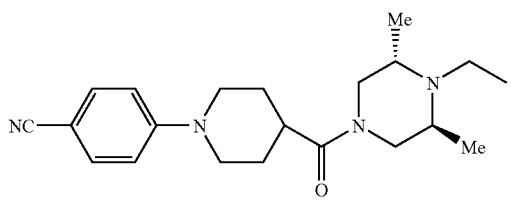

(3S, 5S)-1-[1-(4-Cyanophenyl)-piperidine-4-carbonyl]-3,5-dimethylpiperazine (D18) (0.135 g), anhydrous potassium carbonate (0.114 g), ethyl iodide (0.066 ml) and acetonitrle (2 ml) were heated in the microwave apparatus at 120° C. for 20 min, and allowed to cool. The inorganics were filtered and the filtrate was evaporated to a gum which was chromatographed on silica gel eluting with 0-5% methanolic ammonia (2M) in DCM. The resulting free base was dissolved in DCM (3 ml), and treated with HCl/Et$_2$O (1.0M, 3 ml) and the resulting suspension was evaporated to dryness by blowing down with a gentle stream of argon to give the title compound (E75) as an off-white solid (0.12 g).

$^1$H NMR δ [DMSO-d6/D$_2$O]: 1.08-1.34 (9H, m), 1.47-1.77 (4H, br. m), 2.99 (4H, m), 3.18-3.29 (1H, m), 3.37-3.45 (1H, m), -3.46-3.63 (1H, br. m, partly obscured by H$_2$O signal), 3.68-3.83 (2H, br. m), 3.93-3.96 and 4.17-4.29 (2×m, total of 4H), 7.01 (2H, d, J=9 Hz), 7.56 (2H, d, J=9 Hz); LCMS electrospray (+ve) 355 (MH$^+$).

EXAMPLE 76

(S)-1-Isopropyl-4-[1-(4-cyanophenyl)-piperidine-4-carbonyl]-3-methylpiperazine hydrochloride (E76)

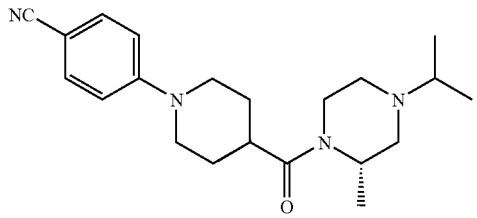

(S)-1Isopropyl4-(piperidine-4-carbonyl)-3-methylpiperazine dihydrochloride (D23) (0.10 g), 4-fluorobenzonitrile (0.12 g) and potassium carbonate (0.18 g) in DMSO (4 ml) were heated at 140° C. for 6 h. The reaction mixture was then evaporated to a minimum and redissolved in methanol and loaded onto SCX silica (10 g). The SCX cartridge was washed with methanol (80 ml) and then eluted with 2M ammonia in methanol (80 ml) to afford a crude product that was purified by Waters Mass Directed Auto Preparative HPLC (eluent: 0.1% formic acid in water and 0.1% formic acid acetonitrile; gradient 10-100%). Fractions containing the required product were combined to give the product as the formate salt which was converted into the HCl salt in DCM/ethereal 1N HCl (1 ml). The solvents were removed by evaporation (co-evaporated from acetone 3 times) to give the title compound (E76) as a white solid (47 mg). $^1$H NMR δ [DMSO-d6]: 1.30 (7H, m), 1.40-1.81 (6H, m), 2.78-3.21 (6H, m), 3.33 (2H, m), 3.42-3.83 (1H plus water), 3.97 (2H, m), 4.11 plus 4.45 (1H, m, rotamers), 4.58 plus 4.78 (1H, m, rotamers), 7.01 (2H, d, J=8.8 Hz), 7.56 (2H, d, J=8.8 Hz). LCMS electrospray (+ve) 355 (MH$^+$).

EXAMPLE 77

(S)-1-Cyclobutyl-4-[1-(4-cyanophenyl)-piperidine-4-carbonyl]-3-methylpiperazine hydrochloride (E77)

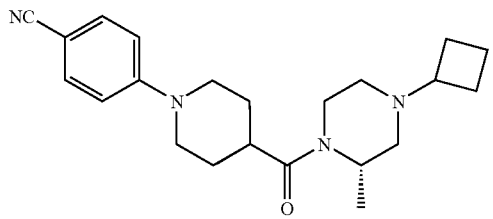

The title compound (E77) was prepared from (S)-1-cyclobutyl)4-(piperidine4-carbonyl)-3-methylpiperazine dihydrochloride (D25) and 4-fluorobenzonitrile using the method of Example 76. LCMS electrospray (+ve) 367 (MH$^+$).

EXAMPLE 78

(S)-1-Isopropyl-4-[1-(6-cyanopyridin-3-yl)-piperidine-4-carbonyl]-2-methyl piperazine hydrochloride (E78)

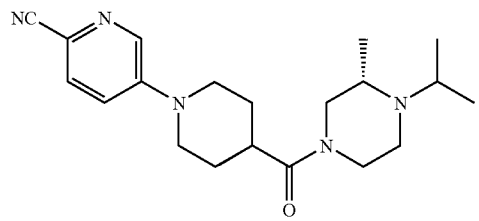

(S)-1-Isopropyl-4-(piperidine-4-carbonyl)-2-methylpiperazine dihydrochloride (D29) (0.2 g), 2-cyano-5-bromopyridine (0.14 g) and potassium carbonate (0.22 g) were stirred in DMSO (4 ml) at 120° C. for 2 h. After cooling, the potassium carbonate was filtered off and the DMSO filtrate was diluted with MeOH (20 ml). The crude mixture was poured onto a 10 g isolute SCX column which was washed first with MeOH (50 ml) and then eluted with 10% ammonia in MeOH (50 ml). The product was further purified by column chromatography (silica gel, step gradient 0-10% MeOH (containing 10% 0.88 ammonia solution) in DCM]. Fractions containing the required product were evaporated to give the free base which was dissolved in DCM (10 ml) and treated with 1N HCl in diethyl ether to give the title compound (E78) as a light yellow solid (30 mg). LCMS electrospray (+ve) 356.(MH$^+$).
$^1$H NMR [DMSO-d6]δ: 1.09 (3H, d, J=6.4 Hz), 1.33-1.35 (6H, d, J=6.5 Hz), 1.54-1.74 (4H, m), 2.98-3.16 (5H, m), 3.23-3.68 (3H, m), 3.83-4.45 (5H, m), 7.37 (1H, dd, J=8.8 Hz), 7.72 (1H, d, J=8.8 Hz), 8.4(1H, d, J=2.8 Hz), 10.9 (1H, bs)

EXAMPLE 79

(S)-1-Isopropyl4-[1-(6-trifluoromethylpyridin-3-yl)-piperldinearbonyl]-2-methyl piperazine hydrochloride (E79)

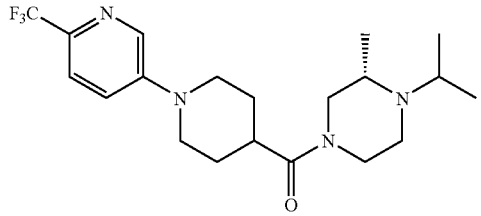

(S)-1-Isopropyl-4-(piperidine-4-carbonyl)-2-methylpiperazine dihydrochloride (D29) (1.5 g) in water 5 ml was treated with solid K$_2$CO$_3$. The resulting oil was extracted with EtOAc (25 ml), dried (MgSO$_4$) and evaporated to give (S)-1-isopropyl-4-(piperidine4-carbonyl)-2-methyl piperazine as the free base (1 g). 5-Bromo-2-trifluoromethylpyridine (F. Cottet and M. Schlosser, Eur. J. Org. Chem., 2002, 327-330) (0.13 g) in degassed dry dioxan (3 ml) was charged with tris(dibenzylideneacetone) dipalladium(0)(30mg) and 2-dicyclohexylphosphino-2'-(N,N-dimrethylamino)biphenyl (60 mg). The dark suspension was stirred at rt for 20 min under a blanket of argon. To this reaction a solution of (S)-1-isopropyl-4-(piperidine-4-carbonyl)-2-methyl piperazine (0.15 g) in degassed dioxan (2 ml) was added followed by sodium tert-butoxide (0.11 g). The reaction mixture was stirred at 90° C. for 2 h. After allowing the reaction to cool to rt MeOH (20 ml) was added and the crude reaction mixture was poured onto a 10 g isolute SCX column which was washed with MeOH (50 ml) and then eluted with 10% ammonia in MeOH (50 ml). The product was further purified by column chromatography [silica gel, step gradient 0-10% MeOH (containing 10% 0.88 ammonia solution) in DCM]. Fractions containing the required product were evaporated to give the free base which was dissolved in DCM (10 ml) and treated with 1N HCl in diethyl ether to give the title compound (E79) as a solid (150 mg). LCMS electrospray (+ve) 399 (MH$^+$). $^1$H NMR [DMSO-d6]δ: 1.09 (3H, d, J=6.4 Hz), 1.33-1.35 (6H, m), 1.54-1.74 (4H, m), 2.98-3.16 (5H, m), 3.23-3.68 (3H, m), 3.83-4.45 (5H, m) 7.44 (1H, dd, J=8.8 Hz), 7.63 (1H, d, J=8.8 Hz), 8.4 (1H, d, J=2.8 Hz), 10.55 (1H, bs).

EXAMPLE 80

(S)-1-Isopropyl-4-[1-(2-cyanopyridin-4-yl)-piperldine-4-carbonyl]-2-methyl piperazine hydrochloride (E80)

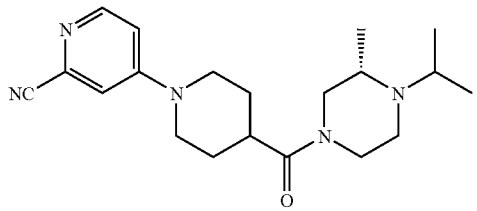

The title compound (E80) was prepared by reacting (S)-1-isopropyl-4-(piperidine-4-carbonyl)-2-methylpiperazine dihydrochloride (D29) and 4-chloro-2-cyanopyridine (T. Sakamoto, S-l. Kaneda, S. Nishimura and H. Yamanaka, Chem. Pharm. Bull., 1985, 33(2), 565-571) at 140° C. using the method of Example 78. LCMS electrospray (+ve) 356 (MH$^+$).

EXAMPLE 81

1-Isopropyl-4-[1-(2-methyl-quinolin-6-yl)-piperidine-4-carbonyl]-[1,4]-diazepane hydrochloride (E81)

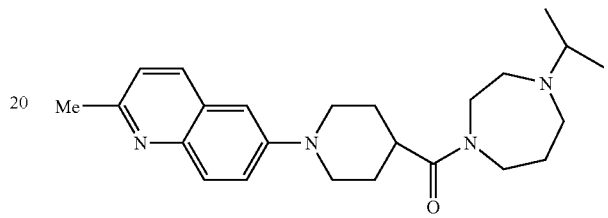

The title compound (E81) was prepared from 1-isopropyl-4-(piperidine-4-carbonyl)-[1,4]-diazepane (D8) and 6-bromo-2-methylquinoline using the procedure described in Example 89. LCMS electrospray (+ve) 395 (MH$^+$).

EXAMPLES 82-85 (E82-E85)

Examples 82-85 were prepared in a similar manner to Example 2 by reacting (S)-1-isopropyl4-(piperidine-4-carbonyl)-2-methylpiperazine dihydrochloride (D29) and the corresponding aryl fluoride in DMSO in the presence of potassium carbonate. The products displayed $^1$H NMR and mass spectral data that were consistent with structure.

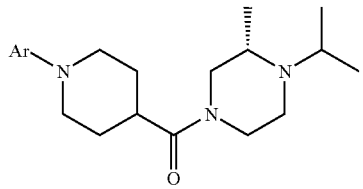

| Example No | Ar | Aryl Fluoride | Mass Spectrum (ES$^+$) |
|---|---|---|---|
| E82 | CN-⌬-Me (with F) | CN-⌬-F (with F) | [MH]$^+$ 373 |
| E83 | O=C(Me)-⌬-Me | O=C(Me)-⌬-F | [MH]$^+$ 372 |

-continued

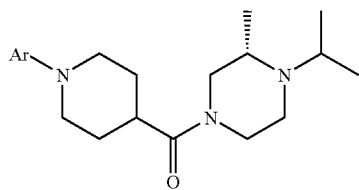

| Example No | Ar | Aryl Fluoride | Mass Spectrum (ES+) |
|---|---|---|---|
| E84 | (4-methylphenyl cyclopropyl ketone) | (4-fluorophenyl cyclopropyl ketone) | [MH]+ 398 |
| E85 | (4-methylphenyl cyclobutyl ketone) | (4-fluorophenyl cyclobutyl ketone) | [MH]+ 412 |

EXAMPLE 86

(S)-1-Isopropyl-4-[1-(5-cyanopyridin-2-yl)-piperidine4-carbonyl]-2-methyl piperazine hydrochloride (E86)

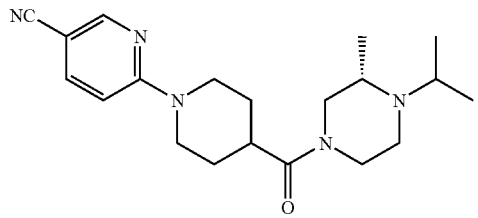

1-(5-Cyano-pyridin-2-yl)-piperidinecarboxylic acid (D11)(0.2 g) in DMF (20 ml) was treated with EDC (0.33 g) followed by HOAt (10 mg). After 5 min, (S)-1-isopropyl-2-methylpiperazine hydrochloride (D27)(0.12 g) was added followed by N,N-diisopropylethylamine (0.3 ml) and the mixture was stirred at rt overnight. The DMF was removed by evaporation and the residue was partitioned between water (20 ml) and EtOAc (20 ml). The EtOAc layer was dried (MgSO$_4$) and filtered, and the filtrate was absorbed onto silica gel (2 g) and then purified by column chromatography [silica gel, step gradient 0-10% MeOH (containing 10% 0.88 ammonia solution) in DCM]. The fractions containing the product were evaporated and the free base was dissolved in MeOH (1 ml) and treated with ethereal HCl (1 ml) to give the title compound (E86) as a white solid (0.1 g). LCMS electrospray (+ve) 356 (MH+). $^1$H NMR δ [DMSO-d6]:1.12 (3H, d, J=6.4 Hz), 1.33-1.35 (6H, d, J=6.8 Hz), 1.45-1.75 (4H, m), 2.98-3.16 (4H, m), 3.28-3.48 (2H, m), 3.81-3.84 (1H, m), 4.19-4.23 (1H, m), 4.33-4.43 (5H, m), 6.93 (1H, d, J=9.2 Hz), 7.72 (1H, d, J=9.2 Hz), 8.46 (1H, d, J=2.0Hz), 10.9 (1H, br. s)

EXAMPLE 87

(S)-1-Isopropyl-4-[1-(5-trifluoromethyl-pyrazin-2-yl)-piperidine-4-carbonyl]-2-methyl piperazine hydrochloride (E87)

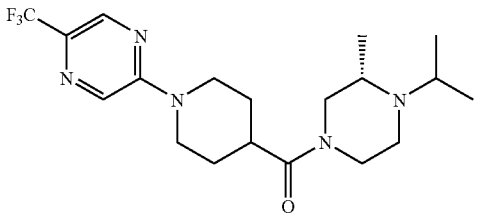

(S)-1-Isopropyl-4-(piperidine-4-carbonyl)-2-methyl piperazine (free base compound from D29)(0.14 g) 2-chloro-5-trifluoromethylpyrazine (D31)(0.1 g) and potassium carbonate (0.15 g) were stirred in DMSO (1.5 ml) at 120° C. for 5 min in a microwave reactor. The reaction was worked up as described for Example 78 and the purified free base was dissolved in MeOH (2 ml) and treated with 1N ethereal HCl solution (2 ml) to give the title hydrochloride salt (E87) as a white solid (50 mg). LCMS electrospray (+ve) 400 (MH+). $^1$H NMR δ [MeOH-d4]: 1.29 (3H, d, J=6.4 Hz), 1.33-1.35 (6H, m), 1.6-1.95 (4H, m), 2.98-3.2 (5H, m), 3.40-3.68 (3H, m), 3.93-4.80 (5H, m), 8.29 (1H, s), 8.36(1H, s).

EXAMPLE 88

(S)-1-Isopropyl-4-[1-(6-trifluoromethyl-pyridazin-3-yl)-piperidine-4-carbonyl]-2-methyl piperazine hydrochloride (E88)

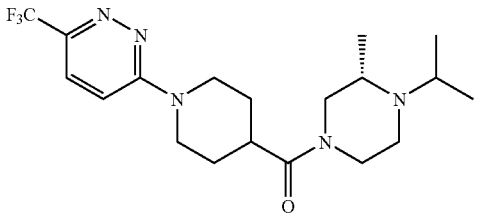

(S)-1-Isopropyl-4-(piperidine-4-carbonyl)-2-methylpiperazine (free base compound from D29)(0.10 g), 3-chloro-6-trifluoromethyl-pyridazine (A. J. Goodman, S. P. Stanforth and B. Tarbit, Tetrahedron, 1999, 55(52), 15067-15070) (0.071 g) and potassium carbonate (0.1 g) were stirred in DMSO (1.5 ml) at 120° C. for 5 min in a microwave reactor. The reaction was worked up as described for Example 78 and the purified free base was dissolved in MeOH (2 ml) and treated with 1N ethereal HCl solution (2 ml) to give the title hydrochloride salt (E88) as a white solid (92 mg). LCMS electrospray (+ve) 400 (MH$^+$). $^1$H NMR δ [DMSO-d6]:1.29 (3H, d, J=6.4 Hz), 1.34-1.39 (6H, m), 1.47-1.85 (4H, m), 2.75-3.2 (5H, m), 3.30-3.90 (4H, m), 4.6 (4H, m), 7.47 (1H, d, J=9.6 Hz), 7.80 (1H, d, J=9.6 Hz), 11.15 (1H, bs).

EXAMPLE 89

(S)-1-Isopropyl-4-[1-(2-trifluoromethyl-pyrimidin-5-yl)-piperidine-4-carbonyl]-2-methyl piperazine hydrochloride (E89)

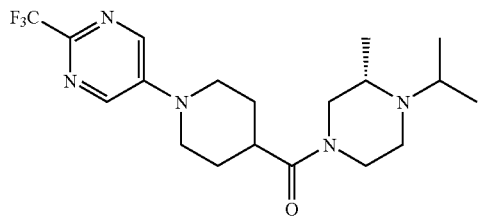

Tris(dibenzylideneacetone)dipalladium(0)(30 mg) and 2-dicyclohexylphosphino-2'-(N,N-dimethylamino)biphenyl (60 mg) were added to a solution of (S)-1-isopropyl4-(piperidine-4-carbonyl]-2-methyl piperazine (free base compound from D29)(0.134 g) and 5-bromo-2-trifluromethylpyrimidine (D30)(0.12 g) in degassed dioxane (3 ml). This was followed by the addition of sodium-t-butoxide (0.1 g). The reaction was carried out in a Personal Chemistry microwave reactor at 120° C. for 5 min. After cooling the reaction mixture was diluted with methanol (10 ml), the solids were filtered off and the filtrate was applied to an SCX resin column. Initial elution with methanol was followed by elubon with methanolic ammonia (2M). The ammoniacal eluates were concentrated to a gum and further purified by silica gel chromatography, eluting with 0-10% methanolic ammonia (2M) in DCM. Evaporation of the appropriate fractions gave the free base which was dissolved in DCM (3 ml) and treated with ethereal 1M HCl (2 ml) to give the title compound (E89) as a light yellow solid (56 mg). MS electrospray (+ve) 400 (MH$^+$). $^1$H NMR δ [MeOH-d4]: 1.28-1.29 (3H, m), 1.4-1.5 (8H, m), 1.8-1.9 (4H, m), 2.98-3.2 (3H, m), 3.45-3.57 (3H, m), 4.0-4.08 (3H, m), 4.35-4.45 (1H, m), 4.6-4.78 (1H, s), 8.5 (2H, s).

EXAMPLE 90

1-Isopropyl-4-{1-[4-(5-phenyl-1,3,4-oxadiazol-2-yl)phenyl]-piperidine-4-carbonyl} piperazine hydrochloride (E90)

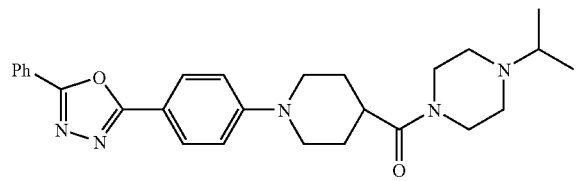

To 1-bromo-4-[5-phenyl-1,3,4-oxadiazol-2-yl]benzene (0.1 g) under argon in dry degassed dioxane (1.9 ml) was added bis(dibenzylideneacetone)palladium (0.008 g) followed by 2-dicyclohexylphosphino-2'-(N,N-dimethylamino) biphenyl (0.023 g). To this solution after 15 min was added 1-isopropyl-4-(piperidine-4-carbonyl)-piperazine (D1) (0.072 g) as a solution in dry degassed dioxane (1.9 ml) under argon. This was followed by addition of sodium-t-butoxide (0.025 g) and heating to 100° C. for 3 h. After cooling, the solids were filtered off and the filtrate was applied to an SCX resin column. Initial elution with methanol was followed by elution with methanolic ammonia (10%). The ammoniacal eluates were concentrated to a gum which was further purified by silica gel chromatography, eluting with DCM/methanolic ammonia (2M, 0-10%). Evaporation of appropriate fractions gave the free base which was dissolved in ethyl acetate (3 ml) and treated with ethereal HCl (1.0M, 5 ml). The resulting suspension was evaporated to dryness by blowing down with a gentle stream of argon to give the title compound (E90) as an off-white solid (0.07 g). $^1$H NMR δ [DMSO-d6/D$_2$O]: 1.29 (6H, d, J=6 Hz), 1.54-1.82 (4H, br. m), 2.87-3.14 (6H, br. m), 3.37-3.55 (4H, m), 3.97 (2H, br. m), 4.28 (1H, br. d, J=13 Hz), 4.54 (1H, br. d, J=10 Hz), 7.14 (2H, d, J=9 Hz), 7.63 (3H, m), 7.96 (2H, d, J=9 Hz), 8.11 (2H, m); LCMS electrospray (+ve) 460 (MH$^+$).

EXAMPLE 91

1-Isopropyl-4-[1-(quinolin-6-yl)-piperidine-4-carbonyl] piperazine hydrochloride (E91)

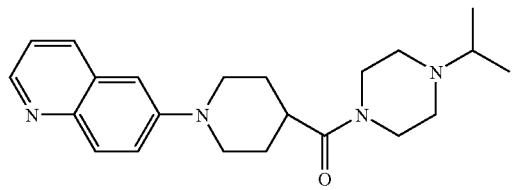

The title compound (E91) was prepared in a similar manner to that described in Example 90, using 6-bromoquinoline. $^1$H NMR δ [DMSO-d6/D$_2$O]: 1.29 (6H, d, J=6 Hz), 1.58-1.85 (4H, br. m), 2.87-3.12 (6H, br. m), 3.37-3.58 (4H, br. m), 4.05 (2H, br. m), 4.30 (1H, br. m), 4.55 (1H, br. m), 7.47 (1H, d, J=3 Hz), 7.85 (IH, dd, J=8, 5 Hz), 7.98 (1H, dd, J=10, 3 Hz), 8.08 (1H, d, J=10 Hz), 8.77 (1H, d, J=8 Hz), 8.85 (1H, dd, J=5, 1Hz); LCMS electrospray (+ve) 367 (MH$^+$).

EXAMPLES 92-95 (E92-E95)

Examples 92-95 were prepared from 1-isopropyl-4-(piperidine-4-carbonyl)-piperazine (D1) and the appropriate aryl bromide, using the procedure described in Example 90. The products displayed $^1$H NMR and mass spectral data that were consistent with structure.

| Example No | Ar | Mass Spectrum (ES+) |
|---|---|---|
| E92 | ![structure] | [MH]+ 387 |
| E93 | ![structure] | [MH]+ 413 |
| E94 | ![structure] | [MH]+ 399 |
| E95 | ![structure] | [MH]+ 370 |

EXAMPLE 96

1-Isopropyl-4-[1-(6-trifluoromethylpyridin-3-yl)-piperldine4-carbonyl]-piperazine hydrochloride (E96)

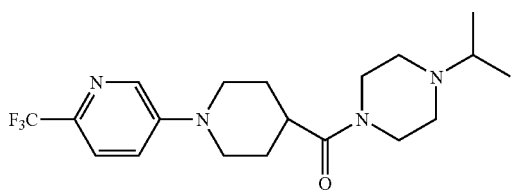

To 5-bromo-2-trifluoromethylpyridine (F. Cottet and M. Schlosser, Eur. J. Org. Chem., 2002, 327-330)(1.4 g) under argon in dry degassed dioxane (10 ml) was added tris(dibenzylideneacetone)palladium(0)(0.24 g) followed by 2-dicyclohexylphosphine-2'-(N,N-dimethylamino)biphenyl (0.49). To this solution, after 30 min, was added 1-isopropyl-4-(piperidine-4-carbonyl)-piperazine (D1)(1.5 g) as a solution in dry degassed dioxane (8 ml) under argon. This was followed by addition of sodium-t-butoxide (1.1 g), and the resulting mixture was heated at reflux for 2 h. After cooling, the reaction was diluted with EtOAc (20 ml) and quenched with saturated NH₄Cl solution. The mixture was poured into a separating funnel and further diluted with EtOAc (30 ml) and washed with excess saturated sodium hydrogen carbonate solution and saturated brine. The EtOAc solution was applied to an SCX resin column. Initial elution with EtOAc and methanol was followed by elution with methanolic ammonia (10%). The ammoniacal eluates were concentrated to a gum which was pre-columned [silica gel, eluting with (15%) methanolic ammonia (2M) in DCM] before being further purified by chromatography [silica gel, gradient elution (0-10%) methanolic ammonia (2M) in DCM]. Evaporation of appropriate fractions gave the free base as a solid (1.2 g) which was dissolved in hot toluene, filtered, and crystallised from the toluene on reduction of volume. Further crystallisations from EtOAc (×3) provided pure crystalline free base (0.6 g). The free base was dissolved in EtOAc/DCM (1:1) and treated with ethereal HCl (1.0M) until the supernatant remained at pH2. The white precipitate was filtered under argon and washed with EtOAc, diethyl ether and petroleum ether before being dried under vacuum. This hydrochloride salt was dissolved in hot EtOH, filtered, and crystallised from the EtOH on reduction of volume. The crystals were filtered and washed with cold EtOH, EtOAc, diethyl ether and petroleum ether before being dried under vacuum to provide the title compound (E96) as a white crystalline solid (0.32 g). ¹H NMR δ [DMSO-d6]: 1.29 (6H, d, J=6 Hz), 1.53-1.79 (4H, br. m), 2.82-3.17 (6H, br. m), 3.39 (2H, br. m), 3.47 (1H, m), 3.64 (1H, br. m), 3.97 (2H, br. m), 4.23 (1H, br. d, J≈14 Hz), 4.49 (1H, br. d, J≈13 Hz), 7.43 (1H, dd, J=9, 3 Hz), 7.62 (1H, d, J=9 Hz), 8.43 (1H, d, J=3 Hz), 11.00 (1H, br.s); LCMS electrospray (+ve) 385 (MH⁺).

EXAMPLE 97

1-Cyclobutyl-4-[1-(6-trifluoromethylpyridin-3-yl)-piperidine-4-carbonyl] piperazine hydrochloride (E97)

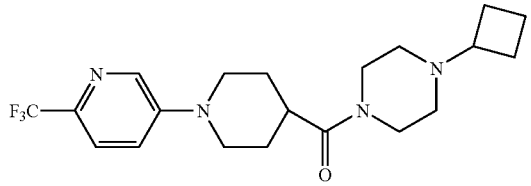

The title compound (E97) was prepared in a similar manner to that described in Example 96, using 5-bromo-2-trifluoromethylpyridine (F. Cottet and M. Schlosser, Eur. J. Org. Chem., 2002, 327-330) and 1-cyclobutyl-4(piperidine-4-carbonyl)-piperazine (free base compound from D7). ¹H NMR δ [DMSO-d6]: 1.53-1.83 (6H, m), 2.15 (2H, m), 2.39 (2H, br. m), 2.70 (1H, m), 2.84 (1H, m), 2.96 (3H, m), 3.07 (IH, m), 3.32 (2H, br. m), 3.52-3.68 (2H, m), ca 4.0 (2H, br., partially obscured by H₂O signal), 4.22 (1H, br. d, J≈14 Hz), 4.46 (1H, br., J≈14 Hz), 7.44 (IH, dd, J=9, 3 Hz), 7.62 (1H, d, J=9 Hz), 8.43 (1H, d, J=3 Hz), 11.54 (1H, br.); LCMS electrospray (+ve) 411 (MH⁺).

EXAMPLE 98

1-Isopropyl-4-[1-(2-cyanopyridin-4-yl)-piperidine-4-carbonyl] piperazine hydrochloride (E98)

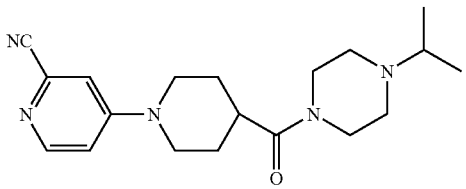

1-Isopropyl-4-(pipeddine-4-carbonyl)-piperazine (D1) (0.116 g), 4-chloro-2-cyanopyridine (T. Sakamoto, S-I.

Kaneda, S. Nishimura and H. Yamanaka, Chem. Pharm. Bull., 1985, 33(2), 565-571)(0.2 g) and anhydrous potassium carbonate (0.347 g) were heated in dry DMSO at 150° C. with stirring, under argon, for 2 h. The cooled mixture was diluted with methanol and applied to an SCX resin column. The column was eluted initially with methanol and then with methanolic ammonia (2M). The ammoniacal eluates were concentrated and the resulting gum was further purified by silica gel chromatography eluting with 0-10% methanolic ammonia (2M) in DCM. The free-base thus obtained was dissolved in DCM (5 ml) and treated with ethereal HCl (1.0M, 5 ml). The resulting suspension was evaporated to dryness by blowing down with a gentle stream of argon, to give the title compound (E98) as an off-white solid (0.117 g). $^1$H NMR δ [DMSO-d6]: 1.29 (6H, d, J=7 Hz), 1.48-1.63 (2H, m), 1.75 (2H, m), 2.89 (1H, br. m), 3.02-3.14 (5H, m), 3.38 (2H, m), 3.47 (1H, m), 3.65 (1H, m), 4.11 (2H, br. m), 4.24 (1H, br. d, J≈14 Hz), 4.48 (1H, br. d, J≈14 Hz), 7.15 (1H, dd, J=7,3 Hz), 7.65(1H, d, J=3 Hz), 8.26 (1H, d, J=7 Hz), 11.10 (1H, br.); LCMS electrospray (+ve) 342 (MH$^+$).

EXAMPLES 99-102 (E99-E102)

Examples 99-102 were prepared from 1-isopropyl4-(piperidinecarbonyl)piperazine (D1) or 1-cyclobutyl-4-(piperidine-4-carbonyl)-piperazine dihydrochloride (D7) as appropriate, and either 4-iodo-2-trifluoromethylpyridine (F. Cottet, M. Marull, O. Lefebvre, and M. Schlosser, Eur. J. Org, Chem., 2003, 1559-1568) or 3-chloro-6-trifluoromethylpyridazine (A. J. Goodman, S. P. Stanforth and B. Tarbit, Tetrahedron, 1999, 55(52), 15067-15070) using the procedure described in Example 90; or alternatively with 4-chloro-2-cyanopyridine (T. Sakamoto, S-I. Kaneda, S. Nishimura and H. Yamanaka, Chem. Pharm. Bull., 1985, 33(2), 565-571) or 2-chloro-5-trifluoromethylpyrazine (D31) using the procedure described in Example 98. The products displayed $^1$H NMR and mass spectral data that were consistent with structure.

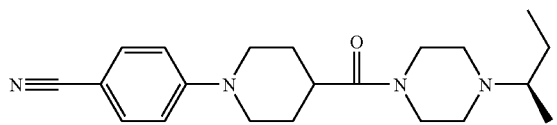

| Example No | Ar | R | Mass Spectrum (ES$^+$) |
|---|---|---|---|
| E99 | NC-pyridyl | cyclobutyl | [MH]$^+$ 354 |
| E100 | F$_3$C-pyridyl | isopropyl | [MH]$^+$ 385 |
| E101 | F$_3$C-pyridazinyl | isopropyl | [MH]$^+$ 400 |

-continued

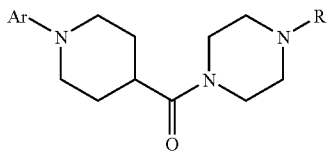

| Example No | Ar | R | Mass Spectrum (ES$^+$) |
|---|---|---|---|
| E102 | F$_3$C-pyrazinyl | isopropyl | [MH]$^+$ 386 |

EXAMPLE 103

(R)-1-Isobutyl-4-[1-(4-cyanophenyl)-piperidine-4-carbonyl]-piperazine hydrochloride (E103)

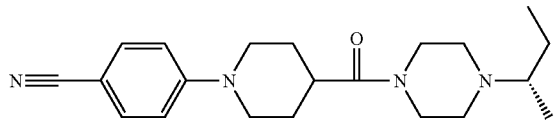

A mixture of (S)-1-methylpropyl methanesulfonate (D32) (305 mg), diisopropylethylamine (0.38 ml) and 1-[1-(4-cyanophenyl)-pipeddine-4-carbonyl]-piperazine (free base compound from D34)(299 mg) in MeCN (3 ml) was heated in a microwave oven at 170° C. for 10 min and evaporated. The residue was partitioned between EtOAc (10 ml) and saturated sodium hydrogen carbonate solution (10 ml). The organic layer was collected washed with water (3×10 ml), brine (10 ml), dried (MgSO$_4$) and evaporated. The residue was flash chromatographed [silica gel, step gradient 1-4% MeOH (containing 10% 0.880 ammonia solution) in DCM]. Fractions containing the required product were evaporated to give the free base compound which was converted to the HCl salt by redissolving in DCM and then treating with excess hydrogen chloride (4M solution in 1,4-dioxan), evaporating and then crystallising from EtOH to give the title compound (E103) as a white solid (72 mg). MS electrospray (+ve) 355 (MH$^+$). $^1$H NMR δ [DMSO-d6]: 11.08 (1H, m), 7.55 (2H, d, J=9 Hz), 7.02 (2H, d, J=9 Hz), 4.47 (1H, m), 4.21 (1H, m), 3.94 (2H, m), 3.69 (1H, m), 3.55-2.83 (1OH, m), 2.97 (1H, m), 1.81-1.33 (4H, m), 1.25 (3H, d, J=6.5 Hz), 0.92 (3H, t, J=7.5 Hz).

EXAMPLE 104

(S)-1-Isobutyl-4-[1-(4-cyanophenyl)-piperidine-4-carbonyl]-piperazine hydrochloride (E104)

A mixture of (R)-1-methylpropyl methanesulfonate (D33) (305 mg), diisopropylethylamine (0.38 ml) and 1-[1-(4-cyanophenyl)-piperidine-4-carbonyl]-piperazine (free base compound from D34)(299 mg) in MeCN (3 ml) was reacted as described in Example 103 to give the title compound (E104) as a white solid (82 mg). MS electrospray (+ve) 355 (MH$^+$).$^1$H NMR δ [DMSO-d6]: 11.08 (1H, m), 7.55 (2H, d, J=9 Hz), 7.02 (2H, d, J=9 Hz), 4.47 (1H, m), 4.21 (IH, m), 3.94 (2H, m), 3.69 (1H, m), 3.55-2.83 (10H, m), 2.97 (1H, m), 1.81-1.33 (4H, m), 1.25 (3H, d, J=6.5 Hz), 0.92 (3H, t, J=7.5 Hz).

EXAMPLE 105

1-Isopropyl-4-[1-(4-cyclopropylcarbonylphenyl)-piperidine-4-carbonyl]-piperazine hydrochloride (E105)

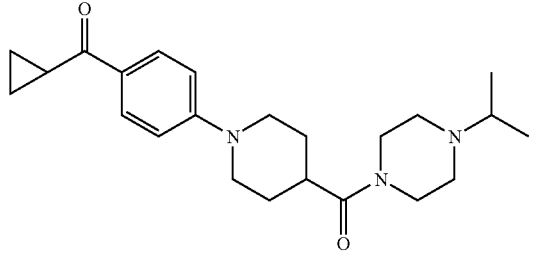

To 1-isopropyl-4-(piperidine-4-carbonyl)-piperazine (D1) (0.25 g) and cyclopropyl-4-fluorophenyl ketone (0.3 g), dissolved in DMSO (5 ml) was added potassium carbonate (0.37 g). The reaction was heated to 140° C. for 2 h. After cooling the mixture, the inorganics were filtered off. The filtrate was diluted with MeOH (20 ml) and then poured onto a 10 g isolute SCX column which was washed with MeOH (50 ml). The product was eluted with 10% ammonia in MeOH (50 ml), and then further purified by column chromatography [silica gel, step gradient 0-10% MeOH (containing 10% 0.88 ammonia solution) in DCM]. Fractions containing the required product were evaporated to give the free base which was dissolved in MeOH (4 ml) and treated with 1N HCl in diethyl ether (2 ml) to give the title compound (E105) as a solid (51mg). $^1$H NMR δ [DMSO-d6]: 0.93 (4H, m) 1.27 (6H, d, J=6.4 Hz), 1.5-1.8 (2H, m), 2.77-3.14 (7H, m), 3.38-3.48 (2H, m), 3.92-4.56 (4H, m), 6.98 (2H, d, J=9.2 Hz), 7.89 (2H, d, J=9.2 Hz), 10.6 (1H, br s). MS electrospray; (+ve ion) 384 (MH$^+$).

EXAMPLE 106-115 (E106-115)

Examples 106-115 were prepared from 1-isopropyl-4-(piperidine-4-carbonyl)-piperazine (D1) and the appropriate substituted aryl fluoride using the procedure described in Example 105 and displayed $^1$H NMR and mass spectral data that were consistent with structure.

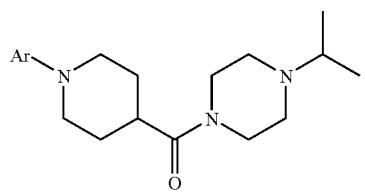

| Example No | Ar | Mass Spectrum (ES$^+$) |
|---|---|---|
| E106 | 2,5-difluoro-4-methyl-benzonitrile | [MH]$^+$ 377 |
| E107 | 2,6-difluoro-4-methyl-benzonitrile | [MH]$^+$ 377 |
| E108 | 2-chloro-4-methyl-benzonitrile | [MH]$^+$ 375 |
| E109 | 2-methoxy-4-methyl-benzonitrile | [MH]$^+$ 371 |
| E110 | 2-fluoro-1-(4-methylphenyl)ethanone | [MH]$^+$ 376 |
| E111 | 1-(2,5-difluoro-4-methylphenyl)ethanone | [MH]$^+$ 394 |
| E112 | 1-(4-methylphenyl)propan-1-one | [MH]$^+$ 372 |
| E113 | cyclobutyl-(4-methylphenyl)methanone | [MH]$^+$ 398 |
| E114 | phenyl-(4-methylphenyl)methanone | [MH]$^+$ 420 |
| E115 | 1-(4-methylphenyl)ethanone | [MH]$^+$ 358 |

EXAMPLE 116

1-Propyl-4-[1-(4-cyanophenyl)-piperidine-4-carbonyl]-piperazine hydrochloride (E116)

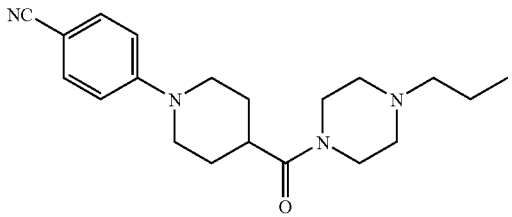

A solution of 1-[1-(4-cyanophenyl)-piperidine-4-carbonyl]-piperazine hydrochloride (D34) (0.3 g) in dry DCM (10 ml) was treated with triethylamine (0.25 ml) and propionaldehyde (0.25 ml). The reaction mixture was stirred at rt for 30 min. Sodium triacetoxyborohydride (3.7 g) was added and the reaction was stirred at rt overnight. The reaction mixture was treated with 1N NaOH (2 ml) and stirred at rt for 15 min followed by the addition of water (20 ml) and DCM (20 ml). The organic layer was dried ($MgSO_4$) and filtered and the filtrate was absorbed onto silica gel (5 g) and purified by column chromatography (silica gel, step gradient 0-10% MeOH (containing 10% 0.88 ammonia solution) in DCM]. The fractions containing the required product were evaporated and the free base was dissolved in MeOH (1 ml) and treated with ethereal HCl to give the title compound (E116) as a solid (50 mg). MS electrospray; (+ve ion) 341 ($MH^+$).

EXAMPLE 117

1-Isopropyl-4-[1-(2-methyl-4-quinolinyl)-piperidine carbonyl]-piperazine hydrochloride (E117)

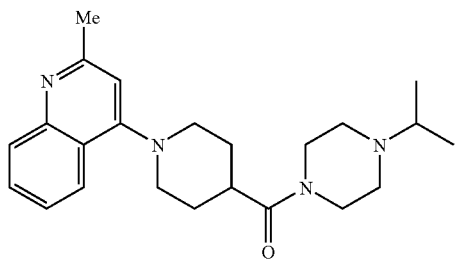

4-Chloro-2-methyl-quinoline (0.16 g) in degassed dry dioxan (3 ml) was charged with tris(dibenzylideneacetone)dipalladium(0)(30 mg) and 2-dicyclohexylphosphino-2'-(N,N-dimethylamino)biphenyl (60 mg). The dark suspension was stirred at rt for 20 min under a blanket of Argon. To this reaction a solution of 1-isopropyl-4-(piperidine-4-carbonyl)piperazine (D1)(0.2 g) in degassed dioxan (2 ml) was added followed by potassium phosphate (0.35 g). The reaction mixture was stirred at 80° C. for 2 h. After allowing the reaction to cool to rt MeOH (20 ml) was added and the crude reaction mixture was poured onto a 10 g isolute SCX column which was washed with MeOH (50 ml). The product was eluted with 10% ammonia in MeOH (50 ml) and further purified by column chromatography [silica gel, step gradient 0-10% MeOH (containing 10% 0.88 ammonia solution) in DCM]. Fractions containing the required product were evaporated to give the free base which was dissolved in DCM (10 ml) and treated with 1N HCl in diethyl ether to give the title compound (E117) as a solid (150 mg). $^1$H NMR δ [MeOH-d4]: 1.42 (6H, d, J=6.8 Hz), 1.98-2.03 (4H, m), 2.79 (3H, s), 3.08-3.29 (4H, m), 3.55-3.65 (6H, m), 4.22-4.25 (2H, m), 4.7-4.85 (1H, m), 7.08 (1H, m), 7.69 (1H, m) 7.69 (1H, t, J=8.4 Hz), 7.85 (1H, d), 7.92 (1H, t, J=8.4 Hz), 8.14 (1H, d, J=8.4 Hz). MS electrospray (+ve ion) 381 (MH+).

EXAMPLE 118

1-Isopropyl4-[1-(2-methyl-quinolin-6-yl)-piperidine-4-carbonyl]-piperazine hydrochloride (E118)

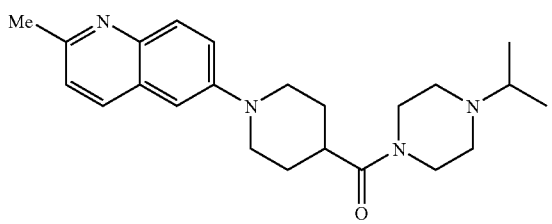

6-Bromo-2-methyl-quinoline (0.25 g) in degassed dry dioxan (3 ml) was charged with tris(dibenzylideneacetone)dipalladium(0)(40 mg) and 2-dicyclohexylphosphino-2'-(N,N-dimethylamino)biphenyl (70 mg). The dark suspension was stirred at rt for 1 h under a blanket of Argon. To this reaction a solution of 1-isopropyl-4-(piperidine4-carbonyl)piperazine (D1)(0.269 g) in degassed dioxan (2 ml) was added followed by sodium tert-butoxide (0.35 g). The reaction mixture was stirred at 100° C. for 2 h. After allowing the reaction to cool to rt MeOH (20 ml) was added and the crude mixture was poured onto a 10 g isolute SCX column which was washed with MeOH (50 ml). The product was eluted with 10% ammonia in MeOH (50 ml), and then further purified by column chromatography [silica gel, step gradient 0-10% MeOH (containing 10% 0.88 ammonia solution) in DCM]. Fractions containing the required product were evaporated to give the free base which was dissolved in DCM (10 ml) and treated with 1N HCl in diethyl ether to give a solid which was recrystallised from $CH_3CN$ to give the title compound (E118) (100 mg). $^1$H NMR δ [DMSO-d6]: 1.28 (6H, d, J=6.8 Hz), 1.69-1.80 (4H, m), 2.89 (3H, s), 2.98-3.18 (4H, m), 3.38-3.70 (5H, m), 3.9-4.50, (5H, m), 7.48 (1H, d, J=2.4 Hz), 7.77 (1H, d, J=8.8 Hz), 7.95 (1H, d, J=9.6 Hz), 8.1 (1H, d, J=9.6 Hz), 8.7 (1H, d, J=8.8 Hz), 10.98 (1H, br s). MS electrospray (+ve ion) 381 (MH+).

EXAMPLE 119

1-Isopropyl-4-[1-(isoquinolin-5-yl)-piperidine-4-carbonyl]-piperazine hydrochloride (E119)

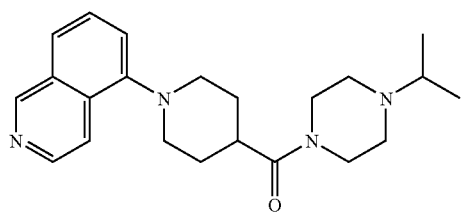

The title compound (E119) was prepared in a similar manner to Example 118 from 5-bromoisoquinoline, and displayed $^1$H NMR and mass spectral data that were consistent with structure. MS electrospray (+ve ion) 367 (MH+).

EXAMPLE 120-125

Examples 120-125 were prepared from the appropriate 4-bromo aryl precursors using the procedure of Example 118 and displayed $^1$H NMR and mass spectral data that were consistent with structure. The aryl bromide precursors for Examples 123-125 were prepared as described in Descriptions 37, 39 and 40 respectively.

| Example No | Ar | Mass Spectrum (ES+) |
|---|---|---|
| E120 | | [MH]+ 399 |
| E121 | | [MH]+ 381 |
| E122 | | [MH]+ 383 |
| E123 | | [MH]+ 397 |
| E124 | | [MH]+ 397 |
| E125 | | [MH]+ 398 |

EXAMPLE 126

1-Isopropyl-4-[1-(4-cyanomethylcarbonyl-phenyl)-piperidine-4-carbonyl]-piperazine hydrochloride (E126)

The title compound (E126) was prepared using the conditions described for Example 118 from 5-(4-bromophenyl)-isoxazole. MS electrospray (+ve ion) 383 (MH+). $^1$H NMR data consistent with ring opened product derived from the isoxazole.

EXAMPLES 127 and 128

Examples 127 and 128 were prepared by reacting 2-chloro-5-trifluoromethyl-pyridine and 2-chloro-3-cyano-pyrazine, respectively with 1-isopropyl-4-(piperidine-4-carbonyl)-piperazine (D1) following the procedure for Example 105. Final products displayed $^1$H NMR and mass spectral data that were consistent with structure.

| Example No | Ar | Mass Spectrum (ES+) |
|---|---|---|
| E127 | | [MH]+ 385 |
| E128 | | [MH]+ 343 |

EXAMPLE 129

1-Isopropyl-4-[1-(6-cyano-pyridin-3-yl)-piperidine-4-carbonyl]-piperazine hydrochloride (E129)

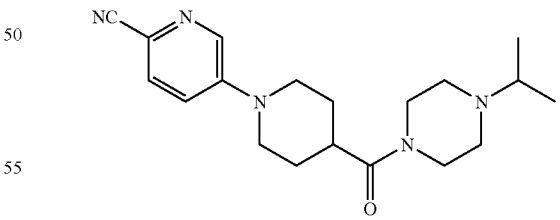

1-Isopropyl-4-(pipenidine-4-carbonyl)-piperazine dihydrochloride (product of D1, step 1) (0.30 g), 5-bromo-pyridine-2-carbonitrile (0.23 g) and potassium carbonate (0.3 g) were stirred in DMSO (1.5 ml) at 160° C. for 1.5 h. The reaction was worked up as described for Example 78 to give the title compound (E129) as a solid (89 mg). LCMS electrospray (+ve) 342 (MH+). $^1$H NMR δ [MeOH-d4]: 1.41 (6H, d, J=12.8 Hz), 1.7-1.97 (4H, m), 3.0-3.16 (6H, m), 3.56-3.75

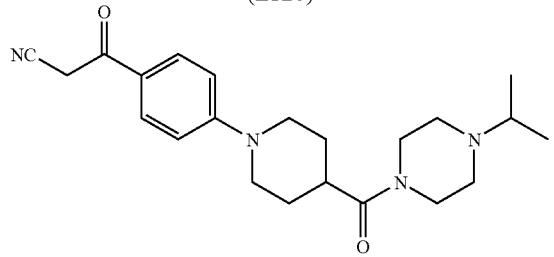

(4H, m), 4.0-4.1 (2H, m), 4.35-4.45 (1H, m), 4.7-4.8 (1H, m), 7.48 (1H, d, J=8.8 Hz), 7.71 (1H, d, J=8.8 Hz), 8.4 (1H, d, J=2.8 Hz).

EXAMPLE 130 and 131

Examples 130 and 131 were prepared by reacting 5-bromo-2-methyl-pyridine and 4-chloro-2-methyl-pyridine, respectively with 1-isopropyl-4-(piperidine-4carbonyl)-piperazine (D1) and following the method described for Example 118. Final products displayed ¹H NMR and mass spectral data that were consistent with structure.

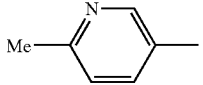

| Example No | Ar | Mass Spectrum (ES⁺) |
|---|---|---|
| E130 | 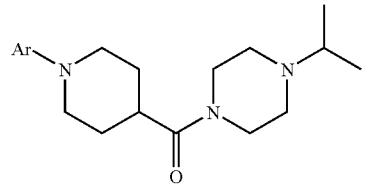 | [MH]⁺ 331 |
| E131 | | [MH]⁺ 331 |

EXAMPLES 132 and 133

Examples 132 and 133 were prepared from 2-chloro-5-(1-pyrrolidinylcarbonyl)pyridine (D35) and 2-chloro-5-(dimethylaminocarbonyl)pyridine (D36) respectively using the procedure described for Example 105, and displayed ¹H NMR and mass spectral data that were consistent with structure.

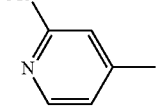

| Example No | Ar | Mass Spectrum (ES⁺) |
|---|---|---|
| E132 | 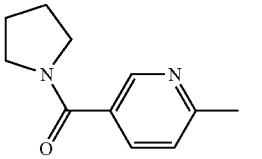 | [MH]⁺ 414 |
| E133 | 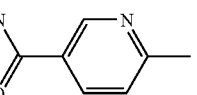 | [MH]⁺ 388 |

EXAMPLE 134

1-Isopropyl-4-{1-[4-(isoxazol-5-yl)phenyl]-piperidine-4-carbonyl}-piperazine hydrochloride (E134)

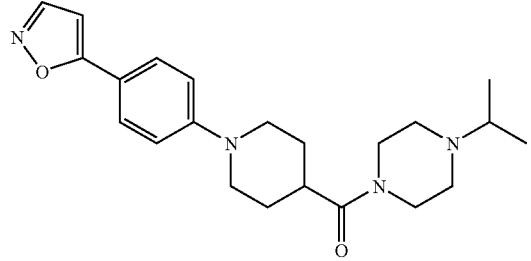

The title compound (E134) was prepared using the conditions described for Example 117 from 5-(4-bromophenyl)-isoxazole. MS electrospray (+ve ion) 383 (MH+). ¹H NMR data consistent with structure.

EXAMPLE 135

1-Isopropyl-4-[1-(6-trifluoromethylpyridin-3-yl)-piperidine-4-carbonyl]-[1,4]-diazepane hydrochloride (E135)

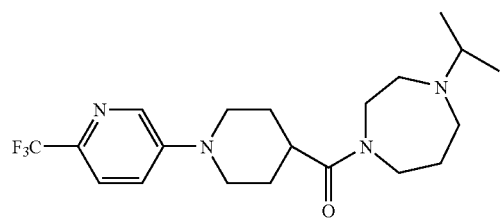

To 5-bromo-2-trifluoromethylpyridine (1.4 g)(F. Cottet and M. Schlosser, Eur. J. Org. Chem., 2002, 327-330), dissolved in dry degassed dioxane (15 ml) under argon, was added tris(dibenzylideneacetone)dipalladium(0)(0.24 g) and 2-dicyclohexylphosphino-2'-(N,N-dimethylamino)biphenyl (0.49 g). The mixture was stirred at rt for 1 h before being added to 1-isopropyl-4-(piperidine-4-carbonyl)-[1,4]-diazepane (1.5 g)(D8) dissolved in dry degassed dioxane (10 ml) under argon. Sodium tert-butoxide (1.1 g) was added to the reaction which was then heated in an oil bath at 120° C. for 2 h under argon. At this point the reaction was cooled, diluted with EtOAc (10 ml) and pipetted onto an isolute SCX (20 g) column. This column was washed with EtOAc (60 ml) followed by MeOH (150 ml). The reaction product was then eluted from the column using 10% ammonia in MeOH. The fractions containing the product were combined, evaporated from toluene and further purified by column chromatography [silica gel, step gradient 0-10% MeOH (containing 10% 0.88 ammonia solution) in DCM]. The fractions containing the product were combined, evaporated and re-evaporated from toluene to give the free base as a solid (1.2 g). The free base was triturated with diethyl ether, then dried under vacuum and dissolved in EtOAc. This solution was filtered through a glass fibre filter paper and the free base crystallised after heating, reducing volume and cooling. Two further re-crystallisations from EtOAc provided pure free base (0.7 g). The free base was taken up into EtOAc and HCl in diethyl ether (1M) was added. The precipitated hydrochloride salt was filtered under argon and washed with diethyl ether and pentane before being dried under vacuum. The white solid was dissolved in EtOH, filtered through a glass fibre filter paper, and crystallised from hot EtOH, on reducing volume, to give the title compound (E135) as white crystals (0.42 g). $^1$H NMR δ [DMSO-d6]: 1.27 (6H, m), 1.57-1.87 (4H, m), 1.97-2.14 (1H, m), 2.24 and 2.43 (2×m, total of 1H), 2.85-3.22 (5H, m), 3.39-3.76 (6H, m), 3.90-4.08 (3H, m), 7.43 (1H, dd, J=9, 3 Hz), 7.62 (1H, d, J=9 Hz), 8.42 (1H, d, J=3 Hz), 10.63 and 10.74 (2×brs. in -2:1 ratio, total of 1H); LCMS electrospray (+ve) 399 (MH$^+$) and 421 (MNa$^+$).

EXAMPLE 136

1-Cyclobutyl-4-[1-(6-trifluoromethylpyridin-3-yl)-piperidine-4-carbonyl]-[1,4]-diazepane hydrochloride (E136)

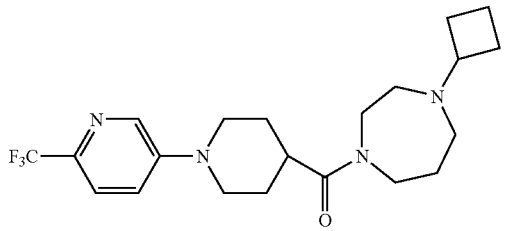

The title compound (E136) was prepared in a similar manner to that described in Example 135, using 1-cyclobutyl-4-(piperidine-4-carbonyl)-[1,4]-diazepane (D10) and 5-bromo-2-trifluoromethylpyridine. $^1$H NMR δ [DMSO-d6]: 1.58-1.83 (6H, m), 2.01-2.24 and 2.33-2.46 (2×m, total of 6H), 2.75 (1H, m), 2.82-3.00 (4H, m), 3.28-3.57 and 3.57-3.83 (2×m, total of 6H), 3.96-4.05 (3H, m), 7.44 (1H, dd, J=9, 3 Hz), 7.62 (1H, d, J=9 Hz), 8.43 (1H, d, J=3 Hz), 11.14 and 11.27 (2×br. m, in I2:1 ratio, total of 1H); LCMS electrospray (+ve) 411 (MH$^+$).

EXAMPLE 137

1-Cyclobutyl-4-[1-(2-cyanopyridin-4-yl)-piperidine-4-carbonyl]-[1,4]-diazepane hydrochloride (E137)

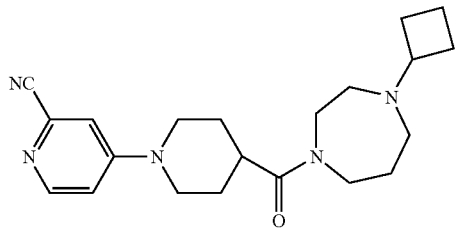

The title compound (E137) was prepared in a similar manner to that described in Example 98, using 1-cyclobutyl-4-(piperidine-4-carbonyl)-[1,4]-diazepane (D10) and 4-chloro-2-cyanopyridine (T. Sakamoto, S-I. Kaneda, S. Nishimura and H. Yamanaka, Chem. Pharm. Bull., 1985, 33(2), 565-571). $^1$H NMR δ [DMSO-d6]: 1.51-1.83 (6H, m), 2.01-2.23 (3H, m), 2.37-2.49 (3H, m), 2.72-3.15 (5H, m), 3.30-3.85 (6H, m), 4.01-4.10 (3H, m), 7.14 (1H, dd, J=7, 3 Hz), 7.64 (1H, d, J=3 Hz), 8.26 (1H, d, J=7 Hz), 11.19 and 11.34 (2×br. m, in ~2:1 ratio, total of 1H); LCMS electrospray (+ve) 368 (MH$^+$).

EXAMPLE 138

1-Isopropyl-4-[1-(6-trifluoromethylpyridazin-3-yl)-piperidine-4-carbonyl]-[1,4]-diazepane hydrochloride (E138)

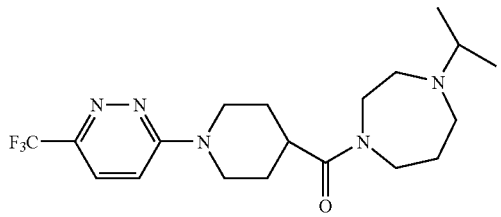

The title compound (E138) was prepared in a similar manner to that described in Example 90 using 1-isopropyl-4(piperidine-4-carbonyl)-[1,4]-diazepane (D8) and 3-chloro-6-trifluoromethylpyridazine (A. J. Goodman, S. P. Stanforth and B. Tarbit, Tetrahedron, 1999, 55(52), 15067-15070). $^1$H NMR δ [DMSO-d6]: 1.27 (6H, m), 1.57 (2H, m), 1.82 (2H, m), 1.97-2.25 and 2.34-2.44 (2×m, total of 2H), 2.94-3.23 (5H, m), 3.34-3.97 (6H, m), 4.03 (1H, m), 4.51 (2H, br. t, J≈13 Hz), 7.44 (1H, d, J=10 Hz), 7.78 (1H, d, J=10 Hz), 10.45 and 10.56 (2×br. m, in ~2:1 ratio, total of 1H); LCMS electrospray (+ve) 400 (MH$^+$).

EXAMPLE 139

1-Isopropyl-4-[1-(5-trifluoromethylpyrazin-2-yl)-piperidine-4-carbonyl]-[1,4]-diazepane hydrochloride (E139)

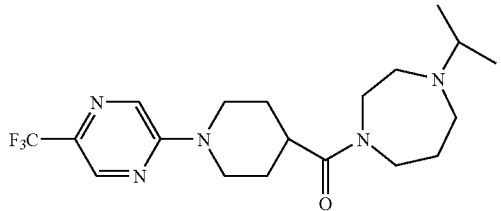

The title compound (E139) was prepared in a similar manner to that described in Example 98, using 1-isopropyl-4(piperidine-4-carbonyl)-[1,4]-diazepane (D8) and 2-chloro-5-trifluoromethylpyrazine (D31). ¹H NMR δ [DMSO-d6]: 1.27 (6H, m), 1.55 (2H, m), 1.81 (2H, m), 1.99-2.22 and 2.31-2.41 (2×m, total of 2H), 2.92-3.23 (5H, m), 3.34-3.92 (6H, m), 4.00 (1H, m), 4.49 (1H, br. d, J≈13 Hz), 8.45 (1H, s), 8.47 (1H, s), 10.36 and 10.48 (2×br. m, in ~2:1 ratio, total of 1H); LCMS electrospray (+ve) 400 (MH⁺).

EXAMPLES 140 and 141 (E140-141)

Examples 140 and 141 were prepared from 1-isopropyl4-(piperidine-4-carbonyl)-[1,4]-diazepane (D8) and either 4-iodo-2-trifluoromethylpyridine (F. Cottet, M. Marull, O. Lefebvre, and M. Schlosser, Eur. J. Org. Chem., 2003, 1559-1568) using the procedure described in Example 90; or, 4-chloro-2-cyanopyridine (T. Sakamoto, S-I. Kaneda, S. Nishimura and H. Yamanaka, Chem. Pharm. Bull., 1985, 33(2), 565-571) using the procedure described in Example 98. The products displayed ¹H NMR and mass spectral data that were consistent with structure.

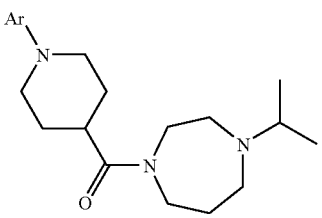

| Example No. | Ar | Mass Spectrum (ES⁺) |
|---|---|---|
| E140 | NC-pyridyl-4-methyl | [MH]⁺ 356 |
| E141 | F₃C-pyridyl-4-methyl | [MH]⁺ 399 |

EXAMPLES 142-149 (E142-149)

Examples 142-149 were prepared from either 1-isopropyl-4-(piperidine-4-carbonyl)-[1,4]-diazepane (D8) or 1-cyclobutyl-4(pipeddine-4-carbonyl)-[1,4]-diazepane (D10) and the appropriate aryl fluoride. The reactants were heated 140° C. in DMSO for 3 h in the presence of potassium carbonate following the procedure of Example 1.

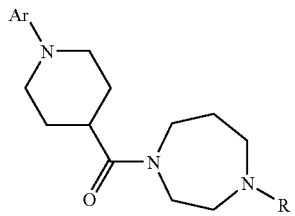

| Example No | Ar | R | Mass Spectrum (ES⁺) |
|---|---|---|---|
| E142 | 2-Br, 4-CN-phenyl | iPr | [MH]⁺ 433/435 |
| E143 | 3-Br, 4-CN-phenyl | iPr | [MH]⁺ 433/435 |
| E144 | 3-CF₃, 4-CN-phenyl | iPr | [MH]⁺ 423 |
| E145 | 3-F, 4-CN-phenyl | cyclobutyl | [MH]⁺ 385 |
| E146 | 2,3-diF, 4-CN-phenyl | cyclobutyl | [MH]⁺ 403 |
| E147 | 3-Br, 4-CN-pyridyl | cyclobutyl | [MH]⁺ 445/447 |
| E148 | 2-Br, 4-CN-phenyl | cyclobutyl | [MH]⁺ 445/447 |
| E149 | CN-naphthyl | cyclobutyl | [MH]⁺ 417 |

EXAMPLE 150

1-Isopropyl-4-[1-(4-acetylphenyl)-piperidine-4-carbonyl]-[1,4]-diazepane hydrochloride (E150)

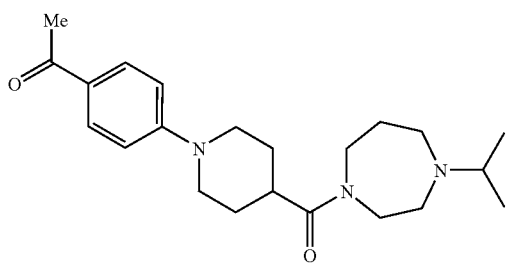

1-Isopropyl-4-(piperidine-4-carbonyl)-[1,4]-diazepane (D8)(0.15 g), 4-fluoroacetophenone (0.16 g) and potassium carbonate (0.24 g) were stirred in DMSO (2 ml) and heated to 150° C. for 2 h. After cooling the mixture, the inorganic solids were removed by filtration. The filtrate was diluted with MeOH (20 ml) and poured onto a 10 g isolute SCX column which was washed with MeOH (50 ml). The product was eluted with 10% ammonia in MeOH (50 ml), and then further purified by column chromatography [silica gel, step gradient 0-10% MeOH (containing 10% 0.88 ammonia solution) in DCM]. Fractions containing the required product were evaporated to give the free base which was dissolved in MeOH (4 ml) and treated with excess hydrogen chloride (1N HCl in diethyl ether)(2 ml) to give the title compound (E150) as a solid (16 mg) after crystallisation from acetonitrile. $^1$H NMR δ [DMSO-d6]: 1.24-1.28 (6H, m), 1.59-1.74 (4H, m), 2.07-2.32 (2H, m), 2.47 (3H, s), 2.88-3.25, (5H, m), 3.40-3.87 (5H, m), 3.994.01 (3H, m), 6.98 (2H, d, J=9.2 Hz), 7.82 (2H, d, J=9.2 Hz), 9.2 (1H, br s). MS electrospray; (+ve ion) 372 (MH+).

EXAMPLE 151

1-Isopropyl-4-[1-(4-propanoylphenyl)-piperidine-4-carbonyl]-[1,4]-diazepane hydrochloride (E151)

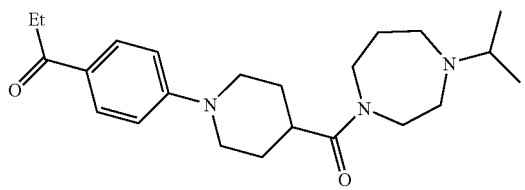

The title compound (E151) was prepared from 4-fluoropropiophenone using the procedure described in Example 150. $^1$H NMR δ [DMSO-d6]: 0.94-0.95 (6H, m), 1.55-1.8 (7H, m), 2.63-2.68 (1H, m), 2.8-3.0 (7H, m), 3.39-3.60 (4H, m), 3.9-3.98 (2H, m), 6.9 (2H, d, J=8 Hz), 7.79 (2H, d, J=8 Hz). MS electrospray; (+ve ion) 386 (MH+).

EXAMPLE 152-153

Examples E152 and 153 were prepared from 1-isopropyl-4(piperidine-4-carbonyl)-[1,4]-diazepane (D8) with cyclopropyl 4-fluorophenylketone, and cyclobutyl 4-fluorophenylketone respectively. Products displayed $^1$H NMR and mass spectral data that were consistent with structure.

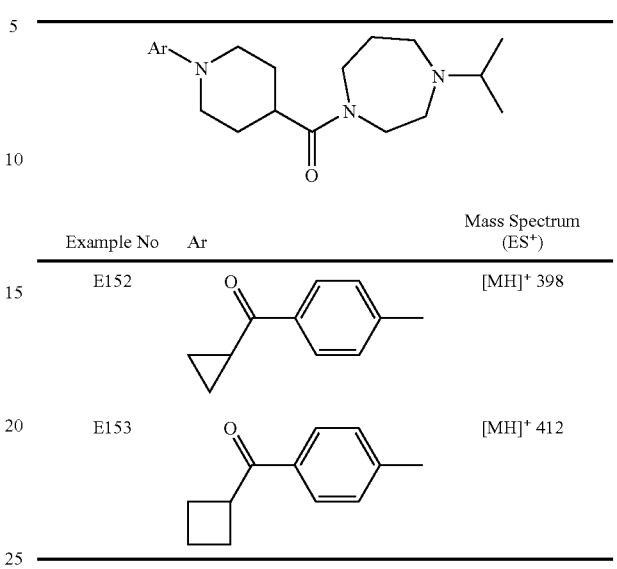

| Example No | Ar | Mass Spectrum (ES+) |
|---|---|---|
| E152 | | [MH]+ 398 |
| E153 | | [MH]+ 412 |

EXAMPLE 154

1-Isopropyl-4-{1-[4-(2-methyl-1,3-oxazol-5-yl)phenyl]-piperidine-4-carbonyl}-[1,4]-diazepane hydrochloride (E154)

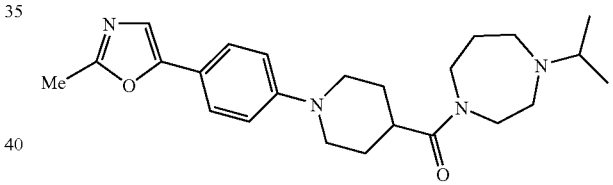

1-Isopropyl-4-(piperidine-4-carbonyl)-[1,4]diazepane (0.12 g)(D8) was dissolved in dry degassed toluene (1 ml) and to this solution 5-(4-bromophenyl)-2-methyl-oxazole (D38) (0.1 g) in toluene (1 ml) and acetato(2'-di-t-butylphosphin-1, 1'-biphenyl-2-yl)palladium II (20 mg) and sodium t-butoxide (100 mg) were added. The reaction mixture was stirred at 60° C. under argon overnight. The cooled mixture was diluted with MeOH (20 ml) and then poured onto a 10 g isolute SCX column which was washed with MeOH (50 ml). The product was eluted with 10% ammonia in MeOH (50 ml), and further purified by column chromatography [silica gel, step gradient 0-10% MeOH (containing 10% 0.88 ammonia solution) in DCM]. Fractions containing the required product were evaporated to give the free base. Conversion into the HCl salt in MeOH (1 ml) with 1N ethereal HCl (1 ml) afforded the title compound (E154) as a solid (155 mg). $^1$H NMR δ [MeOH-d4]: 1.3-1.43 (6H, m), 2.25-2.32 (6H, m), 3.554.1 (13H, m), 7.64 (1H, s), 7.78 (2H, d, J=8.4kz), 7.93 (2H, d, J=8.4 Hz). MS electrospray;(+ve ion) 411 (MH+).

EXAMPLES 155-167 (E155-E167)

Examples 155 and 156 were prepared by reacting 1-isopropyl-4-(piperidine-4-carbonyl)-[1,4]-diazepane (D8) and the appropriate aryl bromide following the method of Example 154. Examples 157-167 were prepared from the appropriate aryl bromides following the reaction conditions described for Example 118. Products displayed ¹H NMR and mass spectral data which were consistent with structure.

| Example No | Ar | Mass Spectrum (ES⁺) |
|---|---|---|
| E155 | oxazol-5-yl-phenyl | [MH]⁺ 397 |
| E156 | 2-methyl-oxazol-4-yl-phenyl | [MH]⁺ 411 |
| E157 | 2-methyl-thiazol-4-yl-phenyl | [MH]⁺ 427 |
| E158 | isoxazol-5-yl-phenyl | [MH]⁺ 397 |
| E159 | 3-methyl-isoxazol-5-yl-phenyl | [MH]⁺ 411 |
| E160 | 5-methyl-1,2,4-oxadiazol-3-yl-phenyl | [MH]⁺ 412 |
| E161 | 5-phenyl-1,3,4-oxadiazol-2-yl-phenyl | [MH]⁺ 474 |
| E162 | 4-methyl-benzoxazine | [MH]⁺ 401 |
| E163 | quinolin-6-yl | [MH]⁺ 381 |
| E164 | isoquinolin-6-yl | [MH]⁺ 381 |

-continued

| Example No | Ar | Mass Spectrum (ES⁺) |
|---|---|---|
| E165 | pyrrol-1-yl-phenyl | [MH]⁺ 394 |
| E166 | 2-oxo-pyrrolidin-1-yl-phenyl | [MH]⁺ 413 |
| E167 | isoquinolin-5-yl | [MH]⁺ 381 |

EXAMPLE 168

1-Isopropyl-4-(1-[4-(3-methyl-1,2,4-oxadiazol-5-yl) phenyl]-piperidine-4-carbonyl]-[1,4]-diazepane hydrochloride (E168)

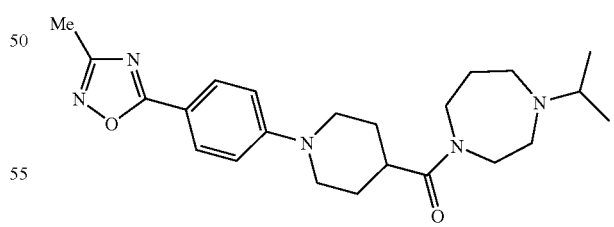

The title compound (E168) was prepared from 1-isopropyl-4-(piperidine-4-carbonyl)-[1,4]iazepane (D8)(0.2 g) and 5-(4-bromophenyl)-3-methyl-1,2,4-oxadiazole (D41) (0.2 g) using the procedure described for Example 117. ¹H NMR δ[MeOH-d4]: 1.37-1.41 (6H, m), 1.98-2.0 (3H, s), 2.2-2.41 (2H, m), 3.04-3.29 (2H, m), 3.63-4.1 (10H, m), 7.36 (2H, d, J=8.4 Hz), 8.0 (2H, J=8.4 Hz). MS electrospray (+ve ion) 412 (MH+).

EXAMPLE 169

1-Isopropyl-4-[1-(4-acetamido-3-fluorophenyl)-piperidine-4-carbonyl]-[1,4]-diazepane hydrochloride (E169)

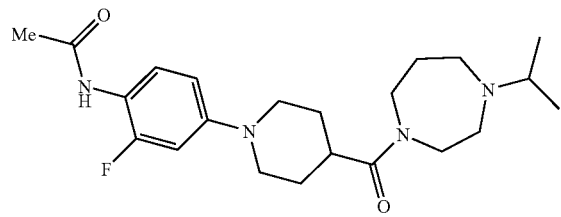

The title compound (E169) was prepared from 1-isopropyl-4-(piperidine-4-carbonyl)-[1,4]-diazepane (D8) and N-(4-bromo-2-fluorophenyl)-acetamide following the procedure of Example E117 using potassium phosphate as the base. $^1$H NMR δ [MeOH-d4]: 1.39-1.41 (6H, m), 2.25-2.34 (8H, m), 3.14-3.25 (2H, m), 3.55-3.9 (9H, m), 4.07-4.08 (1H, m), 7.35, (1H, d, J=8 Hz), 7.48 (1H, d, J=8 Hz), 8.1 (1H, m). MS electrospray (+ve ion) 405 (MH+).

EXAMPLE 170

1-Cyclobutyl-4-[1-(4-acetylphenyl)-piperidine-4-carbonyl]-[1,4]-diazepane hydrochloride (E170)

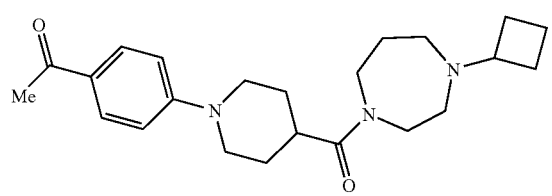

The title compound (E170) was prepared as for Example 150 from 1-cyclobutyl-4-(piperidine-4-carbonyl)-[1,4]-diazepane (D10) and 4-fluoroacetophenone. $^1$H NMR δ [MeOH-d4]: 1.5 (3H, s), 1.78-2.0 (4H, m), 2.2-2.37 (12H, m), 2.90-3.18 (3H, m), 3.47-3.64 (3H, m), 3.75-4.2 (4H, m), 7.72-7.74 (4H, dd, J=6.8 Hz). MS electrospray (+ve ion) 384 (MH+).

EXAMPLES 171-173 (E171-E173)

Examples 171-173 were prepared from 1-cyclobutyl-4-(piperidinecarbonyl)-[1,4]-diazepane (D10) and the appropriate fluorophenyl ketones according to the procedure described in Example 150. Products displayed $^1$H NMR and mass spectral data that were consistent with structure.

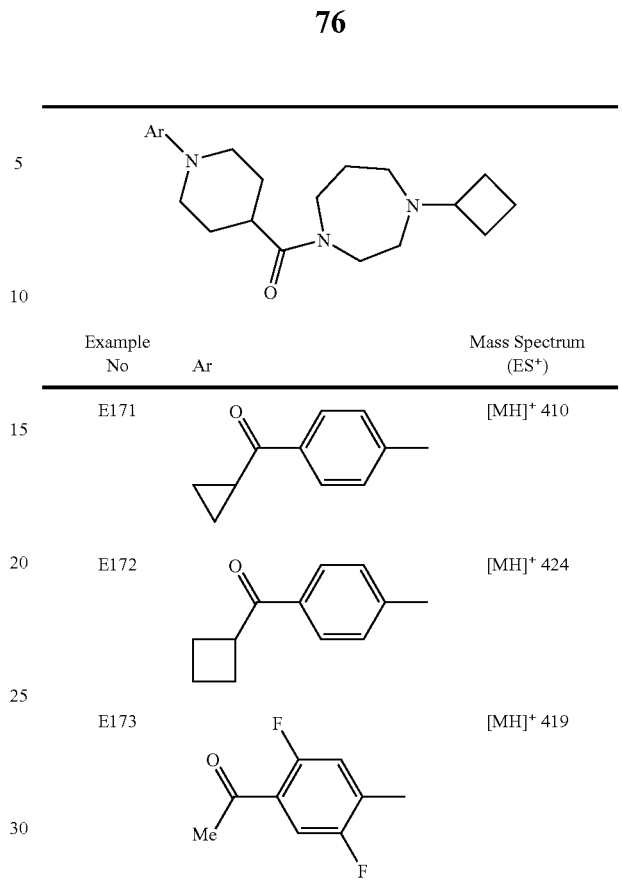

| Example No | Ar | Mass Spectrum (ES+) |
|---|---|---|
| E171 | (4-methylphenyl cyclopropyl ketone) | [MH]+ 410 |
| E172 | (4-methylphenyl cyclobutyl ketone) | [MH]+ 424 |
| E173 | (2,5-difluoro-4-methylphenyl methyl ketone) | [MH]+ 419 |

EXAMPLE 174

1-Isopropyl-4-[1-(5-cyanopyridin-2-yl)-piperidine-4-carbonyl]-[1,4]-diazepane hydrochloride (E174)

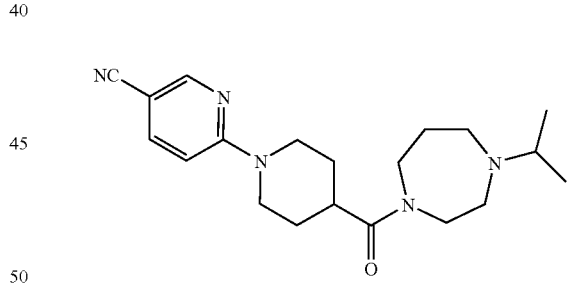

The title compound (E174) was prepared from 1-[1-(5-cyanopyridin-2-yl)-pipeddine-4-carbonyl]-[1,4]-diazepane hydrochloride (D14), acetone and sodium triacetoxyborohydride following the procedure described for Example 37 and displayed $^1$H NMR and mass spectral data that were consistent with structure. MS electrospray (+ve ion) 356 (MH+).

EXAMPLES 175-178 (E175-E178)

Examples 175-178 were prepared from 1-isopropyl-4-(pipeddine-4-carbonyl)-[1,4]-diazepane (D8), and the appropriate 2-chloropyridine intermediate following the procedure described in Example 150. Products displayed $^1$H NMR and mass spectral data consistent with the structure.

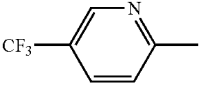

| Example No | Ar | Mass Spectrum (ES+) |
|---|---|---|
| E175 | 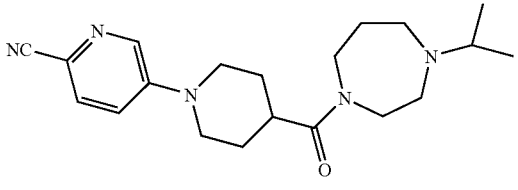 | [MH]+ 399 |
| E176 | 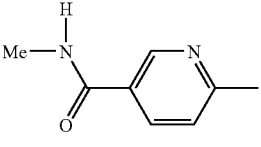 | [MH]+ 380 |
| E177 | 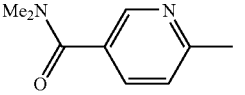 | [MH]+ 402 |
| E178 | 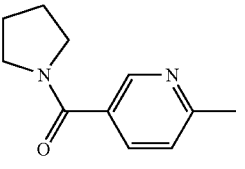 | [MH]+ 428 |

EXAMPLE 179

1-Cyclobutyl-4-[1-(6-cyano-pyridin-3-yl)-piperidine-4-carbonyl]-[1,4]-diazepane hydrochloride (E179)

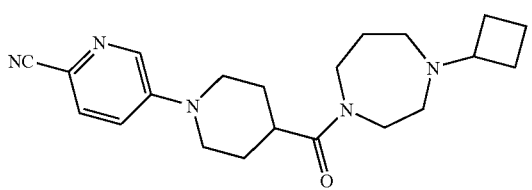

Example 179 was prepared from 1-cyclobutyl-4-(piperidine-4-carbonyl)-[1,4]-diazepane (D10) and 5-bromo-2-cyanopyridine using the method described for Example 150. ¹H NMR δ [MeOH-d4]: 1.78-1.90 (6H, m), 2.29-2.36 (6H, m), 2.92-3.18 (5H, m), 3.49-3.87 (6H, m), 4.03-4.18 (3H, m), 7.44 (1H, dd, J=8.8 Hz), 7.68 (1H, d, J=8.8 Hz), 8.37 (1H, d, J=3.2 Hz). MS electrospray (+ve ion) 368 (MH+).

EXAMPLE 180

1-Isopropyl-4-[1-(6-cyano-pyridin-3-yl)-piperidine-4-carbonyl]-[1,4]-diazepane hydrochloride (E180)

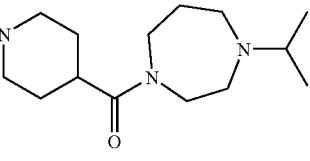

The title compound (E180) was prepared from 1-isopropyl-4-(piperidine-4-carbonyl)-[1,4]-diazepane (D8) and 5-bromo-2-cyanopyridine, in the presence of sodium tert-butoxide, following the procedure described for Example 154. ¹H NMR δ [MeOH-d4]: 1.28-1.41 (3H, m), 1.74-2.29 (7H, m), 3.00-3.37 (4H, m), 3.46-3.85 (6H, m), 4.05-4.10 (3H, m), 7.45 (1H, d, J=9.2 Hz), 7.71 (1H, d, J=9.2 Hz), 8.39 (1H,dd, J=2.8 Hz). MS electrospray (+ve ion) 356 (MH+).

EXAMPLES 181 and 182 (E181-E182)

Examples 181 and 182 were prepared as for Example 117 from 1-isopropyl-4-(piperdine-4-carbonyl)-[1,4]-diazepane (D8) and 5-chloro-2-methyl pyridine and 4-chloro-2-methyl pyridine respectively, and displayed ¹H NMR and mass spectral data that were consistent with structure.

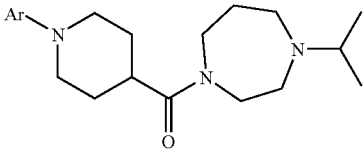

| Example No | Ar | Mass Spectrum (ES+) |
|---|---|---|
| E181 | 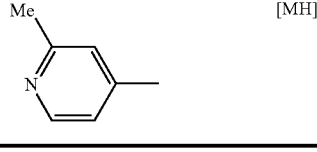 | [MH]+ 345 |
| E182 | | [MH]+ 345 |

EXAMPLE 183

1-Isopropyl-4-[1-(2-methyl-quinolin-4-yl)-piperldin-ecarbonyl]-[1,4]-diazepane hydrochloride (E183)

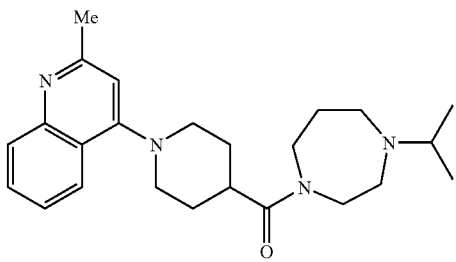

The title compound (E183) was prepared as for Example 180 from 1-isopropyl-4-(piperidine-4-carbonyl)-[1,4]-diazepane (D8) and 4-chloro-2-methyl-quinoline. $^1$H NMR δ[MeOH-d4]: 1.38-1.42 (6H, m), 2.01-2.05 (5H, m), 2.28-2.32 (1H, m), 3.15-3.23 (2H, m), 3.5-3.8 (8H, m), 3.9-3.95 (1H, m), 4.05-4.29 (3H, m), 7.08 (1H, s), 7.67 (1H, m), 7.85-7.94 (2H, m), 8.14-8.16 (1H, d, J=8 Hz). MS electrospray (+ve ion) 395 (MH+).

EXAMPLE 184

(S)-1-Isopropyl-4-[1-(2-methyl-quinolin-6-yl)-piperidine-4carbonyl]-2-methylpiperazine hydrochloride (E184)

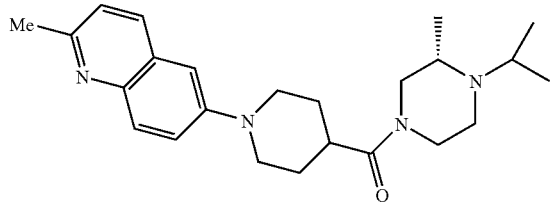

The title compound (E184) was prepared in a similar manner to that described in Example 89 using 6-bromo-2-methylquinoline and (S)-1-isopropyl-4(piperidine-4-carbonylI2-methyl piperazine (free base compound from D29). After work-up as described in Example 89 the hydrochloride salt was further purified using a Waters mass directed auto preparative HPLC eluting with 0.1% formic acid in water and 0.1% formic acid in acetonitrile (gradient 0-100%). Evaporation of the appropriate fractions gave the desired product as a formate salt which was dissolved in MeOH (2 ml), treated with ethereal HCl 1M (2 ml) and then evaporated to dryness to give the title compound (E184) as a light yellow gum. MS electrospray (+ve) 395 (MH+). $^1$H NMR.δ [MeOH-d4]: 1.28-1.29 (3H, m), 1.41.5 (8H, m), 1.9-2.05 (4H, m), 2.9 (3H, s), 2.98-3.2 (3H, m), 3.45-3.57 (3H, m), 4.04.08 (3H, m), 4.35-4.45 (1H, m), 4.6-4.78 (1H, s), 7.69 (1H, s), 7.78-7.80 (1H, d, J=8.8 Hz), 8.04 (2H, s), 8.78-8.81 (1H, d, J=8.8 Hz).

EXAMPLE 185

1-Isopropyl-4-{1-[4-(3-methyl-1,2,4-oxadiazol-5-yl)phenyl]-piperidine-4-carbonyl}-piperazine hydrochloride (E185)

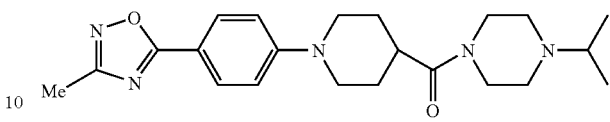

The title compound (E185) was prepared from 5-(4-bromophenyl)-3-methyl-1,2,4-oxadiazole (D41) and 1-isopropyl-4-(piperidine-4-carbonyl)piperazine (D1) following the procedure of Example 117. $^1$H NMR δ [DMSO-d6/D$_2$O]: 1.27-1.29 (6H, d, J=8 Hz), 1.5-1.78 (4H, br, m), 2.35 (3H, s), 2.85-3.15 (6H, br, m), 3.35-3.70 (4H, br, m), 3.924.0 (2H, br, m), 4.21-4.51 (2H, br, m), 7.08-7.10 (2H, d, J=8.8 Hz), 7.86-7.88 (2H, d, J=8.8 Hz), 10.89-11.00 (1H, br, s). LCMS electrospray (+ve) 398 (MH+).

EXAMPLES 186-189 (E186-E189)

Examples 186 and 187 were prepared from 5-(4-bromophenyl)-2-methyl-oxazole (D38) and 1-isopropyl-4-(piperidine4-carbonyl)-piperazine (D1) and 1-cyclobutyl-4-(piperidine-4-carbonyl)-piperazine (free base compound from D7) respectively, following the method of Example 117. Examples 188 and 189 were prepared from 1-cyclobutyl-4-(piperidine-4-carbonyl)-piperazine (free base compound from D7) and 3-(4-bromophenyl)-5-methyl-1,2,4oxadiazole (D40) and 5-(4-bromophenyl)-3-methyl-1,2,4-oxadiazole (D41) respectively, following the procedure of Example 118. Products displayed $^1$H NMR and mass spectral data that were consistent with structure.

| Example No | Ar | R | Mass Spectrum (ES+) |
|---|---|---|---|
| E186 | 2-methyl-oxazol-5-yl-phenyl | CH(Me)$_2$ | [MH]+ 397 |
| E187 | 2-methyl-oxazol-5-yl-phenyl | cyclobutyl | [MH]+ 409 |
| E188 | 5-methyl-1,2,4-oxadiazol-3-yl-phenyl | cyclobutyl | [MH]+ 410 |
| E189 | 3-methyl-1,2,4-oxadiazol-5-yl-phenyl | cyclobutyl | [MH]+ 410 |

EXAMPLE 190

1-Cyclobutyl-4-[1-(6-trifluoromethyl-pyridazin-3-yl)-piperidine-4-carbonyl]-piperazine hydrochloride (E190)

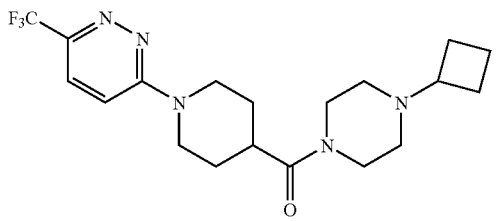

The title compound (E190) was prepared from 1-cyclobutyl-4-(piperidine-4-carbonyl)-piperazine (free base compound from D7) and 3-chloro-6-trifluoromethyl-pyridazine (A. J. Goodman, S. P. Stanforth and B. Tarbit, Tetrahedron, 1999, 55(52), 15067-15070) using the method described in Example 88. LCMS electrospray (+ve) 398 (MH$^+$). $^1$H NMR δ [MeOH-d4]: 1.86-2.02 (6H, m), 2.33-2.37 (4H, m), 2.78-2.89 (1H, m), 2.91-3.12 (2H, m), 3.23.3.28 (1H, m), 3.44-3.54 (6H, m), 3.71-3.75 (1H, m), 4.30-4.42 (2H, m), 4.67-4.70 (2×m, 1H), 7.95 (1H, d, J=10 Hz) and 8.00 (1H, d, J=10 Hz).

EXAMPLE 191

1-Isopropyl-4-[1-(2-trifluoromethylpyrimidin-5-yl)-piperidinecarbonyl]-piperazine hydrochloride (E191)

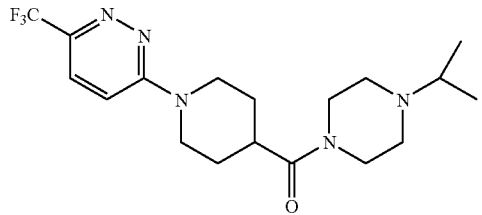

The title compound (E191) was prepared from 1-isopropyl-4-(piperidine-4-carbonyl)-piperazine (D1) and 5-bromo-2-trifluoromethylpyrimidine (D30) using the method described in Example 89. LCMS electrospray (+ve) 386 (MH$^+$). $^1$H NMR δ [DMSO-d6]: 1.27 (6H, d, J=7 Hz), 1.59-1.78 (4H, m), 2.77-3.05 (6H, m), 3.37-3.58 (4H, m), 4.00-4.05 (2H, 2×m), 4.21-4.26 (1H, 2×m), 4.47-4.52 (1H, 2×m), 8.62 (2H, s) and 10.31 (1H, bs).

EXAMPLES 192-194 (E192-194)

Examples 192-194 were prepared from 1-cyclobutyl-4-(piperidine-4-carbonyl)-[1,4]-diazepane (D10) and 5-(4-bromophenyl)-2-methyl-oxazole (D38), 3-(4-bromophenyl)-5-methyl-1,2,4-oxadiazole (D40) and 5-(4-bromo-phenyl)-3-methyl-1,2,4-oxadiazole (D41) respectively, following the procedure of Example 118. Products displayed $^1$H NMR and mass spectral data that were consistent with structure.

| Example No | Ar | Mass Spectrum (ES$^+$) |
|---|---|---|
| E192 | 5-(2-methyl-oxazol-5-yl)-4-methylphenyl | [MH]$^+$ 423 |
| E193 | 3-(5-methyl-1,2,4-oxadiazol-3-yl)-4-methylphenyl | [MH]$^+$ 424 |
| E194 | 5-(3-methyl-1,2,4-oxadiazol-5-yl)-4-methylphenyl | [MH]$^+$ 424 |

EXAMPLES 195-197 (E195-197)

Examples 195 and 196 were prepared from 1-cyclobutyl-4-(piperidine-4-carbonyl)-[1,4]-diazepane (D10) and 2-chloro-5-trifluoromethylpyrazine (D31) and 3-chloro-6-trifluoromethylpyridazine (A. J. Goodman, S. P. Stanforth and B. Tarbit, Tetrahedron, 1999, 55(52), 15067-15070) respectively, using the method described in Example 88. Example 197 was prepared from 1-cyclobutyl-4-(piperidine-4-carbonyl)-[1,4]-diazepane (D10) and 5-bromo-2-trifluoromethylpyrimidine (D30) using the method described in Example 89. Products displayed $^1$H NMR and mass spectral data that were consistent with structure.

| Example No | Ar | Mass Spectrum (ES$^+$) |
|---|---|---|
| E195 | 5-trifluoromethyl-pyrazin-2-yl | [MH]$^+$ 412 |
| E196 | 6-trifluoromethyl-pyridazin-3-yl | [MH]$^+$ 412 |
| E197 | 2-trifluoromethyl-pyrimidin-5-yl | [MH]$^+$ 412 |

EXAMPLE 198

1-Isopropyl-4-[1-(2-trifluoromethylpyrimidin-5-yl)-piperidine-4-carbonyl]-[1,4]-diazepane hydrochloride (E198)

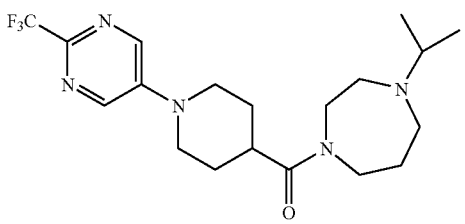

The title compound (E198) was prepared from 1-isopropyl-4-(piperidine-4-carbonyl)-[1,4]-diazepane (D8) and 5-bromo-2-trifluoromethylpyrimidine (D30) using the method described in Example 89. LCMS electrospray (+ve) 400 (MH$^+$). $^1$H NMR δ [MeOH-d4]: 1.35 (6H, m), 1.84-1.91 (4H, m), 2.19-2.29 (2H, m), 2.98-3.30 (4H, m), 3.55-3.73 (6H, m), 3.83-3.86 (1H, m), 4.02-4.21 (3H, m) and 8.53 (2H, s).

Abbreviations

| | |
|---|---|
| DCM | dichloromethane |
| DMSO | dimethylsulfoxide |
| DMF | N,N-dimethylformamide |
| EDC | 1-(3-dimethylaminopropyl)-3-ethylcarbodiimide hydrochloride |
| EtOAc | ethyl acetate |
| HOAT | 1-hydroxy-7-azabenzotriazole |
| HOBt | 1-hydroxybenzotriazole |
| h | hour |
| min | minutes |
| rt | room temperature |
| TEA | triethylamine |
| TFA | trifluoroacetic acid |
| THF | tetrahydrofuran |

All publications, including but not limited to patents and patent applications, cited in this specification are herein incorporated by reference as if each individual publication were specifically and individually indicated to be incorporated by reference herein as though fully set forth.

Biological Data

A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pCDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos. 5,364,791; 5,874,534; and 5,935,934. Ligated DNA was transformed into competent DH5α E. coli host bacterial cells and plated onto Luria Broth (LB) agar containing Zeocin™ (an antibiotic which allows the selection of cells expressing the sh ble gene which is present on pGene and pSwitch) at 50 µg ml$^{-1}$. Colonies containing the re-ligated plasmid were identified by restriction analysis. DNA for transfection into mammalian cells was prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) were seeded at 2×10e6 cells per T75 flask in Complete Medium, containing Hams F12 (GIBCOBRL, Life Technologies) medium supplemented with 10% v/v dialysed foetal bovine serum, L-glutamine, and hygromycin (100 µg ml$^{-1}$), 24 hours prior to use. Plasmid DNA was transfected into the cells using Lipofectamine plus according to the manufacturers guidelines (InVitrogen). 48 hours post transfection cells were placed into complete medium supplemented with 500 µg ml$^{-1}$ Zeocin™.

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 µm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 µg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of buffer A2 containing 50 mM N-2-hydroxyethylpiperazine-N'-2-ethanesulfonic acid (HEPES)(pH 7.40) supplemented with 10e−4M leupeptin (acetyl-leucyl-leucyl-arginal; Sigma L2884), 25 µg/ml bacitracin (Sigma B0125), 1 mM ethylenediamine tetra-acetic acid (EDTA), 1 mM phenylmethylsulfonyl fluoride (PMSF) and 2×10e−6M pepstain A (Sigma). The cells are then homogenised by 2×15 second bursts in a 1 litre glass Waring blender, followed by centrifugation at 500 g for 20 minutes. The supernatant is then spun at 48,000 g.for 30 minutes. The pellet is resuspended in 4 volumes of buffer A2 by vortexing for 5 seconds, followed by homogenisation in a Dounce homogeniser (10-15 strokes). At this point the preparation is aliquoted into polypropylene tubes and stored at −70° C.

Compounds of the invention may be tested for in vitro biological activity in accordance with the following assays:

(I) Histamine H3 Binding Assay

For each compound being assayed, in a white walled clear bottom 96 well plate, is added:-

(a) 10 μl of test compound (or 10 μl of iodophenpropit (a known histamine H3 antagonist) at a final concentration of 10 mM) diluted to the required concentration in 10% DMSO;
(b) 10 μl $^{125}$I 4-[3-(4-iodophenylmethoxy)propyl]-1H-imidazolium (iodoproxyfan) (Amersham; 1.85MBq/μl or 50 μCi/ml; Specific Activity ~2000 Ci/mmol) diluted to 200 pM in assay buffer (50 mM Tris(hydroxymethyl)aminomethane buffer (TRIS) pH 7.4, 0.5 mM ethylenediamine tetra-acetic acid (EDTA)) to give 20 pM final concentration; and
(c) 80 μl bead/membrane mix prepared by suspending Scintillation Proximity Assay (SPA) bead type WGA-PVT at 100 mg/ml in assay buffer followed by mixing with membrane (prepared in accordance with the methodology described above) and diluting in assay buffer to give a final volume of 80 μl which contains 7.5 μg protein and 0.25 mg bead per well—mixture was pre-mixed at room temperature for 60 minutes on a roller. The plate is shaken for 5 minutes and then allowed to stand at room temperature for 3-4 hours prior to reading in a Wallac Microbeta counter on a 1 minute normalised tritium count protocol. Data was analysed using a 4-parameter logistic equation.

(II) Histamine H3 Functional Antagonist Assay

For each compound being assayed, in a white walled clear bottom 96 well plate, is added:—
(a) 10 μl of test compound (or 10 μl of guanosine 5'-triphosphate (GTP)(Sigma) as non-specific binding control) diluted to required concentration in assay buffer (20 mM N-2-Hydroxyethylpiperazine-N'-2-ethanesulfonic acid (HEPES)+100 mM NaCl+10 mM $MgCl_2$, pH7.4 NaOH);
(b) 60 μl bead/membrane/GDP mix prepared by suspending wheat germ agglutinin-polyvinyltoluene (WGA-PVT) scintillation proximity assay (SPA) beads at 100 mg/ml in assay buffer followed by mixing with membrane (prepared in accordance with the methodology described above) and diluting in assay buffer to give a final volume of 60 μl which contains 10 μg protein and 0.5 mg bead per well—mixture is pre-mixed at 4° C. for 30 minutes on a roller and just prior to addition to the plate, 10 μM final concentration of guanosine 5' diphosphate (GDP)(Sigma; diluted in assay buffer) is added;

The plate is incubated at room temperature to equilibrate antagonist with receptor/beads by shaking for 30 minutes followed by addition of:
(c) 10 μl histamine (Tocris) at a final concentration of 0.3 μM; and
(d) 20 μl guanosine 5' [γ35-S] thiotriphosphate, triethylamine salt (Amersham; radioactivity concentration=37 kBq/μl or 11 mCi/ml; Specific Activity 1160 Ci/mmol) diluted to 1.9 nM in assay buffer to give 0.38 nM final.

The plate is then incubated on a shaker at room temperature for 30 minutes followed by centrifugation for 5 minutes at 1500 rpm. The plate is read between 3 and 6 hours after completion of centrifuge run in a Wallac Microbeta counter on a 1 minute normalised tritium count protocol. Data is analysed using a 4-parameter logistic equation. Basal activity used as minimum i.e. histamine not added to well.

Results

The compounds of Examples E1-E80, E82-E88, E90-E183 and E185-E198 were tested in the histamine H3 functonal antagonist assay and exhibited $pK_b$ values ≧7.5. More particularly, the compounds of E1, E2, E4, E8-E17, E25, E30, E31, E33, E35-E46, E54, E56, E59, E61-E70, E78-E79, E86-E88, E90-E91, E96-E97, E102, E104-E105, E118, E129, E135-E139, E150-E151, E154, E168-E170, E179-E180, E183, E185 and E198 exhibited $pK_b$ values >8.5. Yet more particularly, the compounds of E2, E36-E38, E79, E96, E135 and E150-151 exhibited $pK_b$ values >9.0. Most particularly, the compounds of E96 and E135 exhibited $pK_b$ values >9.5.

What is claimed is:
1. A compound of formula (I) or a pharmaceutically acceptable salt or thereof:

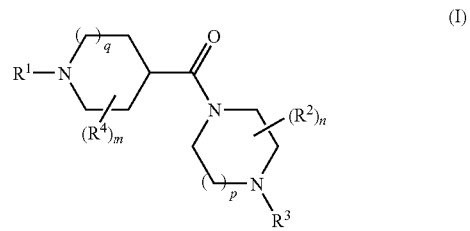

wherein:
$R^1$ represents aryl, heteroaryl, -aryl-X—$C_{3-7}$ cycloalkyl, -heteroaryl-X—$C_{3-7}$ cycloalkyl, -aryl-X-aryl, -aryl-X-heteroaryl, -aryl-X-heterocyclyl, -heteroaryl-X-heteroaryl, -heteroaryl-X-aryl or -heteroaryl-X-heterocyclyl;

wherein said aryl, heteroaryl and heterocyclyl groups of $R^1$ may be optionally substituted by one or more substituents which may be the same or different, and which are selected from the group consisting of halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, —CO$C_{1-6}$ alkyl, —CO$C_{1-6}$ alkyl-halogen, —CO$C_{1-6}$ alkyl-cyano, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, aryl, arylsulfonyl, arylsulfonyloxy, aryloxy, arylsulfonamido, arylcarboxamido, aroyl, $NR^{15}R^{16}$, —$CONR^{15}R^{16}$, —$NR^{15}COR^{16}$, —$C(R^{15})$=$NOR^{16}$, —$NR^{15}SO_2R^{16}$ and —$SO_2NR^{15}R^{16}$, wherein $R^{15}$ and $R^{16}$ independently represent hydrogen or $C_{1-6}$ alkyl or together form a heterocyclic ring;

X represents a bond, O, CO, $SO_2$, $OCH_2$ or $CH_2O$;

each $R^2$ and $R^4$ independently represents $C_{1-4}$ alkyl;

$R^3$ represents $C_{3-8}$ alkyl, $C_{3-6}$ alkenyl, $C_{3-6}$ alkynyl, $C_{3-6}$ cycloalkyl, $C_{5-6}$ cycloalkenyl or —$C_{1-4}$alkyl-$C_{3-6}$ cycloalkyl;

wherein said $C_{3-6}$ cycloalkyl groups of $R^3$ may be optionally substituted by one or more substituents which may be the same or different, and which are selected from the group consisting of halogen, $C_{1-4}$ alkyl and trifluoromethyl;

m and n independently represent 0, 1 or 2;

p and q independently represent 1.

2. A compound of formula (I) as defined in claim 1 wherein $R^1$ represents
-aryl optionally substituted by 1, 2 or 3 halogen, $C_{1-6}$ alkyl, polyhalo$C_{1-6}$ alkyl, $C_{1-6}$ alkoxy, polyhalo$C_{1-6}$ alkoxy, —CO$C_{1-6}$ alkyl, —$C(R^{15})$=$NOR^{16}$, —$NR^{15}COR^{16}$, —CO$C_{1-6}$ alkyl-halogen, —CO$C_{1-6}$ alkyl-cyano, cyano or $C_{1-6}$ alkoxycarbonyl groups;
-aryl-X—$C_{3-7}$ cycloalkyl;
-aryl-X-aryl;
-aryl-X-heterocyclyl optionally substituted by 1, 2 or 3 halogen or oxo groups;

-aryl-X-heteroaryl optionally substituted by a $C_{1-6}$ alkyl or aryl group;

heteroaryl optionally substituted by 1, 2 or 3 cyano, halogen, polyhalo$C_{1-6}$ alkyl, $C_{1-6}$ alkyl, $C_{1-6}$ alkoxy, $C_{1-6}$ alkoxycarbonyl or —$CONR^{15}R^{16}$ groups;

-heteroaryl-X-aryl optionally substituted by 1, 2 or 3 cyano or $C_{1-6}$ alkylsulfonyl groups;

-heteroaryl-X-heterocyclyl; or

-heteroaryl-X-heteroaryl.

3. A compound of formula (I) as defined in claim 2 wherein $R^1$ represents phenyl, naphthyl or indanone optionally substituted by 1, 2 or 3 halogen, $C_{1-6}$ alkyl, polyhalo$C_{1-6}$ alkyl, $C_{1-6}$ alkoxy, polyhalo$C_{1-6}$ alkoxy, —$COC_{1-6}$ alkyl, —$C(R^{15})$ =$NOR^{16}$, —$NR^{15}COR^{16}$, —$COC_{1-6}$ alkyl-halogen, —$COC_{1-6}$ alkyl-cyano, cyano or $C_{1-6}$ alkoxycarbonyl groups;

-phenyl-CO-cyclopropyl or -phenyl-CO-cyclobutyl;

-phenyl-thiazolyl, -phenyl-oxadiazolyl, -phenyl-pyrrolyl, -phenyl-oxazolyl or -phenyl-isoxaxolyl optionally substituted by a $C_{1-6}$ alkyl or aryl group; or pyridyl, pyrimidyl, pyrazinyl, pyridazinyl, quinolinyl, isoquinolinyl or benzothiazolyl optionally substituted by 1, 2 or 3 cyano, halogen, polyhalo$C_{1-6}$ alkyl, $C_{1-6}$ alkyl, $C_{1-6}$ alkoxy, $C_{1-6}$ alkoxycarbonyl or —$CONR^{15}R^{16}$ groups.

4. A compound of formula (I) as defined in claim 3 wherein $R^1$ represents phenyl optionally substituted by 1, 2 or 3 halogen, polyhalo$C_{1-6}$ alkyl, —$NR^{15}COR^{16}$, —$COC_{1-6}$ alkyl or cyano groups;

-phenyl-CO-cyclopropyl;

-phenyl-oxadiazolyl or -phenyl-oxazolyl optionally substituted by a $C_{1-6}$ alkyl or aryl group; or pyridyl, pyrimidyl, pyrazinyl, pyridazinyl or quinolinyl optionally substituted by 1, 2 or 3 halogen, polyhalo$C_{1-6}$ alkyl, $C_{1-6}$ alkyl or cyano groups.

5. A compound of formula (I) as defined in claim 4 wherein $R^1$ represents phenyl optionally substituted at the 4-position by a —COMe, —COEt or cyano group; or pyridyl or quinolinyl optionally substituted by a methyl or $CF_3$ group.

6. A compound of formula (I) as defined in claim 5 wherein $R^1$ represents

-6-$CF_3$-pyridin-3-yl.

7. A compound of formula (I) as defined in claim 1 wherein X represents a bond, O or CO.

8. A compound of formula (I) as defined in claim 7, wherein X represents a bond or CO.

9. A compound of formula (I) as defined in claim 1 wherein m represents 0.

10. A compound of formula (I) as defined in claim 1 wherein n represents 0, 1.

11. A compound of formula (I) as defined in claim 1 wherein $R^2$ represents methyl.

12. A compound of formula (I) as defined in claim 10 wherein n represents 0.

13. A compound of formula (I) as defined claim 1 wherein $R^3$ represents $C_{3-8}$ alkyl or $C_{3-6}$ cycloalkyl.

14. A compound of formula (I) as defined in claim 13 wherein $R^3$ represents isopropyl, isobutyl or cyclobutyl.

15. A compound of formula (I) as defined in claim 14 wherein $R^3$ represents isopropyl or cyclobutyl.

16. A compound of formula (I) as defined in claim 15 wherein $R^3$ represents isopropyl.

17. A compound of formula (I) as defined in claim 1 which is 1-Isopropyl-4-[1-(5-cyano-pyridin-2-yl)-piperidine-4-carbonyl]-piperazine;

1-Isopropyl-4-[1-(5-methoxycarbonyl-4-trifluoromethylpyridin-2-yl)-piperidine-4-carbonyl]-piperazine;

1-Isopropyl-4-[1-(4ethoxycarbonylphenyl)-piperidine-4-carbonyl]-piperazine;

1-Cyclobutyl-4-[1-(4-cyanophenyl)-piperidine-4-carbonyl]-piperazine;

1-Cyclobutyl-4-[1-(4-cyano-3-fluorophenyl)-piperidine-4-carbonyl]-piperazine;

1-Cyclobutyl4-[1-(4-cyano-2,6-difluorophenyl)-piperidine-4-carbonyl]-piperazine;

1-Cyclobutyl-4-[1-(4-cyano-3-trifluoromethylphenyl)-piperidine-4-carbonyl]-piperazine;

1-Cyclobutyl-4-[1-(4-cyano-naphthalen-1-yl)-piperidine-4-carbonyl]-piperazine;

1-Cyclobutyl-4-[1-(5-cyanopyridin-2-yl)-piperidine-4-carbonyl]-piperazine;

1-Cyclobutyl-4-[1-(6-trifluoromethylpyridin-2-yl)-piperidine-4-carbonyl]-piperazine;

1-Cyclobutyl-4-[1-(5-trifluoromethylpyridin-2-yl)-piperidine-4-carbonyl]-piperazine;

1-Cyclobutyl-4-[1-(3-chloro-5-trifluoromethylpyridin-2-yl)-piperidine-4-carbonyl]-piperazine;

1-Isopropyl-4-{1-[5-(4-methylsulfonylphenyl)-pyrimidin-2-yl]-piperidine-4-carbonyl}-piperazine;

1-Isopropyl-4-{1-[4-(morpholino-carbonyl)-phenyl]-piperidine-4-carbonyl}-piperazine;

1-Cyclopentyl-4-[1-(4-cyano-phenyl)-piperidine4-carbonyl]-piperazine;

(2R,6S)-1-Cyclobutyl-4-[1-(4-cyanophenyl)-piperidine-4-carbonyl]-2,6-dimethylpiperazine;

1-Isopentyl4-[1-(5-cyano-pyridin-2-yl)-piperidine-4-carbonyl]-piperazine;

(S)-1-Isopropyl-4-[1-(4-cyanophenyl)-piperidine-4-carbonyl]-2-methylpiperazine;

(S)-1-Isopropyl-4-[1-(6-cyanopyridin-3-yl)-piperidine-4-carbonyl]-2-methyl piperazine;

(S)-1-Isopropyl-4-[1-(5-cyanopyridin-2-yl)-piperidine-4-carbonyl]-[2-methyl piperzine;

(S)-1-Isopropyl-4-[1-(5-triflourmethyl-pyrazin-2-yl)-piperidine-4-carbonyl]-[2-methyl piperazine;

(S)-1-Isopropyl-4-[1(6-trifluoromethyl-pyridazin-3-yl)-piperidine-4-carbonyl]-2-methyl piperazine;

1-Isopropyl-4-{1-[4-(5-phenyl-1,3,4-oxadiazol-2-yl)phenyl]-piperidine-4-carbonyl}piperazine;

1-Isopropyl-4-[1-(quinolin-6-yl)-piperidine-4-carbonyl] piperazine;

1-Cyclobutyl-4-[1-(6-trifluoromethylpyridin-3-yl)-piperidine-4-carbonyl]piperazine;

1-Isopropyl-4-[1-(5-trifluoromethyl-pyrazin-2-yl)-piperidine-4-carbonyl]-piperazine;

(S)-1-Isobutyl-4-[1-(4-cyanophenyl)-piperidine-4-carbonyl]-piperazine;

1-Isopropyl-4-[1-(4-cyclopropylcarbonylphenyl)-piperidine-4-carbonyl]-piperazine;

1-Isopropyl-4-[1-(2-methyl-quinolin-6-yl)-piperidine-4-carbonyl]-piperazine;

1-Isopropyl-4-[1-(6-cyano-pyridin-3-yl)-piperidine-4-carbonyl]-piperazine;

1-Isopropyl-4-{1-[4-(3-methyl-1,2,4-oxadiazol-5-yl)phenyl]-piperidine-4-carbonyl}-piperazine;

or a pharmaceutically acceptable salt thereof.

18. A compound of formula (I) as defined in claim 1 which is

1-Isopropyl-4-[1-(4-cyanophenyl)-piperidine-4-carbonyl]-piperazine;

(S)-1-Isopropyl-4-[1-(6-trifluoromethylpyridin-3-yl)-piperidine-4-carbonyl]-2-methyl piperazine;

or a pharmaceutically acceptable salt or salt thereof.

19. A compound of formula (I) as defined in claim 1 which is

1-Isopropyl-4-[1-(6-trifluoromethylpyridin-3-yl)-piperidine-4-carbonyl]-piperazine;

or a pharmaceutically acceptable salt thereof.

20. A pharmaceutical composition which comprises the compound of formula (I) as defined in claim 1 or a pharmaceutically acceptable salt thereof and a pharmaceutically acceptable carrier or excipient.

21. A method of treatment of neurological diseases which comprises administering to a host in need thereof an effective amount of a compound of formula (I) as defined in claim 1 or a pharmaceutically acceptable salt thereof, Wherein said neurological disease is selected from the group consisting of Alzhiemer's disease, mild cognitive impairment, and age-related memory dysfunction.

22. A process for the preparation of a compound of formula (I) or a pharmaceutically acceptable salt thereof, which process comprises:

(a) reacting a compound of formula (II)

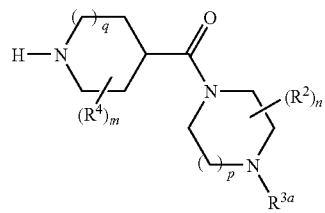

(II)

or an optionally activated or protected derivative thereof, wherein $R^2$, $R^4$, m, n, p and q are as defined in claim 1 and $R^{3a}$ is as defined for $R^3$ in claim 1 or a group convertible to $R^3$, with a compound of formula $R^1$-$L^1$, wherein $R^1$ is as defined in claim 1 and $L^1$ represents a suitable leaving group, followed by a deprotection reaction as necessary; or (b) reacting a compound of formula (III)

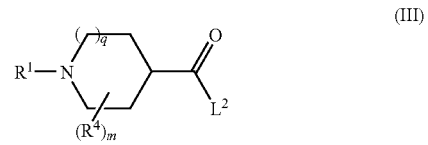

(III)

wherein $R^1$, $R^4$, m and q are as defined in claim 1 and $L^2$ represents OH or a suitable leaving group, with a compound of formula (IV)

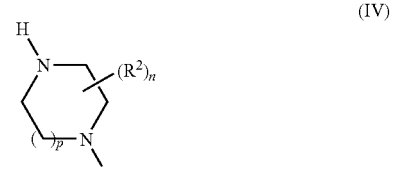

(IV)

wherein $R^2$, n and p are as defined in claim 1 $R^{3a}$ is as defined for $R^3$ in claim 1 or a group convertible to $R^3$; or (c) deprotecting a compound of formula (I) or converting groups which are protected; and optionally thereafter (d) interconversion to other compounds of formula (I).

* * * * *